# United States Patent
Register

US011260023B2

(10) Patent No.: US 11,260,023 B2
(45) Date of Patent: Mar. 1, 2022

(54) TOPICAL COMPOSITIONS CONTAINING ROFECOXIB AND METHODS OF MAKING AND USING THE SAME

(71) Applicant: BRIORI BIOTECH, LLC, Carlsbad, CA (US)

(72) Inventor: Robert Bruce Register, Oceanside, CA (US)

(73) Assignee: BRIORI BIOTECH, LLC, Carlsbad, CA (US)

( * ) Notice: Subject to any disclaimer, the term of this patent is extended or adjusted under 35 U.S.C. 154(b) by 0 days.

(21) Appl. No.: 17/183,130

(22) Filed: Feb. 23, 2021

(65) Prior Publication Data
US 2021/0220259 A1    Jul. 22, 2021

Related U.S. Application Data

(63) Continuation of application No. PCT/US2021/012769, filed on Jan. 8, 2021.

(60) Provisional application No. 62/959,624, filed on Jan. 10, 2020.

(51) Int. Cl.
| | |
|---|---|
| A61K 9/00 | (2006.01) |
| A61K 31/341 | (2006.01) |
| A61K 47/46 | (2006.01) |
| A61K 47/38 | (2006.01) |
| A61K 47/22 | (2006.01) |
| A61K 47/12 | (2006.01) |
| A61P 29/00 | (2006.01) |
| A61K 47/14 | (2017.01) |
| A61K 47/10 | (2017.01) |
| A61K 47/26 | (2006.01) |

(52) U.S. Cl.
CPC .......... *A61K 9/0014* (2013.01); *A61K 31/341* (2013.01); *A61K 47/10* (2013.01); *A61K 47/12* (2013.01); *A61K 47/14* (2013.01); *A61K 47/22* (2013.01); *A61K 47/26* (2013.01); *A61K 47/38* (2013.01); *A61K 47/46* (2013.01); *A61P 29/00* (2018.01)

(58) Field of Classification Search
None
See application file for complete search history.

(56) References Cited

U.S. PATENT DOCUMENTS

| | | |
|---|---|---|
| 6,552,031 B1 | 4/2003 | Burch et al. |
| 7,018,649 B2 | 3/2006 | Tavares et al. |
| 9,814,670 B2 | 11/2017 | Gan et al. |
| 10,456,438 B2 | 10/2019 | Mark |
| 2005/0049291 A1 | 3/2005 | Kumar et al. |
| 2006/0182771 A1* | 8/2006 | Dor ...................... A61K 9/0019 424/400 |
| 2012/0004305 A1* | 1/2012 | Miura .................... A61K 47/10 514/567 |
| 2012/0283233 A1* | 11/2012 | Gavin ...................... A61K 9/06 514/180 |
| 2013/0304165 A1 | 11/2013 | Rogers |
| 2014/0349943 A1* | 11/2014 | Gadek .................... A61P 17/10 514/18.7 |
| 2017/0087199 A1 | 3/2017 | Patron et al. |

FOREIGN PATENT DOCUMENTS

WO    WO 2007/120868 A2    10/2007

OTHER PUBLICATIONS

Pennsaid FDA Label, 28 pages.
Q3C—Tables and List Guidance for Industry, Aug. 2018, ICH, Revision 4, 10 pages.
Agdeppa et al., "Binding Characteristics of Radiofluorinated 6-Dialkylamino-2-Naphthylethylidene Derivatives as Positron Emission Tomography Imaging Probes for β-Amyloid Plaques in Alzheimer's Disease," The Journal of Neuroscience, 2001, vol. 21, 5 pages.
Agdeppa et al., "In Vitro Detection of (S)-Naproxen and Ibuprofen Binding to Plaques in the Alzheimer's Brain Using the Positron Emission Tomography Molecular Imaging Probe 2-(1-{6-[(2-[18F]Fluoroethyl)(Methyl)Amino]-2-Napthyl}Ethylidene) Malononitrile," Neuroscience 117 (2003) 723-730.
Ahmad et al., "Renal Failure Associated with the Use of Celecoxib and Rofecoxib," Drug Safety 2002; 25 (7), pp. 537-544.
Ahuja et al., "Rofecoxib: an update on physicochemical, pharmaceutical, pharmacodynamic and pharmacokinetic aspects," Journal of Pharmacy and Pharmacology, 2003, 55: 859-894.
Anderson et al., "Platelet Inhibition Reduces Cyclic Flow Variations and Neointimal Proliferation in Normal and Hypercholesterolemic-Atherosclerotic Canine Coronary Arteries," Circulation, 2001;104:2331-2337.
Araujo et al., "Cardiovascular Events: A Class Effect by COX-2 Inhibitors," Arquivos Brasileiros de Cardiologia—vol. 85, No. 3, Sep. 2005, 8 pages.
Baigent et al., "Selective Cyclooxygenase 2 Inhibitors, Aspirin, and Cardiovascular Disease," Arthritis & Rheumatism, vol. 48, No. 1, Jan. 2003, pp. 12-20.
Bain et al., "Pharmacology of AM211, a Potent and Selective Prostaglandin D2 Receptor Type 2 Antagonist That Is Active in Animal Models of Allergic Inflammation," JPET 338:290-301, 2011.
Bally et al., "Risk of acute myocardial infarction with NSAIDs in real world use: bayesian meta-analysis of individual patient data," BMJ 2017;357:j1909, 13 pages.
Bally et al., "Risk of acute myocardial infarction with real-world NSAIDs depends on dose and timing of exposure," PDS, vol. 27, Issue 1, Jan. 2018, pp. 69-77.
Bally et al., "Studying additive interaction in a healthcare database: Case study of NSAIDs, cardiovascular profiles, and acute myocardial infarction," PLoS One 13(8), Aug. 10, 2018, 15 pages.
(Continued)

*Primary Examiner* — Nannette Holloman
(74) *Attorney, Agent, or Firm* — Cooley LLP

(57) ABSTRACT

The present disclosure provides topical compositions of rofecoxib and methods of making said compositions. The present disclosure also provides methods of using topical compositions of rofecoxib to treat inflammation.

28 Claims, 15 Drawing Sheets

(56) References Cited

OTHER PUBLICATIONS

Balmaceda, "Evolving guidelines in the use of topical nonsteroidal anti-inflammatory drugs in the treatment of osteoarthritis," Balmaceda BMC Musculoskeletal Disorders 2014, 15:27.
Bannuru et al., "OARSI guidelines for the non-surgical management of knee, hip, and polyarticular osteoarthritis," Osteoarthritis and Cartilage, Jul. 13, 2019, 12 pages, https://doi.org/10.1016/j.joca.2019.06.011.
Bathurst et al., "Soy (Glycine max)-Derived Phospholipids Exhibit Potent Anti-Apoptotic Activity," Pharmaceutical Biology, 1998, 36:2, 111-123.
Bensen et al., "Efficacy and safety of valdecoxib in treating the signs and symptoms of rheumatoid arthritis: a randomized, controlled comparison with placebo and naproxen," Rheumatology 2002;41:1008-1016.
Besson, "The neurobiology of pain," Lancet 1999; 353: 1610-15.
Bhala et al., "Vascular and upper gastrointestinal effects of non-steroidal anti-infl ammatory drugs: meta-analyses of individual participant data from randomised trials," Lancet 2013; 382:769-79.
Birk et al., "Role of extracellular ATP metabolism in regulation of platelet reactivity," J Lab Clin Med 2002;140:166-75.
Black et al., "2,3-Diarylcyclopentenones as Orally Active, Highly Selective Cyclooxygenase-2 Inhibitors," J. Med. Chem. 1999, 42, 1274-1281.
Blobaum et al., "Structural and Functional Basis of Cyclooxygenase Inhibition," Journal of Medicinal Chemistry, 2007, vol. 50, No. 7, pp. 1425-1441.
Bombardier et al., "Comparison of Upper Gastrointestinal Toxicity of Rofecoxib and Naproxen in Patients With Rheumatoid Arthritis," N Engl J Med 2000;343:1520-8.
Bravo et al., "Identification of the first potent, selective and bioavailable PPARα antagonist," Bioorganic & Medicinal Chemistry Letters 24 (2014) 2267-2272.
Brune et al., "New insights into the use of currently available non-steroidal anti-inflammatory drugs," Journal of Pain Research 2015:8 105-118.
Cantor, "Pharmacoeconomics of Coxib Therapy," J Pain Symptom Manage 2002;24:S28-S37.
Cao et al., "Measurement of cyclooxygenase inhibition using liquid chromatography-tandem mass spectrometry," J Pharm Biomed Anal. Jan. 5, 2011; 54(1): 230-235.
Carr et al., "Acute pain," Lancet 1999; 353: 2051-58.
Cervero et al., "Visceral pain," Lancet 1999; 353: 2145-48.
Chan et al., "Rofecoxib [Vioxx, MK-0966; 4-(4'-Methylsulfonylphenyl)-3-phenyl-2-(5H)-furanone]: A Potent and Orally Active Cyclooxygenase-2 Inhibitor. Pharmacological and Biochemical Profiles," JPET 290:551-560, 1999.
Chan et al., "Celecoxib Versus Diclofenac and Omeprazole in Reducing the Risk of Recurrent Ulcer Bleeding in Patients With Arthritis," N Engl J Med, vol. 347, No. 26, Dec. 26, 2002, pp. 2104-2110.
Chandrasekharan et al., "COX-3, a cyclooxygenase-1 variant inhibited by acetaminophen and other analgesic/antipyretic drugs: Cloning, structure, and expression," PNAS, Oct. 15, 2002, vol. 99, No. 21, pp. 13926-13931.
Chang et al., "Generic Development of Topical Dermatologic Products: Formulation Development, Process Development, and Testing of Topical Dermatologic Products," The AAPS Journal, vol. 15, No. 1, Jan. 2013.
Chapman et al., "Suffering: the contributions of persistent pain," Lancet 1999; 353: 2233-37.
Chavez-Eng et al., "Determination of Rofecoxib (MK-0966), a cyclooxygenase-2 inhibitor, in human plasma by high-performance liquid chromatography with tandem mass spectrometric detection," Journal of Chromatography B, 748 (2000) 31-39.
Chavez-Eng et al., "High-performance liquid chromatographic-tandem mass spectrometric evaluation and determination of stable isotope labeled analogs of rofecoxib in human plasma samples from oral bioavailability studies," Journal of Chromatography B, 767 (2002) 117-129.

Chenevard et al., "Selective COX-2 Inhibition Improves Endothelial Function in Coronary Artery Disease," Circulation. 2003;107:405-409.
Chrubasik et al., "Treatment of low back pain with a herbal or synthetic anti-rheumatic: a randomized controlled study. Willow bark extract for low back pain," Rheumatology 2001;40:1388-1393.
Cieslik et al., "Salicylate Suppresses Macrophage Nitric-oxide Synthase-2 and Cyclo-oxygenase-2 Expression by Inhibiting CCAAT/Enhancerbinding Protein-β Binding via a Common Signaling Pathway," The Journal of Biological Chemistry, vol. 277, No. 51, Issue of Dec. 20, pp. 49304-49310, 2002.
Cieslik et al., "Inhibition of p90 Ribosomal S6 Kinase-mediated CCAAT/Enhancerbinding Protein β Activation and Cyclooxygenase-2 Expression by Salicylate," The Journal of Biological Chemistry, vol. 280, No. 18, Issue of May 6, pp. 18411-18417, 2005.
Cilurzo, "Design of in vitro skin permeation studies according to the EMA Guideline on quality of transdermal patches," Elsevier Editorial System(tm) for European Journal of Pharmaceutical Sciences, Sep. 7, 2018, 26 pages.
Cochrane et al., "Etoricoxib," Drugs 2002; 62 (18): 2637-2651.
Cordoba-Diaz et al., "Validation protocol of an automated in-line flow-through diffusion equipment for in vitro permeation studies," Journal of Controlled Release 69 (2000) 357-367.
Dalen, "Selective COX-2 Inhibitors, NSAIDs, Aspirin, and Myocardial Infarction," Arch Intern Med, vol. 162, May 27, 2002, pp. 1091-1092.
Das et al., "Formulation and Ex Vivo Evaluation of Rofecoxib Gel for Topical Application," Acta Poloniae Pharmaceutica—Drug Research, vol. 63 No. 5 pp. 461-467, 2007.
Day et al., "A Randomized Trial of the Efficacy and Tolerability of the COX-2 Inhibitor Rofecoxib vs Ibuprofen in Patients With Osteoarthritis," Arch Intern Med. 2000;160:1781-1787.
De Abajo et al., "Risk of nonfatal acute myocardial infarction associated with nonsteroidal antiinflammatory drugs, non-narcotic analgesics and other drugs used in osteoarthritis: a nested case-control study," Pharmacoepidemiology and Drug Safety 2014; 23: 1128-1138.
Dean, "Structural Examination of 6-Methylsulphonylphenanthro-[9,10-C]-furan-1(3H)-one—A Rofecoxib Degradation Product," Pharmaceuticals 2010, 3, 369-378.
Deeks et al., "Efficacy, tolerability, and upper gastrointestinal safety of celecoxib for treatment of osteoarthritis and rheumatoid arthritis: systematic review of randomised controlled trials," BMJ 2002;325:619-23.
Delmas et al., "Efficacy of Raloxifene on Vertebral Fracture Risk Reduction in Postmenopausal Women with Osteoporosis: Four-Year Results from a Randomized Clinical Trial," J Clin Endocrinol Metab, Aug. 2002, 87(8):3609-3617.
Deng et al., "Aspirin and salicylate bind to immunoglobulin heavy chain binding protein (BiP) and inhibit its ATPase activity in human fibroblasts," The FASEB Journal, vol. 15, Nov. 2001, pp. 2463-2470.
Depre et al., "Pharmacokinetics, COX-2 speci@city, and tolerability of supratherapeutic doses of rofecoxib in humans," Eur J Clin Pharmacol (2000) 56: 167-174.
Derry et al., "Topical NSAIDs for chronic musculoskeletal pain in adults," Cochrane Database Syst Rev. Author mauscript; available in PMC Sep. 10, 2014; 9: CD007400, 91 pages.
Derry et al., "Topical NSAIDs for acute musculoskeletal pain in adults," Cochrane Database of Systematic Reviews 2015, Issue 6. Art. No. CD007402, 150 pages.
Dickel et al., "Standardized Tape Stripping: A Practical and Reproducible Protocol to Uniformly Reduce the Stratum Corneum," Skin Pharmacol Physiol 2010;23:259-265.
Dixon et al., "Ligand binding to the β-adrenergic receptor involves its rodopsin-like core," Nature, vol. 326, Mar. 5, 1987, 73-77.
Drosopoulos, "Roles of Asp54 and Asp213 in Ca2+ utilization by soluble human CD39/ecto-nucleotidase," Archives of Biochemistry and Biophysics 406 (2002) 85-95.
Ek et al., "Pathway across the blood-brain barrier," Nature, vol. 410, Mar. 22, 2001, pp. 430-431.
Elokely et al., "Fluorescence Spectrometric Determination of Drugs Containing α-Methylene Sulfone/Sulfonamide Functional Groups

(56) References Cited

OTHER PUBLICATIONS

Using N1-Methylnicotinamide Chloride as a Fluorogenic Agent," Hindawi Publishing Corporation, International Journal of Analytical Chemistry, vol. 2011, Article ID 840178, Mar. 14, 2011, 9 pages.
El-Serag et al., "Prevention of Complicated Ulcer Disease Among Chronic Users of Nonsteroidal Anti-inflammatory Drugs," Arch Intern Med/vol. 162, Oct. 14, 2002, pp. 2105-2110.
Erk et al., "Comparison of derivative spectrophotometric and liquid chromatographic methods for the determination of rofecoxib," Pharmazie. Jun. 2004;59(6):453-6.
Evans et al., "Effect of Low Dose Aspirin on Cardiorenal Function and Acute Hemodynamic Response to Enalaprilat in a Canine Model of Severe Heart Failure," JACC, vol. 25, No. 6, May 1995: 1445-1450.
Fanelli et al., "Cardiovascular and cerebrovascular risk with nonsteroidal anti-inflammatory drugs and cyclooxygenase 2 inhibitors: latest evidence and clinical implications," Ther Adv Drug Saf, 2017, vol. 8(6) 173-182.
Fillit, "The Role of Hormone Replacement Therapy in the Prevention of Alzheimer Disease," Arch Intern Med. 2002;162:1934-1942.
FitzGerald, "Parsing an enigma: the pharmacodynamics of aspirin resistance," The Lancet, vol. 361, Feb. 15, 2003, pp. 542-544.
Folts et al., "A Perspective on the Potential Problems With Aspirin as an Antithrombotic Agent: A Comparison of Studies in an Animal Model With Clinical Trials," J Am Coll Cardiol 1999;33:295-303.
Folzer et al., "Comparison of skin permeability for three diclofenac topical formulations: an in vitro study," Pharmazie 69: 27-31 (2014).
Friedman et al., "Understanding the role of prostaglandin E2 in regulating human platelet activity in health and disease," Thromb Res. Sep. 2015; 136(3): 493-503.
Garavito et al., "The Structure OfMammalian Cyclooxygenases," Annu. Rev. Biophys. Biomol. Struct. 2003. 32:183-206.
Garcia-Poza et al., "Risk of ischemic stroke associated with nonsteroidal antiinflammatory drugs and paracetamol: a population-based case-control study," Journal of Thrombosis and Haemostasis, 2015, 13: 708-718.
García Rodriguez et al., "Nonsteroidal Antiinflammatory Drugs as a Trigger of Clinical Heart Failure," Epidemiology 2003;14:240-246.
Graham, "NSAIDS, Helicobacter Pylori, and Pandora's Box," N Engl J Med, vol. 347, No. 26, Dec. 26, 2002, pp. 2162-2164.
Graham et al., "Ulcer Prevention in Long-term Users of Nonsteroidal Anti-inflammatory Drugs," Arch Intern Med. 2002;162:169-175.
Gregory et al., "An overview of animal models of pain: disease models and outcome measures," J Pain. Nov. 2013; 14(11), 26 pages.
Gunter et al., "Non-steroidal anti-inflammatory drug-induced cardiovascular adverse events: a meta-analysis," Journal of Clinical Pharmacy and Therapeutics, 2017, 42, 27-38.
Gupta et al., "Salts of Therapeutic Agents: Chemical, Physicochemical, and Biological Considerations," Molecules 2018, 23, 1719, 15 pages.
Guyatt et al., "Meta-Analyses of Therapies for Postmenopausal Osteoporosis," Endocrine Reviews, Aug. 2002, 23(4):496-507.
Guyatt et al., "Meta-Analysis of Alendronate for the Treatment of Postmenopausal Women," Endocrine Reviews, Aug. 2002, 23(4):508-516.
Guyatt et al., "Meta-Analysis of Risedronate for the Treatment of Postmenopausal Osteoporosis," Endocrine Reviews, Aug. 2002, 23(4):517-523.
Guyatt et al., "Meta-Analysis of Raloxifene for the Prevention and Treatment of Postmenopausal Osteoporosis," Endocrine Reviews, Aug. 2002, 23(4):524-528.
Guyatt et al., "Meta-Analysis of the Efficacy of Hormone Replacement Therapy in Treating and Preventing Osteoporosis in Postmenopausal Women," Endocrine Reviews, Aug. 2002, 23(4):529-539.
Guyatt et al., "Meta-Analysis of Calcitonin for the Treatment of Postmenopausal Osteoporosis," Endocrine Reviews, Aug. 2002, 23(4):540-551.
Guyatt et al., "Meta-Analysis of Calcium Supplementation for the Prevention of Postmenopausal Osteoporosis," Endocrine Reviews, Aug. 2002, 23(4):552-559.
Guyatt et al., "Meta-Analysis of the Efficacy of Vitamin D Treatment in Preventing Osteoporosis in Postmenopausal Women," Endocrine Reviews, Aug. 2002, 23(4):560-569.
Guyatt et al., "Summary of Meta-Analyses of Therapies for Postmenopausal Osteoporosis," Endocrine Reviews, Aug. 2002, 23(4):570-578.
Hadgraft et al., "Biotechnological Aspects of Transport Across Human Skin," Biotechnology and Genetic Engineering Reviews, 21:1, 183-196.
Hagen et al., "Skin penetration and tissue permeation after topical administration of diclofenac," Current Medical Research and Opinion, 2017, 33:9, 1623-1634.
Halpin et al., "The Absorption, Distribution, Metabolism and Excretion of Rofecoxib, a Potent and Selective Cyclooxygenase-2 Inhibitor, in Rats and Dogs," DMD 28:1244-1254, 2000.
Halpin et al., "The Disposition and Metabolism of Rofecoxib, a Potent and Selective Cyclooxygenase-2 Inhibitor, in Human Subjects," DMD 30:684-693, 2002.
Haltner-Ukomadu et al., "Hydrogel increases diclofenac skin permeation and absorption," Biopharm Drug Dispos. 2019;40:217-224.
Hamama et al., "Simultaneous Determination of Rofecoxib and Celecoxib in Human Plasma by High-Performance Liquid Chromatography," Journal of Chromatographic Science, vol. 43, Aug. 2005, 351-354.
Haq et al., "Strat-M® synthetic membrane: Permeability comparison to human cadaver skin," International Journal of Pharmaceutics 547 (2018) 432-437.
Hasler-Nguyen et al., "Evaluation of the in vitro skin permeation of antiviral drugs from penciclovir 1% cream and acyclovir 5% cream used to treat herpes simplex virus infection," BMC Dermatology 2009, 9:3, 10 pages.
Herkenne et al., "Pig Ear Skin ex Vivo as a Model for in Vivo Dermatopharmacokinetic Studies in Man," Pharmaceutical Research, vol. 23, No. 8, Aug. 2006, 1850-1856.
Herkenne et al., "Ibuprofen Transport into and through Skin from Topical Formulations: In Vitro-In Vivo Comparison," Journal of Investigative Dermatology (2007) 127, 135-142.
Hinz et al., "More Pronounced Inhibition of Cyclooxygenase 2, Increase in Blood Pressure, and Reduction of Heart Rate by Treatment With Diclofenac Compared With Celecoxib and Rofecoxib," Arthritis & Rheumatism, vol. 54, No. 1, Jan. 2006, pp. 282-291.
Hood et al., "Characterization of Celecoxib and Valdecoxib Binding to Cyclooxygenase," Mol Pharmacol 63:870-877, 2003.
Horton et al., "Intracellular Measurement of Prostaglandin E2: Effect of Anti-inflammatory Drugs on Cyclooxygenase Activity and Prostanoid Expression," Analytical Biochemistry 271, 18-28 (1999).
Hsieh et al., High-Throughput Liquid Chromatographic Determination of Rofecoxib in Human Plasma Using a Fully Automated On-Line Solid-Phase Extraction System, Journal of Liquid Chromatography & Related Technologies, 24:6, 799-812.
Hu et al., "Rapid access to 4-substituted-pyrones and 2(5H)-furanones via a palladiumcatalyzed CeOH bond activation," Tetrahedron 67 (2011) 7258e7262.
Huntjens et al., "Population pharmacokinetic modelling of the enterohepatic recirculation of diclofenac and rofecoxib in rats," British Journal of Pharmacology (2008) 153, 1072-1084.
International Search Report and Written Opinion dated Apr. 6, 2021, for International Application No. PCT/US2021/012769, 9 pages.
Jacintho et al., "Discovery of potent and selective PPARα/δ dual antagonists and initial biological studies," Bioorganic & Medicinal Chemistry Letters 29 (2019) 503-508.
Johnston et al., "Nonsteroidal anti-inflammatory drugs and corticosteroids for the management of canine osteoarthritis," Vet Clin North Am Small Anim Pract. Jul. 1997;27(4):841-62.
Kaneider et al., "Reversal of Thrombin-Induced Deactivation of CD39/ATPDase in Endothelial Cells by HMG-CoA Reductase Inhibition," Arterioscler Thromb Vase Biol. 2002;22:894-900.

(56) References Cited

OTHER PUBLICATIONS

Kang et al., "Cyclooxygenase-2 Gene Transcription in a Macrophage Model of Inflammation," The Journal of Immunology, 2006, 177: 8111-8122.

Katz, "The Impact of Pain Management on Quality of Life," J Pain Symptom Manage 2002;24:S38-S47.

Kesavanarayanan et al., "Topical dosage form of valdecoxib: Preparation and pharmacological evaluation," Acta Pharm. 57 (2007) 199-209.

Khan et al., "In vivo selectivity of a selective cyclooxygenase 2 inhibitor in the oral surgery model," Clin Pharmacol Ther 2002;72:44-9.

Kirchner et al., "Evaluation of the Antiinflammatory Activity of a Dual Cyclooxygenase-2 Selective/5-Lipoxygenase Inhibitor, RWJ 63556, in a Canine Model of Inflammation," JPET 282:1094-1101, 1997.

Kirkby et al., "Systematic study of constitutive cyclooxygenase-2 expression: Role of NF-κB and NFAT transcriptional pathways," PNAS, Jan. 12, 2016, vol. 113, No. 2, 434-439.

Kissinger et al., "A New Post-Column Photochemical Reactor for Liquid Chromatography," Current Separations 16:2 (1997), pp. 37-42.

Knijff-Dutmer et al., "Platelet function is inhibited by non-selective non-steroidal anti-inflammatory drugs but not by cyclo-oxygenase-2-selective inhibitors in patients with rheumatoid arthritis," Rheumatology 2002;41:458-461.

Kolasinski et al., "2019 American College of Rheumatology/Arthritis Foundation Guideline for the Management of Osteoarthritis of the Hand, Hip, and Knee," Arthritis & Rheumatology, vol. 0, No. 0, Month 2020, pp. 1-14.

Kole et al., "Recent advances in sample preparation techniques for effective bioanalytical methods," Biomed. Chromatogr. 2011; 25: 199-217.

Kolter et al., "Hot-Melt Extrusion with BASF Pharma Polymers," Extrusion Compendium 2nd Revised and Enlarged Edition, Oct. 2012, 201 pages.

Krekels et al., "Pharmacokinetic-Pharmacodynamic Modeling of the Inhibitory Effects of Naproxen on the Time-Courses of Inflammatory Pain, Fever, and the Ex Vivo Synthesis of TXB2 and PGE2 in Rats," Pharm Res (2011) 28:1561-1576.

Krishnaswami et al., "Dosing Celecoxib in Pediatric Patients With Juvenile Rheumatoid Arthritis," J Clin Pharmacol 2012;52:1134-1149.

Kusunoki et al., "Induction of Apoptosis in Rheumatoid Synovial Fibroblasts by Celecoxib, but Not by Other Selective Cyclooxygenase 2 Inhibitors," Arthritis & Rheumatism vol. 46, No. 12, Dec. 2002, pp. 3159-3167.

Laila et al., "An Improved HPLC method of Analysis of Rofecoxib," Indian Journal of Pharmaceutical Sciences, May-Jun. 2004, 338-340.

Lanas et al., "Risk of Upper and Lower Gastrointestinal Bleeding in Patients Taking Nonsteroidal Anti-inflammatory Drugs, Antiplatelet Agents, or Anticoagulants," Clinical Gastroenterology and Hepatology 2015;13:906-912.

Lang et al., "Impaired monocyte function in cancer patients: restoration with a cyclooxygenase-2 inhibitor," The FASEB Journal, vol. 17, Feb. 2003, pp. 286-288.

Lau et al., "Finite and Infinite Dosing," May 2017, 17 pages.

Leppert et al., "Transdermal and Topical Drug Administration in the Treatment of Pain," Molecules 2018, 23,681, 16 pages.

Li, "Presenilin-1 and Presenilin-2 exhibit distinct yet overlapping-secretase activities," JBC Papers in Press. Published on Apr. 8, 2003 as Manuscript M300974200, 29 pages.

Limjeerajarus et al., "Prolonged release of iloprost enhances pulpal blood flow and dentin bridge formation in a rat model of mechanical tooth pulp exposure," Journal of Oral Science, vol. 61, No. 1, 73-81, 2019.

Linton et al., "Cyclooxygenase-2 and atherosclerosis," Current Opinion in Lipidology 2002, 13:497-504.

Liu et al., "Stereoselective synthesis and anti-proliferative effects on prostate cancer evaluation of 5-substituted-3,4-diphenylfuran-2-ones," European Journal of Medicinal Chemistry 65 (2013) 323-336.

Loeser et al., "Pain: an overview," Lancet 1999; 353: 1607-09.

Long et al., "The effect of cyclooxygenase-2 inhibitors on spinal fusion," The Journal of Bone & Joint Surgery: Oct. 2002, vol. 84, Issue 10, pp. 1763-1768.

Lordan et al., "Phospholipids of Animal and Marine Origin: Structure, Function, and Anti-Inflammatory Properties," Molecules 2017, 22, 1964, 32 pages.

Lorrain et al., "Pharmacology of AM803, a novel selective five-lipoxygenase-activating protein (FLAP) inhibitor in rodent models of acute inflammation," European Journal of Pharmacology 640 (2010) 211-218.

MacDonald et al., "Effect of ibuprofen on cardioprotective effect of aspirin," Lancet 2003; 361: 573-74.

Mamdani et al., "Observational study of upper gastrointestinal haemorrhage in elderly patients given selective cyclooxygenase2 inhibitors or conventional nonsteroidal antiinflammatory drugs," BMJ, vol. 325, Sep. 21, 2002, 6 pages.

Marcus et al., "Cox Inhibitors and Thromboregulation," N Engl J Med, vol. 347, No. 13, Sep. 26, 2002.

Markenson, "The Demographics of Chronic Pain Management," J Pain Symptom Manage 2002;24:S10-S17.

Mashru et al., "Characterization of Solid Dispersions of Rofecoxib Using Differential Scanning Calorimeter," Journal of Thermal Analysis and Calorimetry, vol. 82 (2005) 167-170.

Mastbergen et al., "Selective COX-2 inhibition prevents proinflammatory cytokine-induced cartilage damage," Rheumatology 2002;41:801-808.

Mazenko et al., "Sample Preparation Via Solid Phase Extraction in the 96-Well Format for HPLC/UV Detection-Based Biofluid Assays. Application to the Determination of a Novel Cyclooxygenase II Inhibitor in Human Plasma and Urine," J. Liq. Chrom. & Rel. Technol., 24(17), 2601-2614 (2001).

McAdam et al., "Systemic biosynthesis of prostacyclin by cyclooxygenase (COX)-2: The human pharmacology of a selective inhibitor of COX-2," Proc. Natl. Acad. Sci. USA, vol. 96, pp. 272-277, Jan. 1999.

McGiff et al., "20-HETE and the kidney: resolution of old problems and new beginnings," the American Physiological Society, 1999, pp. R607-R623.

McPherson et al., "Topical NSAID Formulations," Pain Medicine 2013; 14: S35-S39.

McQuay, Opioids in pain management, Lancet 1999; 353: 2229-32.

Messmer et al., "A Selective Novel Peroxisome Proliferator-Activated Receptor (PPAR)-αAntagonist Induces Apoptosis and Inhibits Proliferation of CLL Cells In Vitro and In Vivo," Mol Med 21: 410-419, 2015.

Michaud et al., "Expression of Genes Related to Prostaglandin Synthesis or Signaling in Human Subcutaneous and Omental Adipose Tissue: Depot Differences and Modulation by Adipogenesis," Hindawi Publishing Corporation, Mediators of Inflammation, vol. 2014, Article ID 451620, 13 pages.

Miller et al., "CCR2 chemokine receptor signaling mediates pain in experimental osteoarthritis," PNAS, Dec. 11, 2012, vol. 109, No. 50, p. 20602-20607.

Morrison et al., "Analgesic Efficacy of the Cyclooxygenase-2-Specific Inhibitor Rofecoxib in Post-Dental Surgery Pain: A Randomized, Controlled Trial," Clinical Therapeutics, vol. 21, No. 6, 1999, pp. 943-953.

Morrison et al., "Rofecoxib, a Specific Cyclooxygenase-2 Inhibitor, in Primary Dysmenorrhea: A Randomized Controlled Trial," Obstet Gynecol 1999;94:504-8.

Mousa et al., "Intravenous and Oral Antithrombotic Efficacy of the Novel Platelet GPIIb/IIIa Antagonist Roxifiban (DMP754) and Its Free Acid Form, XV459," Arterioscler Thromb Vasc Biol. 1999;19:2535-2541.

Navas et al., "Determination of Celecoxib, Rofecoxib, Sodium Diclofenac and Niflumic Acid in Human Serum Samples by HPLC with DAD Detection," Chromatographia 2008, 67, Jan. (No. 1/2), 55-61.

(56) References Cited

OTHER PUBLICATIONS

Ng et al., "A Comparative Study of Transmembrane Diffusion and Permeation of Ibuprofen across Synthetic Membranes Using Franz Diffusion Cells," Pharmaceutics 2010, 2, 209-223.
Nicoll-Griffith et al., "Synthesis, Characterization, and Activity of Metabolites Derived from the Cyclooxygenase-2 Inhibitor Rofecoxib (MK-0966, VioxxTM)," Bioorganic & Medicinal Chemistry Letters 10 (2000) 2683-2686.
Nissen et al., "Cardiovascular Safety of Celecoxib, Naproxen, or Ibuprofen for Arthritis," N Engl J Med 2016;375:2519-29.
Ong et al., "An Evidence-Based Update on Nonsteroidal Anti-Inflammatory Drugs," Clinical Medicine & Research, 2007, vol. 5, No. 1: 19-34.
Orlando et al., "Crystal structure of rofecoxib bound to human cyclooxygenase-2," Acta Cryst. (2016). F72, 772-776.
Orlando et al., Supporting information for article: "Crystal structure of rofecoxib bound to human cyclooxygenase-2," Acta Cryst. (2016). F72.
Pavelka et al., "Glucosamine Sulfate Use and Delay of Progression of Knee Osteoarthritis," Arch Intern Med. 2002;162:2113-2123.
Parhi et al., "Transdermal Evaporation Drug Delivery System: Concept to Commercial Products," Adv Pharm Bull, 2018, 8(4), 535-550.
Park et al., "Bioactive sulfoximines: Syntheses and properties of Vioxxanalogs," Bioorganic & Medicinal Chemistry Letters 21 (2011) 4888-4890.
Pathan et al., "Chemical Penetration Enhancers for Transdermal Drug Delivery Systems," Tropical Journal of Pharmaceutical Research, Apr. 2009; 8 (2): 173-179.
Pelletier et al., "Osteoarthritis, an Inflammatory Disease," Arthritis & Rheumatism, vol. 44, No. 6, Jun. 2001, pp. 1237-1247.
Plummer et al., "Discovery of potent, selective, bioavailable phosphodiesterase 2 (PDE2) inhibitors active in an osteoarthritis pain model, Part I: Transformation of selective pyrazolodiazepinone phosphodiesterase 4 (PDE4) inhibitors into selective PDE2 inhibitors," Bioorganic & Medicinal Chemistry Letters 23 (2013) 3438-3442.
Pradal et al., "Importance of the formulation in the skin delivery of topical diclofenac: not all topical diclofenac formulations are the same," Journal of Pain Research 2019:12 1149-1154.
Prasit et al., The Discovery of Rofecoxib, [MK 966, VIOXX®, 4-(4'-Methylsulfonylphenyl)-3-Phenyl-2(5H)-Furanone], an Orally Active Cyclooxygenase-2 Inhibitor, Bioorganic & Medicinal Chemistry Letters 9 (1999) 1773-1778.
Rabbaa et al., "Bioequivalence Study and Pharmacokinetic Evaluation of Two Brands of Rofecoxib 25 mg Tablets in a Lebanese Population," The Journal of Applied Research, vol. 4, No. 4, 2004, 630-634.
Rahme et al., "Association Between Naproxen Use and Protection Against Acute Myocardial Infarction," Arch Intern Med. 2002; 162:1111-1115.
Rahme et al., "Use of NSAIDs, COX-2 Inhibitors, and Acetaminophen and Associated Coprescriptions of Gastroprotective Agents in an Elderly Population," Arthritis & Rheumatism (Arthritis Care & Research) vol. 47, No. 6, Dec. 15, 2002, pp. 595-602.
Ramakrishna et al., "Quantitation of Valdecoxib in human plasma by high-performance liquid chromatography with ultraviolet absorbance detection using liquid-liquid extraction," Journal of Chromatography B, 802 (2004) 271-275.
Ramakrishna et al., "High-performance liquid chromatography method for the quantification of entacapone in human plasma," Journal of Chromatography B, 823 (2005) 189-194.
Rao et al., "Development and validation of a reversed-phase liquid chromatographic method for separation and simultaneous determination of COX-2 inhibitors in pharmaceuticals and its application to biological fluids," Biomed. Chromatogr. 19: 362-368 (2005).
Rao et al., "An overview of the recent developments in analytical methodologies for determination of COX-2 inhibitors in bulk drugs, pharmaceuticals and biological matrices," Journal of Pharmaceutical and Biomedical Analysis 39 (2005) 349-363.

Raval et al., "Influence of solvents on the crystal habit and properties of rofecoxib and celecoxib: No evidence of polymorphism," Journal of Pharmaceutical Negative Results, Oct. 2010, vol. 1, Issue 2, pp. 40-50.
Ray et al., "COX-2 selective non-steroidal anti-inflammatory drugs and risk of serious coronary heart disease," Lancet 2002; 360: 1071-73.
Ray et al., "Non-steroidal anti-inflammatory drugs and risk of serious coronary heart disease: an observational cohort study," Lancet 2002; 359: 118-23.
Robson, "Editorials, The dangers of NSAIDs:look both ways," British Journal of General Practice, Apr. 2016, pp. 172-173.
Rose et al., "Determination of celecoxib in human plasma by normal-phase high-performance liquid chromatography with column switching and ultraviolet absorbance detection," Journal of Chromatography B, 738 (2000) 377-385.
Rossat et al., "Renal effects of selective cyclooxygenase-2 inhibition in normotensive salt-depleted subjects," Clin Pharmacol Ther 1999;66:76-84.
Rouzer et al., "Characterization of Cloned Human Leukocyte 5-Lipozygenase Expressed in Mammalian Cells," The Journal of Biological Chemistry, vol. 263, No. 21, Issue of Jul. 25, pp. 10135-10140, 1988.
Ruela et al., "Evaluation of skin absorption of drugs from topical and transdermal formulations," Brazilian Journal of Pharmaceutical Sciences, vol. 52, n. 3, Jul./Sep. 2016, pp. 527-544.
Salamanca et al., "Franz Diffusion Cell Approach for Pre-Formulation Characterisation of Ketoprofen Semi-Solid Dosage Forms," Pharmaceutics 2018, 10, 148.
Samad et al., "Interleukin-1β-mediated induction of Cox-2 in the CNS contributes to inflammatory pain hypersensitivity," Nature, vol. 410, Mar. 22, 2001, pp. 471-475.
Sammour et al., "Formulation and Optimization of Mouth Dissolve Tablets Containing Rofecoxib Solid Dispersion," AAPS PharmSciTech 2006; 7 (2) Article 55, pp. E1-E9.
Sanna et al., "Effect of Vehicle on Diclofenac Sodium Permeation from New Topical Formulations: In Vitro and In Vivo Studies," Current Drug Delivery, 2009, 6, 93-100.
Santilli et al., "The Coxib case: Are EP receptors really guilty?," Atherosclerosis 249 (2016) 164-173.
Santovito et al., "Cyclooxygenase and prostaglandin synthases: roles in plaque stability and instability in humans," Current Opinion in Lipidology 2009, 20:402-408.
Sattari et al., "High Performance Liquid Chromatographic Determination of Cyclooxygenase II Inhibitor Rofecoxib in Rat and Human Plasma," J Pharm Pharmaceut Sci, 3(3): 312-316, 2000.
Savaşer et al., "RP-HPLC Assay of Rofecoxib from Pharmaceutical Dosage Forms and Human Plasma and Its Drug Dissolution Studies," Analytical Letters, vol. 37, No. 1, pp. 81-97, 2004.
Saunders et al., "Selective Suppression of CCAAT/Enhancer-binding Protein β Binding and Cyclooxygenase-2 Promoter Activity by Sodium Salicylate in Quiescent Human Fibroblasts," The Journal of Biological Chemistry, vol. 276, No. 22, Issue of Jun. 1, pp. 18897-18904, 2001.
Schebb et al., "Development of an ultra fast online-solid phase extraction (SPE) liquid chromatography electrospray tandem mass spectrometry (LC-ESI-MS/MS) based approach for the determination of drugs in pharmacokinetic studies," Anal Methods. Jan. 1, 2011; 3(2): 420-428.
Schieving, "The Seven Most Common Grades for Chemicals and Reagents," Lab Manager, Nov. 13, 2017, 3 pages.
Schink et al., "Risk of ischemic stroke and the use of individual non-steroidal anti-inflammatory drugs: A multi-country European database study within the SOS Project," PLoS ONE 13(9) Sep. 19, 2018, 14 pages.
Schumacher Jr. et al., "Randomised double blind trial of etoricoxib and indometacin in treatment of acute gouty arthritis," BMJ 2002;324:1488-92.
Schwartz et al., "Comparison of rofecoxib, celecoxib, and naproxen on renal function in elderly subjects receiving a normal-salt diet," Clin Pharmacol Ther 2002;72:50-61.

(56) References Cited

OTHER PUBLICATIONS

Seta et al., "Renal and cardiovascular characterization of COX-2 knockdown mice," Am J Physiol Regul Integr Comp Physiol 296: R1751-R1760, 2009.

Shaya et al., "Selective Cyclooxygenase-2 Inhibition and Cardiovascular Effects," Arch Intern Med. 2005;165:181-186.

Shehata et al., "Derivative spectrophotometric and fluorimetric methods for determination of rofecoxib in tablets and in human plasma in presence of its photo-degradation product," Il Farmaco 59 (2004) 139-145.

Silverstein et al., "Gastrointestinal Toxicity With Celecoxib vs Nonsteroidal Anti-inflammatory Drugs for Osteoarthritis and Rheumatoid Arthritis," JAMA, Sep. 13, 2000—vol. 284, No. 10, pp. 1247-1255.

Simon et al., "Comparative evaluation of rivastigmine permeation from a transdermal system in the Franz cell using synthetic membranes and pig ear skin with in vivo-in vitro correlation," International Journal of Pharmaceutics 512 (2016) 234-241.

Sinatra, "Role of COX-2 Inhibitors in the Evolution of Acute Pain Management," J Pain Symptom Manage 2002;24:S18-S27.

Slørdal et al., Letters to the Editors, "A life-threatening interaction between lithium and celecoxib," Br J Clin Pharmacol, 2003, 55, 413-414.

Solomon et al., "Nonsteroidal Anti-inflammatory Drug Use and Acute Myocardial Infarction," Arch Intern Med. 2002;162:1099-1104.

Soloviev et al., "Whole Blood Platelet Aggregation in Humans and Animals: A Comparative Study," Journal of Surgical Research 82, 180-187 (1999).

Song et al., "Cyclooxygenase-2, Player or Spectator in Cyclooxygenase-2 Inhibitor-Induced Apoptosis in Prostate Cancer Cells," Journal of the National Cancer Institute, vol. 94, No. 8, Apr. 17, 2002, pp. 585-591.

Soriano et al., "Incidence of Upper and Lower Gastrointestinal Bleeding in New Users of Low-dose Aspirin," Clinical Gastroenterology and Hepatology (2018), doi: 10.1016/j.cgh.2018.05.061, 39 pages.

Staats, "Pain Management and Beyond: Evolving Concepts and Treatments Involving Cyclooxygenase Inhibition," J Pain Symptom Manage 2002;24:S4-S9.

Stanos, "Osteoarthritis Guidelines: A Progressive Role for Topical NSAIDs," The Journal of the American Osteopathic Association, Feb. 2013, vol. 113, No. 2, pp. 123-127.

Stebbins et al., "In vitro and in vivo pharmacology of NXT629, a novel and selective PPARα antagonist," European Journal of Pharmacology 809 (2017) 130-140.

Stichtenoth et al., "The Second Generation of COX-2 Inhibitors," Drugs 2003; 63 (1): 33-45.

Stock et al., "5-Lipoxygenase-Activating Protein (FLAP) Inhibitors. Part 4: Development of 3-[3-tert-Butylsulfanyl-1-[4-(6-ethoxypyridin-3-yl)benzyl]-5-(5-methylpyridin-2-lmethoxy)-1H-indol-2-yl]-2,2-dimethylpropionic Acid (AM803), a Potent, Oral, Once Daily FLAP Inhibitor," J. Med. Chem. 2011, 54, 8013-8029.

Strader et al., "The Carboxyl Terminus of the Hamster β-Adrenergic Receptor Expressed in Mouse L Cells Is Not Required for Receptor Sequestration," Cell, vol. 49, 855-863, Jun. 19, 1987.

Terkeltaub et al., "Invited review: the mitochondrion in osteoarthritis," Mitochondrion 1 (2002) 301-319.

Thal et al., "A Randomized, Double-Blind, Study of Rofecoxib in Patients with Mild Cognitive Impairment," Neuropsychopharmacology (2005) 30, 1204-1215.

Therien et al., "Synthesis of Rofecoxib, (MK 0966, Vioxx® 4-(4'-Methylsulfonylphenyl)-3-Phenyl-2(5H)-Furanone), a Selective and Orally Active Inhibitor of Cyclooxygenase-2," Synthesis 2001, No. 12, 1778-1779.

Thomas et al., "The transdermal revolution," Drug Discovery Today, vol. 9, Issue 16, Aug. 2004, pp. 697-703.

Tietz et al., "Radiotracers for molecular imaging of cyclooxygenase-2 (COX-2) enzyme," Curr Med Chem. 2013;20(35):4350-69.

Todo, "Transdermal Permeation of Drugs in Various Animal Species," Pharmaceutics 2017, 9, 33, 11 pages.

Turk et al., "Assessment of patients' reporting of pain: an integrated perspective," Lancet 1999; 353: 1784-88.

Van Baar et al., "Effectiveness of Exercise Therapy in Patients With Osteoarthritis of the Hip or Knee," Arthritis & Rheumatism vol. 42, No. 7, Jul. 1999, pp. 1361-1369.

Vallano et al., "Monolithic silica liquid chromatography columns for the determination of cyclooxygenase II inhibitors in human plasma," Journal of Chromatography B, 779 (2002) 249-257.

Varga et al., "Cardiovascular Risk of Nonsteroidal Anti-Inflammatory Drugs: An Under-Recognized Public Health Issue," Cureus 9(4): e1144, 2017, 12 pages.

Vignola et al., "Transcriptional regulation of COX-2: a key mechanism in the pathogenesis of nasal polyposis in aspirin-sensitive asthmatics?" Allergy 2003: 58: 95-97.

Wang et al., "Molecular simulation study on concentration effects of rofecoxib with POPC bilayer," Journal of Molecular Graphics and Modelling 70 (2016) 94-99.

Ware, "SF-36 Health Survey Update," SPINE, 2000, vol. 25, No. 24, pp. 3130-3139.

Warner et al., "Nonsteroid drug selectivities for cyclo-oxygenase-1 rather than cyclo-oxygenase-2 are associated with human gastrointestinal toxicity: A full in vitro analysis," Proc. Natl. Acad. Sci. USA, vol. 96, pp. 7563-7568, Jun. 1999.

Warner et al., "Cyclooxygenase-3 (COX-3): Filling in the gaps toward a COX continuum?," PNAS, Oct. 15, 2002, vol. 99, No. 21, pp. 13371-13373.

Watson et al., "Lower Risk of Thromboembolic Cardiovascular Events With Naproxen Among Patients With Rheumatoid Arthritis," Arch Intern Med. 2002;162:1105-1110.

Weinblatt et al., "Adalimumab, a Fully Human Anti-Tumor Necrosis Factor α Monoclonal Antibody, for the Treatment of Rheumatoid Arthritis in Patients Taking Concomitant Methotrexate," Arthritis & Rheumatism, vol. 48, No. 1, Jan. 2003, pp. 35-45.

Werner et al., "Selective and rapid liquid chromatography-mass spectrometry method for the quantification of rofecoxib in pharmacokinetic studies with humans," Journal of Chromatography B, 760 (2001) 83-90.

Whitstock, "Manufacturing the truth: From designing clinical trials to publishing trial data," Indian J Med Ethics. Apr.-Jun. 2018;3(2) NS:152-62.

Woolf et al., "Determination of rofecoxib, a cyclooxygenase-2 specific inhibitor, in human plasma using high-performance liquid chromatography with post-column photochemical derivatization and fluorescence detection," Journal of Chromatography B, 730 (1999) 221-227.

Woolf et al., "Neuropathic pain: aetiology, symptoms, mechanisms, and management," Lancet 1999; 353: 1959-64.

Wu et al., "Transcriptional Control of COX-2 via C/EBPb," Arterioscler Thromb Vasc Biol. 2005;25:679-685.

Wu et al., "Regulation of cyclooxygenase-2 expression by cAMP response element and mRNA stability in a human airway epithelial cell line exposed to zinc," Toxicology and Applied Pharmacology 231 (2008) 260-266.

Xia et al., "GABA Increases Stimulus Selectivity of Neurons in Primary Visual Cortices of Cats Chronically Treated With Morphine," Neuroscience 241 (2013) 116-125.

Xu et al., "Suppression of inducible cyclooxygenase 2 gene transcription by aspirin and sodium salicylate," Proc. Natl. Acad. Sci. USA, vol. 96, pp. 5292-5297, Apr. 1999.

Yagihashi et al., "Mechanism of diabetic neuropathy: Where are we now and where to go?," Journal of Diabetes Investigation, vol. 2, Issue 1, Feb. 2011, pp. 18-32.

Yamakawa et al., "Structure-activity relationship of celecoxib and rofecoxib for the membrane permeabilizing activity," Bioorganic & Medicinal Chemistry 22 (2014) 2529-2534.

Yokouchi et al., "Revisiting the role of COX-2 inhibitor for non-small cell lung cancer," Transl Lung Cancer Res 2015;4(5):660-664.

Yu et al., "Vascular COX-2 Modulates Blood Pressure and Thrombosis in Mice," Sci Transl Med 4, 132ra54 (2012), 8 pages.

Yu et al., "Vascular COX-2 Modulates Blood Pressure and Thrombosis in Mice," Sci Transl Med. May 2, 2012; 4(132), 15 pages.

(56) References Cited

OTHER PUBLICATIONS

Yu et al., "Topical skin targeting effect of penetration modifiers on hairless mouse skin, pig abdominal skin and pig ear skin," Drug Delivery, 2015; 22(8): 1053-1058.

Zeng et al., "Relative efficacy and safety of topical non-steroidal anti-inflammatory drugs for osteoarthritis: a systematic review and network meta-analysis of randomised controlled trials and observational studies," Br J Sports Med 2018;52:642-650.

Zhang et al., "Determination of rofecoxib in human plasma and breast milk by high-performance liquid chromatographic assay," Journal of Chromatography B, 807 (2004) 217-221.

* cited by examiner

TOPICAL COMPOSITIONS CONTAINING ROFECOXIB AND METHODS OF MAKING AND USING THE SAME

CROSS-REFERENCE TO RELATED APPLICATIONS

This application is a continuation of International Application No. PCT/US2021/012769, filed Jan. 8, 2021, which claims priority to U.S. Provisional Application No. 62/959,624, filed Jan. 10, 2020. Each of the aforementioned applications is incorporated by reference herein in its entirety for all purposes.

FIELD

The disclosure relates to topical compositions containing rofecoxib. The disclosure further relates to methods of applying topical compositions containing rofecoxib to the skin to alleviate inflammation and pain.

BACKGROUND OF THE INVENTION

Oral non-steroidal anti-inflammatory drugs (NSAIDs) are a mainstay in the management of inflammatory diseases, including arthritis, bursitis, and tendonitis. NSAIDS exert analgesic, anti-inflammatory and antipyretic effects through inhibition of the cyclooxygenase enzymes, COX-1 and COX-2. NSAIDS are used to reduce pain and inflammation. NSAIDS are however associated with serious potential side effects including nausea, vomiting, peptic ulcer disease, gastrointestinal bleeding, and cardiovascular events. The side effects of NSAIDS led to the development of selective cyclooxygenase-2 (COX-2) inhibitors. Although COX-2 inhibitors reduce the risk of gastrointestinal bleeding, COX-2 inhibitors are still associated with cardiovascular events. The selective COX-2 inhibitor rofecoxib exhibits a greater therapeutic efficacy for treating pain than celecoxib and acetaminophen. However, rofecoxib was withdrawn from the market due to an increased risk of cardiac toxicity associated with long-term use. Therefore, there remains a need in the art for the development of alternative NSAID formulations that effectively treat inflammation and exhibit fewer side effects.

SUMMARY OF THE INVENTION

Topical compositions containing rofecoxib and methods of making and using the same are described herein. The rofecoxib topical compositions described herein exhibit a reduced risk of cardiac toxicity compared to oral rofecoxib formulations.

In some embodiments, a topical composition comprising a therapeutically effective amount of rofecoxib dissolved in a solvent system comprising one or more pharmaceutically acceptable solvents is provided.

In some embodiments, the pharmaceutically acceptable solvent system of the topical compositions comprising a therapeutically effective amount of rofecoxib described herein comprise one or more pharmaceutically acceptable solvents selected from the group consisting of acetone (AC), 2-methylpentane-2,4-diol (M24D), alpha-terpineol (AT), benzyl alcohol (BA), diethyl sebacate (DS), diethylene glycol monoethyl ether (DGME), diisopropyl adipate (DIA), dimethyl sulfoxide (DMSO), ethyl acetate (EA), isopropyl tetradecanoate (IPTD, also called isopropyl tetradecanoate), N-methyl-2-pyrrolidone (MP), polyethylene glycol 400 (PEG), polysorbate 20 (PS20), polysorbate 80 (PS80), propylene glycol diacetate (PGD), propylene glycol (PPG), isosorbide dimethyl ether, and propylene carbonate.

In some embodiments, the topical compositions comprising a therapeutically effective amount of rofecoxib comprise a pharmaceutically acceptable solvent system comprising isosorbide dimethyl ether (DI) and propylene carbonate (PC).

In some embodiments, the topical compositions comprising a therapeutically effective amount of rofecoxib comprise a pharmaceutically acceptable solvent system comprising isosorbide dimethyl ether (DI), propylene carbonate (PC), and DMSO.

In some embodiments, the topical compositions comprising a therapeutically effective amount of rofecoxib comprise a pharmaceutically acceptable solvent system comprising from about 10% w/w DI to about 20% w/w DI and from about 3% w/w PC to about 8% w/w PC.

In some embodiments, the topical compositions comprising a therapeutically effective amount of rofecoxib comprise a pharmaceutically acceptable solvent system comprising about 15% w/w DI and about 5 w/w PC.

In some embodiments, the topical compositions comprising a therapeutically effective amount of rofecoxib comprise a pharmaceutically acceptable solvent system comprising DI, PC, and BA.

In some embodiments, the topical compositions comprising a therapeutically effective amount of rofecoxib comprise a pharmaceutically acceptable solvent system comprising DI, PC, and DMSO.

In some embodiments, the topical compositions comprising a therapeutically effective amount of rofecoxib comprise a pharmaceutically acceptable solvent system comprising DI, PC, DIA.

In some embodiments, the topical compositions comprising a therapeutically effective amount of rofecoxib comprise a pharmaceutically acceptable solvent system comprising DI, PC, PS20.

In some embodiments, the topical compositions comprise a therapeutically effective amount of rofecoxib comprise a pharmaceutically acceptable solvent system comprising DI, PC, BA, DMSO, DIA, and PS20.

In some embodiments, the topical compositions comprise a therapeutically effective amount of rofecoxib comprise a pharmaceutically acceptable solvent system comprising about 15% w/w DI, about 5% w/w PC, about 3% w/w BA, about 20% w/w DMSO, about 12% w/w DIA, and about 15% w/w PS20.

In some embodiments, the topical compositions comprise a therapeutically effective amount of rofecoxib, wherein the therapeutically acceptable amount of rofecoxib is up to 5% w/w.

In some embodiments, the topical compositions described herein comprising a therapeutically effective amount of rofecoxib and a pharmaceutically acceptable solvent system, comprise one or more additional ingredients selected from the group consisting of a humectant, a chelating agent, a UV absorption agent, a moisturizing agent, an excipient, a preservative, a thickening agent, a silicone containing compound, an essential oil, a structuring agent, a vitamin, a pharmaceutical ingredient, and an antioxidant.

In some embodiments, the topical compositions comprise a therapeutically effective amount of rofecoxib, a pharmaceutically acceptable solvent system, and oleic acid.

In some embodiments, methods of applying a topical composition comprising a therapeutically effective amount of rofecoxib and a pharmaceutically acceptable solvent to the skin comprising topically comprising the aforementioned composition are provided.

In some embodiments, a method of reducing inflammation, comprising topically applying the topical composition comprising a therapeutically effective amount of a topical composition comprising rofecoxib and a pharmaceutically acceptable solvent is provided.

In some embodiments, a method of treating arthritis comprising topically applying the topical composition comprising a therapeutically effective amount of a topical composition comprising rofecoxib and a pharmaceutically acceptable solvent is provided.

In some embodiments, a method of treating acute pain, comprising topically applying the topical composition comprising a therapeutically effective amount of a topical composition comprising rofecoxib and a pharmaceutically acceptable solvent is provided.

In some embodiments, a method of treating migraines, comprising topically applying the topical composition comprising a therapeutically effective amount of a topical composition comprising rofecoxib and a pharmaceutically acceptable solvent is provided.

In some embodiments, provided herein is a rofecoxib topical composition selected from Formulations 1-77, 80, 82, 83, and 85-93.

In some embodiments, provided herein is a rofecoxib topical composition comprising Formulation 85.

DETAILED DESCRIPTION OF THE INVENTION

Definitions

Figure 1:
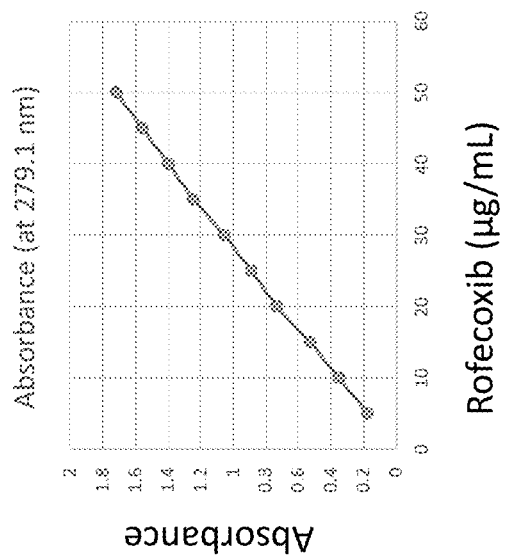
FIG. 1 shows the calculation of the rofecoxib extinction coefficient.

As used herein, the verb "comprise" is used in this description and in the claims and its conjugations are used in its non-limiting sense to mean that items following the word are included, but items not specifically mentioned are not excluded.

As used herein, the term "about" refers to plus or minus 10% of the referenced number unless otherwise stated or otherwise evident by the context, and except where such a range would exceed 100% of a possible value, or fall below 0% of a possible value, such as less than 0% content of an ingredient, or more than 100% of the total contents of a composition. For example, reference to an absolute content of rofecoxib of "about 1% w/w" means that rofecoxib can be present at any amount ranging from 0.9% to 1.1% content by weight.

The term "a" or "an" refers to one or more of that entity; for example, "a solvent" refers to one or more solvents or at least one solvent. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, the term "skin" refers to any of the layers of the skin, including the epidermis, dermis, and hypodermis. The epidermis has five sub-layers, including the stratum corneum, stratum lucidum, stratum granulosum, stratum spinosum, and stratum basale, which are listed from the outermost sub-layer to the innermost sub-layer. For example, the stratum corneum is the skin's surface.

As used herein, the term "topical composition" refers to any formulation that is applied to the skin.

As used herein, "treat" or "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

Various concentration expressions, including volume concentrations, weight concentrations, and mass concentrations, are utilized to describe the percentage of a component in a solution. Volume concentration has units of % v/v, where v/v is volume per volume. If a solution contains 5% v/v of a component, 5 mL of the component is in a total solution of 100 mL. Weight concentration of a solution is expressed as % w/w, where w/w is weight per weight. If a solution contains 30% w/w of sodium chloride, the solution contains 30 g of sodium chloride and 70 g of solvent. Mass concentration of a solution is expressed as % w/v, where w/v is weight per volume. If 1 g of sodium chloride is dissolved in a solution with a total volume of 100 mL, a 1% w/v sodium chloride solution has been made.

As defined herein, "topical application" is application of a composition to the skin.

As used herein, the term "solvent system" refers to one or more solvents used to solubilize rofecoxib.

As defined herein, the term "pharmaceutically acceptable solvent" refers to a solvent that is not toxic or harmful to a subject.

Topical Compositions Containing Rofecoxib

In some embodiments, the disclosure provides rofecoxib topical compositions. Rofecoxib topical compositions contain rofecoxib, a solvent system, and optionally contain additional ingredients and/or a vehicle, which are described below. In some embodiments, the rofecoxib topical compositions are applied topically to the skin. In some embodiments, application of rofecoxib topical compositions alleviate inflammation and/or pain.

Rofecoxib

Rofecoxib is a nonsteroidal anti-inflammatory drug (NSAID). NSAIDs are the most commonly used drugs in inflammatory diseases. NSAIDS, such as aspirin, ibuprofen, and indomethacin, exert their effects through inhibition of the COX-1 and COX-2 isoforms of cyclooxygenase. NSAIDS also are associated with a number of side effects, including gastrointestinal toxicity, which is primarily dependent on COX-1 inhibition. Rofecoxib is a selective inhibitor of cyclooxygenase-2 (COX-2). Similar to NSAIDS which inhibit both COX-1 and COX-2, selective inhibitors of COX-2 relieve inflammation and pain, but unlike NSAIDS that inhibit both COX-1 and COX-2, selective inhibitors of COX-2 are associated with a reduced number of adverse gastrointestinal toxicities.

All NSAIDS inhibit COX-2 to reduce inflammation. Serious adverse events of both COX-2 selective (e.g. celecoxib and rofecoxib) and non-selective COX-1 and COX-2 NSAIDS (e.g. ibuprofen, diclofenac, and naproxen) is hypertension and cardiovascular events. COX-2 is responsible for these serious adverse effects. Because COX-2 regulates the balance of salt in the kidneys, inhibition of COX-2 can cause hypertension. COX-2 also creates prostacyclin which is a blood thinner and lower levels of this cytokine are associated with cardiovascular events. Therefore, the side effects of both selective and non-selective NSAIDs are the same and all have a similar cardiovascular profile. However, as noted COX-1 inhibition causes perforations, ulcers, and bleeds in the gastrointestinal tract, which led to the initiation of COX-2 inhibitor development.

The first long term trials that showed the cardiovascular risk was the APPROVe trial (Adenomatous Polyp Prevention on Vioxx) by Merck and the APC (Adenoma Prevention with Celecoxib) trial by Pfizer. As such, although rofecoxib was approved by the Food and Drug Administration (FDA) in 1999 as an oral formulation for the treatment of osteoarthritis, rheumatoid arthritis, acute pain, primary dysmenorrhea, and migraines, rofecoxib was withdrawn from the market in 2004 by Merck due to the side effects first conclusively seen in the APPROVe Trial. Pfizer had the same results in its APC trial but left celecoxib on the market with a Black Box warning. However, all NSAIDs carry the same cardiovascular risks and the FDA has placed a Black Box warning on all NSAIDs including over the counter NSAIDs, e.g., ibuprofen, diclofenac and naproxen. Rofecoxib remains an FDA approved drug listed as "discontinued" in the Orange Book.

In some embodiments, the present disclosure provides topical rofecoxib formulations. In some embodiments, the topical rofecoxib formulations of the disclosure reduce the risk of adverse cardiovascular events. In some embodiments, the topical rofecoxib formulations of the disclosure reduce the risk of hypertension. Without being bound by theory, rofecoxib topical formulations exhibit a reduced effect of adverse cardiovascular events, because in comparison to oral formulations, rofecoxib topical formulations result in less systemic absorption of rofecoxib.

In some embodiments, a therapeutically acceptable amount of rofecoxib is incorporated in the topical compositions described herein. As used herein, a therapeutically acceptable amount is an amount of rofecoxib that is efficacious, but exhibits fewer side effects than a similar oral composition. In some embodiments, the therapeutically acceptable amount of rofecoxib in the compositions of the present disclosure is up to 10% w/w. In some embodiments, the therapeutically acceptable amount of rofecoxib is up to 5% w/w. In some embodiments, the therapeutically acceptable amount of rofecoxib is about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3.0% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4.0% w/w, about 4.1% w/w, about 4.2% w/w, about 4.3% w/w, about 4.4% w/w, about 4.5 w/w, about 4.6% w/w, about 4.7% w/w, about 4.8% w/w, about 4.9% w/w, about 5.0% w/w, about 5.1% w/w, about 5.2 w/w, about 5.3 w/w, about 5.4 w/w, about 5.5 w/w, about 5.6 w/w, about 5.7 w/w, about 5.8 w/w, about 5.9 w/w, about 6.0% w/w, about 6.1% w/w, about 6.2% w/w, about 6.3% w/w, about 6.4% w/w, about 6.5 w/w, about 6.5% w/w/, about 6.6% w/w, about 6.7% w/w, about 6.8% w/w, about 6.9% w/w, about 7.0% w/w, about 7.1% w/w, about 7.2% w/w, about 7.3% w/w, about 7.4% w/w, about 7.5 w/w, about 7.6% w/w, about 7.7% w/w, about 7.8% w/w, about 7.9% w/w, about 8.0% w/w, about 8.1% w/w, about 8.2% w/w, about 8.3% w/w, about 8.4% w/w, about 8.5 w/w, about 8.6% w/w, about 8.7% w/w, about 8.8% w/w, about 8.9% w/w, about 9.0% w/w, about 9.1% w/w, about 9.2% w/w, about 9.3% w/w, about 9.4% w/w, about 9.5 w/w, about 9.6% w/w, about 9.7% w/w, about 9.8% w/w, about 9.9% w/w, or about 10.0% w/w. In some embodiments, the therapeutically acceptable amount of rofecoxib is about 1.0% w/w. In some embodiments, the therapeutically acceptable amount of rofecoxib is about 2.0% w/w. In some embodiments, the therapeutically acceptable amount of rofecoxib is about 3.0% w/w.

Solvent Systems for Dissolving Rofecoxib

In some embodiments, the topical rofecoxib compositions described herein contain a solvent system. In some embodiments, the solvent system is utilized to solubilize rofecoxib. In some embodiments, rofecoxib is at least 80% dissolved in the solvent systems described throughout the disclosure. In some embodiments, rofecoxib is about 80% dissolved, or about 81% dissolved, or about 82% dissolved, or about 83% dissolved, or about 84% dissolved, or about 85% dissolved, or about 86% dissolved, or about 87% dissolved, or about 88% dissolved, or about 89% dissolved, or about 90% dissolved, or about 91% dissolved, or about 92% dissolved, or about 93% dissolved, or about 94% dissolved, or about 95% dissolved, or about 96% dissolved, or about 97% dissolved, or about 98% dissolved, or about 99% dissolved, or about 100% dissolved when placed in the solvent system. In some embodiments, rofecoxib is saturated in the solvent systems described herein. In some embodiments, rofecoxib is unsaturated in the solvent systems described herein. In some embodiments, rofecoxib is supersaturated in the solvent systems described herein.

In some embodiments, the solvent system contains pharmaceutically acceptable solvents. In order for a drug, e.g. rofecoxib, to penetrate epithelial tissue upon topical application, the drug must be in solution in the formulation. The development of a solvent system that solubilizes rofecoxib is difficult, because rofecoxib is insoluble in water and many common organic solvents.

Furthermore, an optimal solvent system not only solubilizes rofecoxib, but minimizes the use of potentially toxic solvents. In some embodiments, the solvent systems provided herein for dissolving rofecoxib follow the International Council for Harmonization of Technical Requirements for Pharmaceuticals for Human Use (ICH) guidance for industry, *Q3C Impurities: Residual Solvents*, which makes recommendations as to what amounts of residual solvents are considered safe in pharmaceuticals. The *Q3C Impurities: Residual Solvents* guidelines are incorporated by reference in their entirety herein. U.S. Department of Health and Human Services, Food and Drug Administration. (2017). Q3C Impurities: Residual Solvents.

In some embodiments, the concentration of rofecoxib dissolved in a given solvent system is used to determine the efficacy of the solvent system for solubilizing rofecoxib. In some embodiments, the concentration of rofecoxib dissolved in solution is identified using methods known to a person of skill in the art. In some embodiments, the concentration of rofecoxib is determined using a method selected from the group consisting of mass spectrometry, liquid chromatography, ultraviolet spectrophotometry, high performance liquid chromatography, ultraviolet-visible (UV-visible) absorption spectroscopy, and immunoassay. Erk et al. describes the determination of rofecoxib concentration by ultraviolet spectrophotometry and is incorporated by reference in its entirety herein: Erk et al. Pharmazie. 2004 June; 59(6):453-6.

In some embodiments, the solvent systems described herein contain solvents that work through a synergistic effect to dissolve rofecoxib. A synergistic effect results when the total solubility of rofecoxib in two or more solvents is greater than the sum of the solubilities of rofecoxib in the individual solvents. Non-limiting examples of solvents used in the solvent systems described herein include acetone (AC), 2-methylpentane-2,4-diol (M24D), alpha-terpineol (AT), benzyl alcohol (BA), diethyl sebacate (DS), diethylene glycol monoethyl ether (DGME), diisopropyl adipate (DIA), isosorbide dimethyl ether (DI), dimethyl sulfoxide (DMSO), ethyl acetate (EA), isopropyl tetradecanoate (IPTD), N-methyl-2-pyrrolidone (MP), oleic acid (OA), polyethylene glycol 400 (PEG), polysorbate 20 (PS20), polysorbate 80 (PS80), propylene carbonate (PC), propylene glycol diacetate (PGD), propylene glycol (PPG), acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, formamide, hexane, methanol, ethanol, 2-methoxyethanol, methylbutylketone, methylcyclohexane, nitromethane, pyridine, sulfolane, tetraline, toluene, 1,1,2-trichloroethylene, xylene, and lanoline (X). In some embodiments, the solvent system comprises one or more of 2-pyrrolidone, 2-piperidone, ε-caprolactam, N-alkylpyrrolidone, N-hydroxyalkylpyrrolidone, N-alkylpiperidone, N-alkylcaprolactam, polyvinylpyrrolidone; ε-caprolactone and isomers thereof, δ-valerolactone and isomers thereof, β-butyrolactone and isomers thereof, dimethyl isosorbide, isosorbide dimethyl ether, N-methyl pyrrolidone, and combinations thereof.

In some embodiments, the solvent system comprises one or more solvents comprising a heterocyclic ring. In some embodiments, the solvent system comprises one or more bicyclic solvents. In some embodiments, the heterocyclic ring is a furan, a tetrahydrofuran, a thiophene, pyrrole, pyrrolidine, pyran, piperidine, imidazole, thiazole, dioxane, morpholine, pyrimidine, or a combination thereof. In some embodiments, the solvent system comprises one or more solvents comprising an oxygen containing heterocycle. In some embodiments, the solvent system comprises one or more bicyclic solvents. In some embodiments, a solvent within a solvent system as described herein is substituted with one or more functional groups, such as, hydroxyl, ether, aldehyde, ketone, ester, carboxylic acid, amide, or combinations thereof.

In some embodiments, a solvent system described herein comprises one or more solvents that interrupts or interferes with interactions between neighboring rofecoxib molecules. For example, in some embodiments, a solvent system comprises a solvent that disrupts noncovalent interactions between aromatic rings of rofecoxib, for example, pi stacking between individual rofecoxib molecules. In some embodiments, a solvent system comprises a solvent that disrupts pi stacking. Non-limiting examples of solvents that disrupt pi stacking include alpha Bisabolol, Alpha Cedrene, Alpha Phellandrene, Alpha Pinene, Alpha Terpineol, Beta, Caryophyllene, Beta Pinene, Borneol, Cadinene, Camphene, Camphor, Caryophyllene Oxide, Citral, Citronellol, Delta 3 Carene, Limonene, Eucalyptol, Eugenol, Farnesene, Fenchol, Gamma Terpinene, Geraniol, Geranyl Acetate, Humulene, Isoborneol, Linalool, Menthol, Myrcene, Nerol, Nerolidol, Nookatone, Ocimene, Para-Cymene, Phytol, Quercetin, Terpinolene, and Valencene.

In some embodiments, the solvent systems described herein contain two or more of the solvents listed throughout this disclosure.

In some embodiments, the solvent system comprises up to about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, or about 99% w/w of the topical rofecoxib compositions.

In some embodiments, the rofecoxib topical composition comprises up to about 90% w/w of solvent system. In some embodiments, the rofecoxib topical composition comprises up to about 80% w/w of solvent system. In some embodiments, the rofecoxib topical composition comprises up to about 70% w/w of solvent system.

In some embodiments, the rofecoxib topical compositions comprise up to about 70% w/w of solvent system and up to about 5% w/w rofecoxib. In some embodiments, the rofecoxib topical compositions comprise up to about 75 w/w of solvent system and up to about 5 w/w rofecoxib. In some embodiments, the rofecoxib topical compositions comprise up to about 80% w/w of solvent system and up to about 5% w/w. In some embodiments, the rofecoxib topical compositions comprise up to about 85 w/w of solvent system and up to about 5 w/w rofecoxib. In some embodiments, the rofecoxib topical compositions comprise up to about 90% w/w of solvent system and up to about 5% w/w rofecoxib. In some embodiments, the rofecoxib topical compositions comprise up to about 95 w/w of solvent system and up to about 5 w/w rofecoxib. In some embodiments, the rofecoxib topical compositions comprise up to about 99% w/w of solvent system and up to about 1% w/w rofecoxib. In some embodiments, the rofecoxib topical compositions comprise up to about 98% w/w of solvent system and up to about 2% w/w rofecoxib. In some embodiments, the rofecoxib topical compositions comprise up to about 95% w/w of solvent system and up to about 1% w/w rofecoxib. In some embodiments, the rofecoxib topical compositions comprise up to about 93% w/w of solvent system and up to about 2% w/w rofecoxib. In some embodiments, the rofecoxib topical compositions comprise up to about 97% w/w of solvent system and up to about 2% w/w rofecoxib. In some embodiments, the rofecoxib topical compositions comprise up to about 96% w/w of solvent system and up to about 2% w/w rofecoxib. In some embodiments, the rofecoxib topical compositions comprise up to about 96% w/w of solvent system and up to about 3% w/w rofecoxib.

In some embodiments, a solvent within the solvent systems described herein comprises from about 0.1% w/w to about 99% w/w of the rofecoxib topical composition. In some embodiments, a solvent within the solvent systems described herein comprises from about 0.1% w/w, about 0.2% w/w, about 0.3% w/w, about 0.4% w/w, about 0.5 w/w, about 0.6% w/w, about 0.7% w/w, about 0.8% w/w, about 0.9% w/w, about 1.0% w/w, about 1.5 w/w, about 2.0% w/w, about 2.5% w/w, about 3.0% w/w, about 3.5% w/w, about 4.0% w/w, about 4.5% w/w, about 5.0 w/w, about 5.5 w/w, about 6.0% w/w, about 6.5 w/w, about 7.0% w/w, about 7.5 w/w, about 8.0% w/w, about 8.5 w/w, about 9.0% w/w, about 9.5 w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, about 25%, about 26% w/w, about 27% w/w, about 28% w/w, about 29% w/w, about 30% w/w, about 35 w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, or about 99% w/w of the rofecoxib topical composition.

In some embodiments, the solvent systems of the present invention comprise mixtures of two or more, three or more, four or more, five or more, or six or more solvents. The relative amounts of the various solvents (as described herein) can vary depending on the specific solvents used.

In some embodiments, the solvent system contains AC. In some embodiments, the solvent system contains from about 0.1% w/w AC to about 15% w/w AC. In some embodiments, the solvent system contains about 1% w/w, about 2% w/w, about 3% w/w, about 4% w/w, about w/w, about 6% w/w, about 7% w/w, about 8% w/w, about 9% w/w, about 10% w/w, about w/w, about 12% w/w, about 13% w/w, about 14% w/w, or about 15 w/w AC, including all values and ranges in between. In some embodiments, the rofecoxib topical composition contains from about 0.1% w/w AC to about 15% w/w AC. In some embodiments, the rofecoxib topical composition contains about 1% w/w, about 2% w/w, about 3% w/w, about 4% w/w, about 5 w/w, about 6% w/w, about 7% w/w, about 8% w/w, about 9% w/w, about 10% w/w, about 11% w/w, about 12% w/w, about 13% w/w, about 14% w/w, or about 15% w/w AC, including all values and ranges in between.

In some embodiments, the solvent system contains M24D. In some embodiments, the solvent system contains from about 0.1% w/w M24D to about 15% w/w M24D. In some embodiments, the solvent system contains about 1% w/w, about 2% w/w, about 3% w/w, about 4% w/w, about 5 w/w, about 6% w/w, about 7% w/w, about 8% w/w, about 9% w/w, about 10% w/w, about 11% w/w, about 12% w/w, about 13% w/w, about 14% w/w, or about 15% w/w M24D, including all values and ranges in between. In some embodiments, the rofecoxib topical composition contains from about 0.1% w/w M24D to about 15% w/w M24D. In some embodiments, the rofecoxib topical composition contains about 1% w/w, about 2% w/w, about 3% w/w, about 4% w/w, about 5 w/w, about 6% w/w, about 7% w/w, about 8% w/w, about 9% w/w, about 10% w/w, about 11 w/w, about 12% w/w, about 13% w/w, about 14% w/w, or about 15 w/w M24D, including all values and ranges in between.

In some embodiments, the solvent system contains AT. In some embodiments, the solvent system contains from about 0.1% w/w AT to about 15% w/w AT. In some embodiments, the solvent system contains about 1% w/w, about 2% w/w, about 3% w/w, about 4% w/w, about w/w, about 6% w/w, about 7% w/w, about 8% w/w, about 9% w/w, about 10% w/w, about w/w, about 12% w/w, about 13% w/w, about 14% w/w, or about 15 w/w AT, including all values and ranges in between. In some embodiments, the solvent system contains about 5% w/w AT. In some embodiments, the solvent system contains about 8% w/w AT. In some embodiments, the rofecoxib topical composition contains from about 0.1% w/w AT to about 15% w/w AT. In some embodiments, the rofecoxib topical composition contains about 5% w/w AT. In some embodiments, the rofecoxib topical composition contains about 8% w/w AT. In some embodiments, the rofecoxib topical composition contains about 1% w/w, about 2% w/w, about 3% w/w, about 4% w/w, about 5 w/w, about 6% w/w, about 7% w/w, about 8% w/w, about 9% w/w, about 10% w/w, about 11 w/w, about 12% w/w, about 13% w/w, about 14% w/w, or about 15% w/w AT, including all values and ranges in between.

In some embodiments, the solvent system contains BA. In some embodiments, the solvent system contains from about 0.1% w/w BA to about 5% w/w BA. In some embodiments, the solvent system contains about 0.1% w/w, about 0.2% w/w, about 0.3% w/w, about 0.4% w/w, about 0.5 w/w, about 0.6% w/w, about 0.7% w/w, about 0.8% w/w, about 0.9% w/w, about 1.0% w/w, about 1.5 w/w, about 2.0% w/w, about 2.5 w/w, about 3.0% w/w, about 3.5 w/w, about 4.0% w/w, about 4.5 w/w, or about 5.0% w/w BA, including all values and ranges in between. In some embodiments, the solvent system comprises about 2.5% w/w BA. In some embodiments, the solvent system comprises about 2.6% w/w BA. In some embodiments, the solvent system comprises about 2.7% w/w BA. In some embodiments, the rofecoxib topical composition contains from about 0.1% w/w BA to about 5% w/w BA. In some embodiments, the rofecoxib topical composition comprises about 2.5% w/w BA. In some embodiments, rofecoxib topical composition comprises about 2.6% w/w BA. In some embodiments, the rofecoxib topical composition comprises about 2.7% w/w BA. In some embodiments, the rofecoxib topical composition contains about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.5% w/w, about 2.0% w/w, about 2.5% w/w, about 3.0% w/w, about 3.5% w/w, about 4.0% w/w, about 4.5% w/w, or about 5.0% w/w BA, including all values and ranges in between.

In some embodiments, the solvent system contains DS. In some embodiments, the solvent system contains from about 0.1% w/w DS to about 25% w/w DS. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% DS, including all values and ranges in between. In some embodiments, the rofecoxib topical composition contains from about 0.1% w/w DS to about 25% w/w DS. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% DS, including all values and ranges in between.

In some embodiments, the solvent system contains DGME. In some embodiments, the solvent system contains from about 0.1% w/w DGME to about 50% w/w DGME. In some embodiments, the solvent system contains about 0.1% w/w, about 0.5% w/w, 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w, or about 40% w/w, or about 45% w/w, or about 50% w/w DGME, including all values and ranges in between. In some embodiments, the solvent system comprises about 18.5% w/w DGME. In some embodiments, the solvent system comprises about 18.2% w/w DGME. In some embodiments, the solvent system comprises about 19% w/w DGME. In some embodiments, the solvent system comprises about 8% w/w DGME. In some embodiments, the solvent system comprises about 9% w/w DGME. In some embodiments, the solvent system comprises about 5.4% w/w DGME. In some embodiments, the rofecoxib topical composition contains from about 0.1% w/w DGME to about 50% w/w DGME. In some embodiments, the rofecoxib topical composition comprises about 19% w/w DGME. In some embodiments, the rofecoxib topical composition comprises about 19.9% w/w DGME. In some embodiments, the rofecoxib topical composition comprises about 8% w/w DGME. In some embodiments, the rofecoxib topical composition comprises about 9.1% w/w DGME. In some embodiments, the solvent system comprises about 5.4% w/w DGME. In some embodiments, the rofecoxib topical composition contains about 0.1% w/w, 0.5% w/w, 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w, or about 40% w/w, or about 45% w/w, or about 50% w/w DGME, including all values and ranges in between.

In some embodiments, the solvent system contains DIA. In some embodiments, the solvent system contains from about 0.1% w/w DIA to about 15% w/w DIA. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w DIA, including all values and ranges in between. In some embodiments, the solvent system comprises about 10% w/w DIA. In some embodiments, the solvent system comprises about 11% w/w DIA. In some embodiments, the solvent system comprises about 12% w/w DIA. In some embodiments, the solvent system comprises about 13% w/w DIA. In some embodiments, the rofecoxib topical composition contains from about 0.1% w/w DIA to about 15% w/w DIA. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w DIA, including all values and ranges in between. In some embodiments, the rofecoxib topical composition comprises about 10% w/w DIA. In some embodiments, the rofecoxib topical composition comprises about 11% w/w DIA. In some embodiments, the rofecoxib topical composition comprises about 12% w/w DIA. In some embodiments, the rofecoxib topical composition comprises about 13% w/w DIA.

In some embodiments, the solvent system contains DI. In some embodiments, the solvent system contains from about 0.1% w/w DI to about 20% w/w DI. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, or about 20% w/w DI, including all values and ranges in between. In some embodiments, the solvent system comprises about 15% w/w DI. In some embodiments, the solvent system comprises about 15.5% w/w DI. In some embodiments, the solvent system comprises about 16% w/w DI. In some embodiments, the rofecoxib topical composition contains from about 0.1% w/w DI to about 20% w/w DI. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, or about 20% w/w DI, including all values and ranges in between. In some embodiments, the rofecoxib topical composition comprises about 15% w/w DI. In some embodiments, the rofecoxib topical composition comprises about 15.5% w/w DI. In some embodiments, the rofecoxib topical composition comprises about 16% w/w DI.

In some embodiments, the solvent system contains DMSO. In some embodiments, the solvent system contains from about 0.1% w/w DMSO to about 50% w/w DMSO. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w, or about 40% w/w, or about 45% w/w, or about 50% w/w DMSO, including all values and ranges in between. In some embodiments, the solvent system contains about 11.5% w/w DMSO. In some embodiments, the solvent system contains about 16% w/w DMSO. In some embodiments, the solvent system contains about 21.5% w/w DMSO. In some embodiments, the rofecoxib topical composition contains from about 0.1% w/w DMSO to about 50% w/w DMSO. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w, or about 40% w/w, or about 45% w/w, or about 50% w/w DMSO, including all values and ranges in between. In some embodiments, the rofecoxib topical composition contains about 10% w/w DMSO. In some embodiments, the rofecoxib topical composition contains about 15.5% w/w DMSO. In some embodiments, the rofecoxib topical composition contains about 21% w/w DMSO. In some embodiments, the DMSO is 10% DMSO by volume. For example, 10% DMSO may contain 10 mL of DMSO for 90 mL of water.

In some embodiments, the solvent system contains EA. In some embodiments, the solvent system contains from about 0.1% w/w EA to about 35% w/w EA. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w EA, including all values and ranges in between. In some embodiments, the solvent system contains about 22.5% w/w EA. In some embodiments, the rofecoxib topical composition contains from about 0.1% w/w EA to about 35% w/w EA. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w EA, including all values and ranges in between. In some embodiments, the rofecoxib topical composition contains about 21.8% w/w EA.

In some embodiments, the solvent system contains IPTD. In some embodiments, the solvent system contains from about 0.1% w/w IPTD to about 35% w/w IPTD. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w IPTD, including all values and ranges in between. In some embodiments, the rofecoxib topical composition contains from about 0.1% w/w IPTD to about 35% w/w IPTD. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w IPTD, including all values and ranges in between.

In some embodiments, the solvent system contains MP. In some embodiments, the solvent system contains from about 0.1% w/w MP to about 35% w/w MP, for example about 0.1% w/w MP, about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w IPTD, including all values and ranges in between.

In some embodiments, the solvent system contains OA. In some embodiments, the solvent system contains from about 0.1% w/w OA to about 25% w/w OA. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w OA, including all values and ranges in between. In some embodiments, the solvent system comprises about 8% w/w OA. In some embodiments, the solvent system comprises 5.4% w/w OA. In some embodiments, the rofecoxib topical composition contains from about 0.1% w/w OA to about 25% w/w OA. In some embodiments, the rofecoxib topical composition contains about 1% w/w, about 2% w/w, about 3% w/w, about 4% w/w, about 5 w/w, about 6% w/w, about 7% w/w, about 8% w/w, about 9% w/w, about 10% w/w, about 11 w/w, about 12% w/w, about 13% w/w, about 14% w/w, or about 15 w/w, or about 16% w/w, about 17% w/w, about 18% w/w, about 19% w/w, about 20% w/w, about 21% w/w, about 22% w/w, about 23% w/w, about 24% w/w, or about 25% w/w OA, including all values and ranges in between. In some embodiments, the rofecoxib topical composition contains about 7.8% w/w OA. In some embodiments, the rofecoxib topical composition contains about 5.2% w/w OA.

In some embodiments, the solvent system contains PEG. In some embodiments, the solvent system contains from about 0.1% w/w PEG to about 75% w/w PEG. In some embodiments, the solvent system contains about 1% w/w, about 2% w/w, about 3% w/w, about 4% w/w, about 5 w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25 w/w, or about 30% w/w, or about 35% w/w, about 40% w/w, about 45% w/w, about 50% w/w, about 55% w/w, about 60% w/w, about 65% w/w, about 70% w/w, or about 75% w/w PEG, including all values and ranges in between. In some embodiments, the rofecoxib topical composition contains from about 0.1% w/w PEG to about 75% w/w PEG. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w, or about 16% w/w, about 17% w/w, about 18% w/w, about 19% w/w, about 20% w/w, about 21% w/w, about 22% w/w, about 23% w/w, about 24% w/w, or about 25% w/w, or about 30% w/w, or about 35% w/w, about 40% w/w, about 45 w/w, about 50 w/w, about 55 w/w, about 60% w/w, about 65 w/w, about 70% w/w, or about 75% w/w PEG, including all values and ranges in between.

In some embodiments, the solvent system contains PS20. In some embodiments, the solvent system contains from about 0.1% w/w PS20 to about 15% w/w PS20. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w PS20, including all values and ranges in between. In some embodiments, the solvent system comprises about 15% w/w PS20. In some embodiments, the solvent system comprises about 16% w/w PS20. In some embodiments, the solvent system contains from about 0.1% w/w PS20 to about 15% w/w PS20. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w PS20, including all values and ranges in between. In some embodiments, the rofecoxib topical composition comprises about 15% w/w PS20. In some embodiments, the rofecoxib topical composition comprises about 16% w/w PS20.

In some embodiments, the solvent system contains PS80. In some embodiments, the solvent system contains from about 0.1% w/w PS80 to about 15% w/w PS80. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w PS80, including all values and ranges in between. In some embodiments, the rofecoxib topical composition contains from about 0.1% w/w PS80 to about 15% w/w PS80. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w PS80, including all values and ranges in between.

In some embodiments, the solvent system contains PC. In some embodiments, the solvent system contains from about 0.1% w/w PC to about 10% w/w PC. In some embodiments, the solvent system contains about 1% w/w, about 2% w/w, about 3% w/w, about 4% w/w, about 5% w/w, about 6% w/w, about 7% w/w, about 8% w/w, about 9% w/w, or about 10% w/w PC, including all values and ranges in between. In some embodiments, the solvent system comprises about 5% w/w PC. In some embodiments, the solvent system comprises about 5.2% w/w PC. In some embodiments, the solvent system comprises about 5% w/w PC. In some embodiments, the rofecoxib topical composition contains from about 0.1% w/w PC to about 10% w/w PC. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, or about 10% w/w PC, including all values and ranges in between. In some embodiments, the rofecoxib topical composition comprises about 5% w/w PC. In some embodiments, the rofecoxib topical composition comprises about 5.2% w/w PC. In some embodiments, the rofecoxib topical composition comprises about 5.4% w/w PC.

In some embodiments, the solvent system contains PGD. In some embodiments, the solvent system contains from about 0.1% w/w PGD to about 15% w/w PGD. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w PGD, including all values and ranges in between. In some embodiments, the solvent system contains about 10.4% w/w PGD. In some embodiments, the rofecoxib topical composition contains from about 0.1% w/w PGD to about 15% w/w PGD. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w PGD, including all values and ranges in between. In some embodiments, the rofecoxib topical composition contains about 10.4% w/w PGD.

In some embodiments, the solvent system contains PPG. In some embodiments, the solvent system contains from about 0.1% w/w PPG to about 95% w/w PPG. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, or about 95% w/w PPG, including all values and ranges in between. In some embodiments, the rofecoxib topical composition contains from about 0.1% w/w PPG to about 95% w/w PPG. In some embodiments, the rofecoxib topical composition contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, or about 95% w/w PPG, including all values and ranges in between.

In some embodiments, the solvent system contains lanoline. In some embodiments, the solvent system contains from about 0.1% w/w lanoline to about 15% w/w lanoline. In some embodiments, the solvent system contains about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w lanoline, including all values and ranges in between.

In some embodiments, the solvent systems described herein contain two or more solvents that work synergistically to dissolve rofecoxib. In some embodiments, BA and AC work synergistically to dissolve rofecoxib. In some embodiments, AC and PEG work synergistically to dissolve rofecoxib. In some embodiments, EA and PPG work synergistically to dissolve rofecoxib. In some embodiments, PEG and EA work synergistically to dissolve rofecoxib. In some embodiments, AC and DGME work synergistically to dissolve rofecoxib. In some embodiments, AC and PC work synergistically to dissolve rofecoxib. In some embodiments, AC and DI work synergistically to dissolve rofecoxib. In some embodiments, PC and DI work synergistically to dissolve rofecoxib. In some embodiments, PEG and PGD work synergistically to dissolve rofecoxib. In some embodiments, AC and PGD work synergistically to dissolve rofecoxib. In some embodiments, DI and PGD work synergistically to dissolve rofecoxib. In some embodiments, PC and PGD work synergistically to dissolve rofecoxib. In some embodiments, EA and DMSO work synergistically to dissolve rofecoxib. In some embodiments, PEG and PGD work synergistically to dissolve rofecoxib. In some embodiments, PEG and EA work synergistically to dissolve rofecoxib. In some embodiments, PEG and DGME work synergistically to dissolve rofecoxib. In some embodiments, EA and DGME work synergistically to dissolve rofecoxib. In some embodiments, EA and BA work synergistically to dissolve rofecoxib. In some embodiments, DGME and PGD work synergistically to dissolve rofecoxib. In some embodiments, AC and PGD work synergistically to dissolve rofecoxib. In some embodiments, BA and PGD work synergistically to dissolve rofecoxib. In some embodiments, EA and M24D work synergistically to dissolve rofecoxib.

In some embodiments, solvent systems that contain DI and PC work synergistically to dissolve rofecoxib. In some embodiments, a solvent system containing DI and PC contains about w/w DI and about 5 w/w PC. In some embodiments, solvent systems that contain DI and PC and one or more additional solvents synergistically work to dissolve rofecoxib. In some embodiments, the additional solvents are selected from the group consisting of acetone (AC), 2-methylpentane-2,4-diol (M24D), alpha-terpineol (AT), benzyl alcohol (BA), diethyl sebacate (DS), diethylene glycol monoethyl ether (DGME), diisopropyl adipate (DIA), dimethyl sulfoxide (DMSO), ethyl acetate (EA), isopropyl tetradecanoate/myristate (IPTD), N-methyl-2-pyrrolidone (MP), oleic acid (OA), polyethylene glycol 400 (PEG), polysorbate 20 (PS20), polysorbate 80 (PS80), propylene glycol diacetate (PGD), and propylene glycol (PPG).

In some embodiments, solvent systems that contain DI, PC, and DMSO work synergistically to dissolve rofecoxib. In some embodiments, a solvent system containing DI and PC contains about 10-20% DI, 2.5-10% w/w PC, and about 10-20% w/w DMSO. In some embodiments, solvent systems containing DI, PC, and DMSO contain about 15% w/w DI and about 5% w/w PC. In some embodiments, solvent systems that contain DI, PC, DMSO and one or more additional solvents synergistically work to dissolve rofecoxib. In some embodiments, the additional solvents are selected from the group consisting of acetone (AC), 2-methylpentane-2,4-diol (M24D), alpha-terpineol (AT), benzyl alcohol (BA), diethyl sebacate (DS), diethylene glycol monoethyl ether (DGME), diisopropyl adipate (DIA), dimethyl sulfoxide (DMSO), ethyl acetate (EA), isopropyl tetradecanoate/myristate (IPTD), N-methyl-2-pyrrolidone (MP), oleic acid (OA), polyethylene glycol 400 (PEG), polysorbate 20 (PS20), polysorbate 80 (PS80), propylene glycol diacetate (PGD), and propylene glycol (PPG).

In some embodiments, AC, PEG, and PGD work synergistically to dissolve rofecoxib. In some embodiments, DI, BA, and PC work synergistically to dissolve rofecoxib. In some embodiments, DI, PC, and DMSO work synergistically to dissolve rofecoxib. In some embodiments, BA, AC, and PEG work synergistically to dissolve rofecoxib. In some embodiments, BA, PEG, and PGD work synergistically to dissolve rofecoxib. In some embodiments, PC, AC, and PGD work synergistically to dissolve rofecoxib. In some embodiments, BA, AC, and PGD work synergistically to dissolve rofecoxib. In some embodiments, PC, PEG, and PGD work synergistically to dissolve rofecoxib. In some embodiments, DI, PC, and AC work synergistically to dissolve rofecoxib. In some embodiments, PC, BA, and AC work synergistically to dissolve rofecoxib. In some embodiments, DI, PC, and BA work synergistically to dissolve rofecoxib. In some embodiments, BA, AC, and PEG work synergistically to dissolve rofecoxib. In some embodiments, PC, AC, and PGD work synergistically to dissolve rofecoxib. In some embodiments, DI, PC, and EA work synergistically to dissolve rofecoxib. In some embodiments, BA, AC, and PEG work synergistically to dissolve rofecoxib. In some embodiments, PC, AC, and PEG work synergistically to dissolve rofecoxib. In some embodiments, DI, PC, and DGME work synergistically to dissolve rofecoxib. In some embodiments, DI, PC, and PEG work synergistically to dissolve rofecoxib. In some embodiments, DI, PC, and PGD work synergistically to dissolve rofecoxib. In some embodiments, PC, AC, and PGD work synergistically to dissolve rofecoxib. In some embodiments, AC, PEG, and PGD work synergistically to dissolve rofecoxib.

Design of Solvent System for Dissolving Rofecoxib: Solubility Parameters

In some embodiments, solubility parameters may be utilized to select a suitable solvent system for solubilizing rofecoxib. Non-limiting examples of solubility parameters include the Hildebrand solubility parameter, the Hansen solubility parameters, and the partition coefficient.

In some embodiments, the Hildebrand solubility parameter ($\delta$) is utilized to select a suitable solvent system for solubilizing rofecoxib. The Hildebrand solubility parameter is defined as the square root of a solvent's cohesive energy density, which is equal to its heat of vaporization divided by the molar volume. The Hildebrand solubility parameter is expressed in units of $MPa^{1/2}$. In some embodiments, the solvent systems described have a Hildebrand solubility parameter that is greater than 15.

In some embodiments, the Hansen Solubility Parameters solubility parameters are utilized to select a suitable solvent system for solubilizing rofecoxib. The Hansen Solubility Parameters include dispersion ($\delta_d$), polar ($\delta_d$), and hydrogen bonding ($\delta_h$) parameters. These three parameters can be treated as coordinates for a point in a three-dimensional space, which is also known as the Hansen space. The closest two molecules are in this three-dimensional space, the more likely they are to dissolve into each other. In some embodiments, the Hansen Solubility Parameters teach the skilled artisan about the intermolecular forces a solvent within the solvent system will make with other solvents within the solvent system, rofecoxib, or other additional ingredients. The Hansen Solubility Parameters are related to the Hildebrand parameter $\delta$ by the formula $\delta^2=\delta_d^2\delta_p^2+\delta_h^2$. The value for these parameters, for various solvents, can be found in Hansen, Charles M, Hansen Solubility Parameters, A User's Handbook, CRC Press, 2000, which is incorporated by reference in its entirety herein. In some embodiments, the solvent systems described have a $\delta_h$ that is greater than 7. In some embodiments, the solvent systems described have a $\delta_d$ that is greater than 15. In some embodiments, the solvent systems described have a $\delta_p$ that is greater than 7. In some embodiments, the solvent systems described have a $\delta_h$ that is greater than 7 and a $\delta_d$ that is greater than 15. In some embodiments, the solvent systems described have a $\delta_h$ that is greater than 7 and a $\delta_p$ that is greater than 7. In some embodiments, the solvent systems described have a $\delta_d$ that is greater than 15 and a $\delta_h$ that is greater than 7 and a $\delta_p$ that is greater than 7. In some embodiments, the solvent systems described have a $\delta_h$ that is greater than 7, a $\delta_d$ that is greater than 15, and a $\delta_p$ that is greater than 7.

In some embodiments, the partition coefficient (P) is used to select a suitable solvent system for solubilizing rofecoxib. The partition coefficient describes the propensity of a neutral compound to dissolve in an immiscible biphasic system of lipids and water. In some embodiments, log (P) is utilized to predict whether a compound will dissolve in a given solution. A negative value for log P suggests that a compound will dissolve in an aqueous phase, whereas a positive value for log P suggests that a compound will dissolve in the lipid phase.

In some embodiments, a solvent systems described herein comprises at least one solvent with a negative partition coefficient, for example, at least one solvent, at least two solvents, at least three solvents, at least four solvents, at least five solvents, or at least six solvents. In some embodiments, solvents having negative partition coefficients may provide better transfer across a membrane and/or skin than solvents having positive partition coefficients. In some embodiments, the partition coefficient of a solvent within a solvent system described herein is from about 0.1 to about to about −1.5, about 0 to about −1.5, about −0.001 to about −1.5, about −0.01 to about −1.0, about −0.1 to about −1.0, and any partition coefficient encompassed by any of the aforementioned ranges.

In some embodiments, a solvent system described herein comprises at least one solvent with a positive partition coefficient, for example, at least one solvent, at least two solvents, at least three solvents, at least four solvents, at least five solvents, or at least six solvents. In some embodiments, a solvent has a partition coefficient from about 0.1 to about 2.5, for example, about 0.1 to about 2.5, about 0.1 to about 1, about 0.1 to about 1.5, about 0.5 to about 1.5, about 1 to about 2.5, and any partition coefficient encompassed by any one the aforementioned ranges.

In some embodiments, a solvent system comprises at least one solvent with a positive partition coefficient and at least one solvent with a negative partition coefficient. In some embodiments, a solvent system comprises at least one solvent with a positive partition coefficient and at least two solvents with a negative partition coefficient. In some embodiments, a solvent system comprises at least two solvents with a positive partition coefficient and at least one solvent with a negative partition coefficient. In some embodiments, a solvent system comprises at least two solvents with a positive partition coefficient and at least two solvents with a negative partition coefficient. In some embodiments, a solvent system comprises at least three solvents with a positive partition coefficient and at least one solvent with a negative partition coefficient. In some embodiments, a solvent system comprises at least one solvent with a positive partition coefficient and at least three solvents with a negative partition coefficient. In some embodiments, a solvent system comprises at least four solvents with a positive partition coefficient and at least one solvent with a negative partition coefficient. In some embodiments, a solvent system comprises at least one solvent with a positive partition coefficient and at least four solvents with a negative partition coefficient. In some embodiments, a solvent system comprises at least four solvents with a positive partition coefficient and at least two solvents with a negative partition coefficient. In some embodiments, a solvent system comprises at least two solvents with a positive partition coefficient and at least four solvents with a negative partition coefficient.

In some embodiments, other physical parameters of the solvents disclosed herein, including but not limited to density, the hydrogen bond donor count, the hydrogen bond acceptor count, heat of vaporization, the enthalpy of fusion, the Kauri-butanol value, aniline cloud-point, heptane number, wax number, aromatic character, and cohesive energy density are utilized to select a solvent system for the rofecoxib topical compositions described. Savjani et al. describes many of these parameters and is incorporated by reference in its entirety herein: Savjani et al. ISRN Pharm. 2012; 2012: 195727.

The values of log P, hydrogen bonding donor count (H-Bond D), and hydrogen bonding acceptor count (H-Bond A) for some solvents described throughout this disclosure are found in Table 1.

TABLE 1

Solubility Parameters of Solvents

| Solvent | logP | H-Bond D, H-Bond A | $\delta$ (MPa$^{1/2}$) | $\Delta_d$ (MPa$^{1/2}$) | $\Delta_p$ (MPa$^{1/2}$) | $\Delta_h$ (MPa$^{1/2}$) |
|---|---|---|---|---|---|---|
| Acetone | −0.1 | | 19.9 | 15.5 | 10.4 | 7 |
| 2-Methyl-pentane-2,4-diol | 0.3 | 2, 2 | 27.5 | 16.4 | 8 | 20.6 |
| alpha-Terpineol 95.0+ % | 1.8 | 1, 1 | 19.1 | 17.1 | 3.6 | 7.6 |
| Benzyl Alcohol | 1.10 | 1, 1 | 23.8 | 18.4 | 6.3 | 13.7 |
| Diethyl Sebacate | 3.5 | 0, 4 | 17.1 | 16 | 4 | 4.7 |
| Diethylene Glycol Monoethyl Ether | −0.5 | 1, 3 | 23.5 | 16.2 | 9.2 | 14.3 |
| Diisopropyl Adipate | 2.2 | 0, 4 | | | | |
| Dimethyl Isosorbide | −0.6 | 0, 4 | 20.4 | 17.6 | 7.1 | 7.5 |
| Dimethyl Sulfoxide | −0.6 | 0, 2 | 26.7 | 18.4 | 16.4 | 10.2 |
| Ethyl Acetate | 0.76 | 0, 2 | 18.2 | 15.8 | 5.3 | 7.2 |
| Isopropyl tetradecanoate (also called isopropyl myristate) | 7.2 | 0, 2 | 16.8 | 16.2 | 2.4 | 3.7 |
| N-Methyl-2-Pyrrolidone | 0.5 | | 23.0 | 18 | 12.3 | 7.2 |
| Oleic acid | 6.5 | 1, 2 | 17.4 | 16 | 2.8 | 6.2 |
| PEG 400 | 4.6 | 3, 1 | | | | |
| Polysorbate 20, MP | 2.5 | 3, 10 | | | | |
| Polysorbate 80, Acros | 4.8 | 3, 10 | | | | |
| Propylene Carbonate | −0.4 | 0, 3 | 27.2 | 20 | 18 | 4.1 |
| Propylene Glycol Diacetate | 0.7 | 2, 2 | | | | |

TABLE 1-continued

Solubility Parameters of Solvents

| Solvent | logP | H-Bond D, H-Bond A | δ (MPa$^{1/2}$) | Δ$_d$ (MPa$^{1/2}$) | Δ$_p$ (MPa$^{1/2}$) | Δ$_h$ (MPa$^{1/2}$) |
|---|---|---|---|---|---|---|
| Propylene Glycol, MP | −0.9 | 0, 4 | 30.2 | 16.8 | 9.4 | 23.3 |
| lanoline | 16.3 | | 19.9 | 15.5 | 10.4 | 7 |

In some embodiments, the topical rofecoxib compositions provided herein remain soluble over time. In some embodiments, the topical rofecoxib compositions provided herein, remain in solution after administration.

Maintenance of Rofecoxib in Solvent System Over Time

An additional difficulty in formulating rofecoxib topical compositions is maintaining rofecoxib in solution after application to the skin. Volatility of one or more of the solvents, additional ingredients, and/or vehicle within a topical composition may affect the solubility of rofecoxib in the rofecoxib topical compositions. Solvent evaporation over time may change the composition of the solvent system.

The penetration rate of rofecoxib, solvents, additional ingredients, and the vehicle within a topical composition also affects the solubility of rofecoxib over time. As a topical composition is absorbed by the skin, differential absorption of solvents, additional ingredients, the vehicle, or rofecoxib may change the composition of the rofecoxib topical composition.

Changes in the composition of the solvent system as a result of evaporation or differential absorption may lead to precipitation of rofecoxib solution before penetration of epithelial tissue. Accordingly, the solvent systems used herein to dissolve rofecoxib are not absorbed more rapidly than the rofecoxib and do not evaporate after application. In some embodiments, the solubility of rofecoxib within the rofecoxib topical compositions described herein is maintained after administration.

In some embodiments, the solubility of rofecoxib is maintained within the rofecoxib topical compositions for at least 48 hours after application to the skin. In some embodiments, the solubility of rofecoxib is maintained within the rofecoxib topical compositions for at least about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours, or more.

In some embodiments, passive diffusion is the mechanism by which rofecoxib penetrates the skin. Passive diffusion can be described thermodynamically by Fick's first law.

$$J = \frac{KD(c_{app} - c_{rec})}{h}$$

where (J) describes the steady state flux per unit area, (K) is the partition of the drug between the skin and the formulation and (D) is the diffusion coefficient through the diffusional path length (h). Since usually the concentration of the permeate in the applied dose ($c_{app}$) is so much higher than the concentration in the receptor phase (Crec) this equation can be simplified to: $J=k_p c_{app}$, where $k_p$ is the permeability coefficient and equal to KD/h (Hadgraft, 2004). According to Fick's law, the most important factors that influence flux across the skin are the concentration gradient of the drug within the skin, the partition coefficient of the permeate and the diffusion coefficient (Thomas and Finnin, 2004; Hadgraft, 2004). In addition, the flux (J) of a molecule across a membrane should increase linearly with concentration until $c_{app}$ reaches the solubility limit i.e. at the point of saturation (i.e. a thermodynamic activity (TA) of 1. Assuming there is no interaction between the drug and the vehicle, then this means that, regardless of 1) the nature of the vehicle in the drug saturated formulation, and 2) the quantity of a drug saturated formulation applied to the membrane at a TA=1, the flux/release of the drug will remain the same. Thus, when a saturated drug formulation is applied to the skin, the drug will be at its highest thermodynamic activity, in accordance with Fick's law.

In some embodiments, rofecoxib is present in a saturating amount in the rofecoxib topical compositions described herein. In some embodiments, at least about 60% of the rofecoxib necessary to achieve saturation is present in the rofecoxib topical compositions. In some embodiments, at least about 60%, about 65%, about 70%, about 75%, about 80%, about 85%, about 90%, about 95%, or about 100% of the rofecoxib necessary to achieve saturation is present in the rofecoxib topical compositions.

In some embodiments, the ability of rofecoxib to penetrate the skin is measured. In some embodiments, rofecoxib penetrates the skin when it is dissolved in a solvent system described herein. In some embodiments, rofecoxib is at least about 70% dissolved in the topical rofecoxib compositions described herein. In some embodiments, rofecoxib is at least about 70%, about 75%, about 80%, about 85%, about 90%, about 95%, or about 100% dissolved.

The ability of rofecoxib to penetrate skin is measured according to methods known by a person of skill in the art. In some embodiments, the ability of rofecoxib to penetrate skin is measured using one or more techniques selected from the group consisting of microscopy, confocal Raman spectroscopy, diffusion cells, static diffusion cells, flow-through cells, tape stripping with high performance liquid chromatography, and skin parallel artificial membrane permeability assay. Zsiko et al., which describes many of these methods, is incorporated by reference herein in its entirety (Zsiko et al. Sci. Pharm. 2019, 87(3), 19).

In some embodiments, flux (J) measurements are conducted to evaluate the ability of rofecoxib to penetrate the skin. In some embodiments, the following equation is utilized to measure flux (J): J=Q/(A*t), where Q is the quantity of compound traversing the membrane in time t, and A is the area of exposed membrane in $cm^2$. Units of flux are quantity/$cm^2$/min, for example μg/$cm^2$/h or pg/$cm^2$/min, or cpm/$cm^2$/min. Flux measurements may be conducted according to known methods in the art. In some embodiments, methods of measuring flux are selected from the group consisting of a diffusion cell, a static cell, a continuous flow cell, and fluorescence. The Franz diffusion cell method of measuring flux is described by Ng. et al. and Williams, both of which are incorporated by reference herein in their entirety: Ng et. Al. Pharmaceutics. 2010 June; 2(2): 209-223; Williams AC, Transdermal and Topical Drug Delivery: Pharmaceutical Press PhP 2003.

In some embodiments, animal studies will be conducted to evaluate the efficacy of the rofecoxib topical compositions at alleviating pain and/or arthritis. Animal studies using conventional pain models, including but not limited to, the formalin model, tail-flick model, hot plate model, complete Freund's Adjuvant (CFA) model, nerve growth factor (NGF) model, Carrageenan Paw Edema (CPE) model, and monoiodoacetate (MIA)-induced osteoarthritis joint pain model. Gregory et al. describes non-limiting examples of animal models that the rofecoxib topical compositions will be evaluated in. Gregory et al. is incorporated by reference herein in its entirety: Gregory et al. J Pain. 2013 November; 14(11) In some embodiments, animal models of diseases selected from the group consisting of arthritis, osteoarthritis, juvenile rheumatoid arthritis, joint pain due to injury e.g. ankle sprains, sports injuries, carpal tunnel syndrome, ankle sprains, rheumatoid arthritis, inflammation, low back pain, ankylosing spondylitis, psoriatic arthritis, tennis elbow, headache, and migraine will be utilized to evaluate the rofecoxib topical compositions. In some embodiments, the rofecoxib topical compositions will be evaluated in humans that exhibit one or more of the following of arthritis, osteoarthritis, juvenile rheumatoid arthritis, joint pain due to injury e.g. ankle sprains, sports injuries, carpal tunnel syndrome, ankle sprains, rheumatoid arthritis, inflammation, low back pain, ankylosing spondylitis, psoriatic arthritis, tennis elbow, headache, and migraine. In some embodiments, the rofecoxib topical compositions will be evaluated in pre-clinical studies as mandated by the Food and Drug Administration for topical formulations.

Additional Ingredients

In some embodiments, the topical compositions of the present disclosure can also include any one of, any combination of, or all of the following additional ingredients: water, a humectant, a chelating agent, a UV absorption agent, a moisturizing agent, an excipient, a preservative, a thickening agent, a penetration enhancer, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients. U.S. Pat. No. 9,814,670 (issued Nov. 14, 2017) describes many of these ingredients and is incorporated by reference in its entirety for all purposes herein.

In some embodiments, about 0.01% w/w to about 40% w/w of an additional ingredient is contained in the topical compositions. In some embodiments, the topical composition contains about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.10% w/w, about 0.15% w/w, about 0.20% w/w, about 0.25% w/w, about 0.30% w/w, about 0.35% w/w, about 0.40% w/w, about 0.50% w/w, about 0.60% w/w, about 0.70% w/w, about 0.80% w/w, about 0.90% w/w, about 1.0% w/w, about 2.0% w/w, about 3.0% w/w, about 4.0% w/w, about 5.0 w/w, about 6.0% w/w, about 7.0% w/w, about 8.0% w/w, about 9.0% w/w, about 10.0% w/w, about 11 w/w, about 12% w/w, about 13% w/w, about 14% w/w, about 15 w/w, about 16% w/w, about 17% w/w, about 18% w/w, about 19% w/w, about 20% w/w, about 21% w/w, about 22% w/w, about 23% w/w, about 24% w/w, about 25 w/w, about 26% w/w, about 27% w/w, about 28% w/w, about 29% w/w, about 30% w/w, about 31% w/w, about 32% w/w, about 33% w/w, about 34% w/w, about 35 w/w, about 36% w/w, about 37% w/w, about 38% w/w, about 39% w/w, or about 40% w/w of additional ingredient.

Humectants

In some embodiments, the present disclosure teaches topical compositions that contain a humectant. In some embodiments, humectants cause increased elasticity, smoothness, and hydration of the skin. In some embodiments, humectants are used in the topical compositions of the disclosure. Non-limiting examples of humectants include glyceryl glucoside, *Aloe vera*, hyaluronic acid, amino acids, chondroitin sulfate, diglycerol, erythritol, fructose, glucose, glycerol, glycerol polymers, glycol, 1,2,6-hexanetriol, honey, hyaluronic acid, hydrogenated honey, hydrogenated starch hydrolyzate, inositol, lactitol, maltitol, maltose, mannitol, natural humectant factor, PEG-15-butanediol, polyglyceryl sorbitol, salts of pyrrolidonecarboxylic acid, potassium PCA, propylene glycol, saccharide isomerate, sodium glucuronate, sodium PCA, sorbitol, sucrose, trehalose, urea and xylitol.

Chelating Agents

In some embodiments, the compositions of the disclosure contain chelating agents. Non-limiting examples of chelating agents include disodium ethylenediaminetetraacetic acid (EDTA) and tetrasodium EDTA.

UV Absorption Agents

In some embodiments, the compositions of the present disclosure include UV absorption agents. UV absorption agents include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis-diethylamino hydroxybenzoyl benzoate, bis benzoxazoylphenyl ethylhexylimino-triazine, drometrizole tri siloxane, methylene bi s-benzotriazolyl tetramethylbutylphenol, and bi s-ethylhexyloxyphenol methoxyphenyltriazine, 4-methylbenzylidene camphor, and isopentyl-4-methoxycinnamate. Non-limiting examples of physical sunblocks include, kaolin, talc, petrolatum and metal oxides (e.g., titanium dioxide and zinc oxide).

Emollients

In some embodiments, the compositions of the disclosure contain one or more emollients. Emollients are lubricating ingredients that make the skin soft and smooth and help the skin to retain moisture. Non-limiting examples of emollients include vegetable oils, mineral oils, shea butter, cocoa butter, petrolatum, cholesterol, silicone, and animal oils (including emu, mink, and lanolin).

Moisturizing Agent

In some embodiments, the compositions of the disclosure contain moisturizing agents. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *Aloe barbadensis*, *Aloe-barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, *glycine*, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica* limonum) oil, linoleic acid, linolenic acid, macadamia *ternifolia* nut oil, maltitol, *matricaria* (*Chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*Oryza sativa*) bran oil, RNA, rosemary (*Rosmarinus officinalis*) oil, rose oil, safflower (*Carthamus tinctorius*) oil, sage (*salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

Preservatives

In some embodiments, the compositions of the disclosure contain preservatives. Non-limiting examples of preservatives include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid and salts thereof, thimerosal, potassium sorbate, or combinations thereof. In some embodiments, paraben is not included in the formulations of the disclosure.

Thickening Agents

In some embodiments, the compositions of the disclosure contain thickening agents. Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture thereof.

Non-limiting examples of additional thickening agents that can be used in the context of the present invention include carboxylic acid polymers, cross-linked polyacrylate polymers, polyacrylamide polymers, polysaccharides, and gums. Examples of carboxylic acid polymers include cross-linked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid cross-linked with allyl ethers of sucrose or pentaerythritol (e.g., Carbopol™ 900 series from B. F. Goodrich).

Non-limiting examples of cross-linked polyacrylate polymers include cationic and nonionic polymers. Examples are described in U.S. Pat. Nos. 5,100,660; 4,849,484; 4,835,206; 4,628,078; 4,599,379, each of which is incorporated by reference in its entirety for all purposes herein.

Non-limiting examples of polyacrylamide polymers (including nonionic polyacrylamide polymers including substituted branched or unbranched polymers) include polyacrylamide, iso-paraffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose (HPC), hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit. In some embodiments, cellulose is used as a thickener. In some embodiments, hydroxypropylcellulose (HPC) is used as a thickener. In some embodiments, hydroxypropylcellulose has an average molecular weight of 100,000 g/mol. In some embodiments, the topical rofecoxib compositions comprise between about 1% w/w and about 10% w/w HPC, for example, about 1% w/w, about 2% w/w, about 3% w/w, about 4% w/w, about 5% w/w, about 6% w/w, about 7% w/w, about 8% w/w, about 9% w/w, or about 10% w/w HPC. In some embodiments, the topical rofecoxib compositions comprise about 4% w/w HPC. In some embodiments, the rofecoxib topical compositions comprise about 3% w/w HPC.

In some embodiments, PS20 is used as a thickener in the rofecoxib topical composition. In some embodiments, PS80 is used as a thickener in the rofecoxib topical compositions. In some embodiments, PEG is used as a thickener in the rofecoxib topical compositions.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof. In some embodiments, xanthan gum is added to the rofecoxib topical compositions as a thickener.

Silicone Containing Compounds

In some embodiments, the compositions of the disclosure contain a silicone containing compound. In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present disclosure include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present disclosure include those available from General Electric Co., Silicone Products Div., Waterford, N.Y. and SWS Silicones Div. of Stauffer Chemical Co., Adrian, Mich.

Essential Oils

In some embodiments, the compositions of the disclosure contain essential oils. Essential oils include oils derived from herbs, flowers, trees, and other plants. Such oils are typically present as tiny droplets between the plant's cells, and can be extracted by several method known to those of skill in the art (e.g., steam distilled, enfleurage (extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° C. to 240° C. and densities ranging from about 0.759 g/mL to about 1.096 g/mL.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. In some embodiments, the topical compositions comprise spearmint oil. In some embodiments, the topical compositions comprise *eucalyptus* oil.

In some embodiments, the topical compositions described herein comprise between about 0.1% w/w and about 2% w/w, for example, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, or about 2.0% w/w of essential oils. In some embodiments, the topical compositions described herein comprise about 1% w/w essential oils. In some embodiments, the topical compositions described herein comprise about 0.33% w/w spearmint oil. In some embodiments, the topical compositions described herein comprise about 0.67% w/w spearmint oil. In some embodiments, the topical compositions described herein comprise about 0.33% w/w *eucalyptus* oil. In some embodiments, the topical compositions described herein comprise about 0.67% w/w *eucalyptus* oil.

Other essential oils known to those of skill in the art are also contemplated as being useful within the context of the present invention.

Carrier Oils

In some embodiments, the compositions of the disclosure contain carrier oils. Carrier oils are used to dilute essential oils so they can be applied to the skin without side effects. Non-limiting examples of carrier oils include coconut oil (*Cocus nucifera*), black cumin seed oil (*Nigella sativa*), jojoba oil (*Simmondsia chinensis*), evening primrose oil *Oenothera biennis*), rose hip oil (*Rosa mosqueta*), aloe (*Aloe vera*), and grapeseed oil (*Vitus vinifera*). In some embodiments, *Aloe vera* is used as a carrier oil.

Structuring Agents

In some embodiments, the compositions of the disclosure contain structuring agents. Structuring agents, in certain aspects, assist in providing rheological characteristics, which contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

Vitamins and Minerals

In some embodiments, the compositions of the disclosure contain one or more vitamins, minerals, or amino acids. Non-limiting examples of vitamins include vitamin A, ascorbic acid (vitamin C), vitamin D, vitamin E, vitamin K, thiamine, riboflavin, niacin, pantothenic acid, pyridoxine, biotin, folate, cobalamin, and cyanocobalamin. Non-limiting examples of minerals that can be included in the compositions of the present invention include antimony, barium, beryllium, bismuth, boron, bromine, calcium, carbon, cerium, cesium, chloride, chromium, cobalt, copper, dysprosium, erbium, europium, fluorine, gadolinium, gallium, germanium, gold, hafnium, holmium, indium, iodine, iridium, iron, lanthanum, lithium, magnesium, manganese, molybdenum, neodymium, nickel, niobium, osmium, palladium phosphorus, platinum, potassium, praesodymium, rhenium, rhodium, rubidium, ruthenium, samarium, sodium, selenium, silicon, silver, sodium, strontium, sulfur, tantalum, thallium, thorium, tellurium, terbium, thulium, tin, titanium, tungsten, ytterbium, yttrium, zinc, and zirconium. Any soluble salt of these minerals suitable for inclusion edible products can be used, for example, calcium carbonate, calcium citrate, calcium malate, calcium-citrate-malate, calcium gluconate, magnesium citrate, magnesium gluconate, magnesium sulfate, zinc chloride, zinc sulfate, potassium iodide, and copper sulfate.

In some embodiments, the compositions of the disclosure include amino acids. Non-limiting examples of amino acids include alanine, glutamic acid, *glycine*, histidine, isoleucine, leucine, methionine, phenylalanine, serine, threonine, tryptophan, valine, aspartic acid, arginine, asparagine, glutamine, proline, cysteine, and lysine.

In some embodiments, the minerals and amino acids are contained within a product, which is incorporated into the compositions of the disclosure.

Pharmaceutical Ingredients

In some embodiments, the compositions of the disclosure contain pharmaceutical ingredients. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including difluoromethylonithine (DFMO) and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, and wound healing agents. In some embodiments, methyl-4-Hydroxybenzoate is added to the rofecoxib topical compositions. In some embodiments, methyl-4-Hydroxybenzoate is an anti-fungal.

In some embodiments, the pharmaceutical ingredient is a steroid. Non-limiting examples of steroids include dexamethasone, dexamethasone acetate, dexamethasone sodium phosphate, cortisone, cortisone acetate, hydrocortisone, hydrocortisone acetate, hydrocortisone cypionate, sodium hydrocortisone phosphate, prednisol hydrochloroneone acetate, prednisol acetate Prednisolone, Prednisolone Sodium Phosphate, Prednisolone Tebutate, Prednisolone Pivalate, Triamcinolone, Triamcinolone Acetonide, Triamcinolone Hexacetonide, Triamcinolone Diacetate, Methylprednisolone Methylprednisolone Acetate, Sodium Methodotassium Sodium Methionate, Sodium Methionate Diploate betamethasone, betamethasone, disodium phosphate of vetamethasone, sodium phosphate of vetamethasone, betamethasone acetate, disodium phosphate of betamethasone, chloroprednisone acetate, corticosterone, deoxycorticosterone, deoxycorticosterone acetate, deoxymethyrostaone deoxyketol ester, fludrocortisone, fludrocortisone acetate, dichlorisone acetate, fluorohydrocortisone, fluorometolone, fluprednisolone, parametasona, parametasona acetate, androsterone, fluoxymesterone, aldosterone, methandrostenolone, methyrostenedione, methyldostentaone testosterone, testosterone testosterone, testosterone equonates testosterone, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone hydroxyprogesterone, hydroxyprogesterone acetate, normethisterone, pregnenolone, progesterone, ethinyl estradiol, mestranol, dimethisterone, etisterone, ethinodiol diacetate, norethindrone, norethindrone acetate, norethisterone, fluocinolone acetonide, flurandrenolone, succinate hydrocortisone succinate, methylprednisolone sodium, prednisolone sodium phosphate, triamcinolone acetonide, sodium hydroxydione, spironolactone, oxandrolone, oxymetholone, prometholone, testosterone cypionate, testosterone phenylacetate, estradiol cypionate and noretynodrel.

Excipients

In some embodiments, the compositions of the disclosure contain excipients. In some embodiments, the topical composition contains one or more excipients selected from the list consisting of alpha-tocopherol, 1,2,6-hexanetriol, 6-methoxy-2-(4-styryl-3-sulfophenol)-2-h-benzotriazole, acetic acid, acetyltributyl citrate, acrylates copolymer, adhesive tape, alcloxa, alcohol, algeldrate, alkyl aryl sodium sulfonate, allantoin, almond oil, *aloe*, alpha-terpineol, aluminum acetate, aluminum hydroxide, aluminum monostearate, aluminum oxide, aluminum polyester, aluminum silicate, aluminum starch octenylsuccinate, aluminum stearate, aluminum sulfate anhydrous, amaranth, amerchol cab, aminomethylpropanol, ammonia solution, ammonium lauryl sulfate, amphoteric-9, anhydrous citric acid, anhydrous dibasic calcium phosphate, anhydrous trisodium citrate, anoxid sbn, apricot kernel oil peg-6 esters, aquaphor, arlacel, ascorbic acid, ascorbyl palmitate, aseptoform m, beeswax, synthetic, bentonite, benzalkonium chloride, benzethonium chloride, benzocaine, benzoic acid, benzoin resin, benzyl alcohol, beta carotene, betadex, boric acid, butane, butyl alcohol, butyl ester of methyl vinyl ether/maleic anhydride copolymer (125000 mw), butyl methacrylate and methyl methacrylate copolymer (3:1; 150000 mw), butyl stearate, butylated hydroxyanisole, butylated hydroxytoluene, butylene glycol, butylparaben, c13-14 isoparaffin/laureth-7/polyacrylamide, calcium acetate, canada balsam, captan, caramel, carbomer 1382, carbomer copolymer type a (allyl pentaerythritol crosslinked), carbomer copolymer type b (allyl pentaerythritol crosslinked), carbomer homopolymer type a (allyl pentaerythritol crosslinked), carbomer homopolymer type b (allyl pentaerythritol crosslinked), carbomer homopolymer type b (allyl sucrose crosslinked), carbomer homopolymer type c (allyl pentaerythritol crosslinked), carboxymethylcellulose, carboxymethylcellulose sodium, carboxypolymethylene, carnauba wax, carrageenan, carrageenan sodium, castile soap, castor oil, ceteareth-12, ceteareth-15, ceteareth-30, cetearyl alcohol/ceteareth-20, cetearyl ethylhexanoate, ceteth-10, ceteth-2, ceteth-20, ceteth-23, cetostearyl alcohol, cetyl alcohol, cetyl esters wax, cetyl palmitate, chlorobutanol, chlorobutanol hemihydrate, chlorocresol, chloroxylenol, cholesterol, choleth-24, *Chondrus crispus*, citric acid monohydrate, coco diethanolamide, coco monoethanolamide, coco-betaine, coconut acid, coconut oil, cocoyl caprylocaprate, cold cream, collagen, copovidone k25-31, corn oil, crospovidone, cyclomethicone, cyclomethicone 5, cyclomethicone/dimethicone copolyol, d&c green no. 5, d&c red no. 28, d&c red no. 33, d&c yellow no. 10, d&c yellow no. 10-aluminum lake, dehydag wax sx, dehydroacetic acid, dehymuls e, denatonium benzoate, diatomaceous earth, diazolidinyl urea, dichlorobenzyl alcohol, dichlorodifluoromethane, dichlorotetrafluoroethane, diethanolamine, diethyl sebacate, diethylene glycol monoethyl ether, dihydroxyaluminum aminoacetate, diisopropanolamine, diisopropyl adipate, dimethicone 100, dimethicone 350, dimethiconol/trimethylsiloxysilicate crosspolymer (40/60 w/w; 1000000 pa.$), dimethoxane, dimethyl isosorbide, dimethyl sulfoxide, dimethylaminoethyl methacrylate-butyl methacrylate-methyl methacrylate copolymer, dinoseb-ammonium, dipropylene glycol, disodium cocoamphodiacetate, disodium laureth sulfosuccinate, disodium lauryl sulfosuccinate, dmdm hydantoin, docusate sodium, duro-tak 280-2516, duro-tak 87-2070, duro-tak 87-2194, duro-tak 87-2979, edetate calcium disodium, edetate disodium, edetate disodium anhydrous, edetate sodium, edetate trisodium, edetic acid, emulsifying wax, entsufon, entsufon sodium, ethyl acetate, ethyl myristate, ethyl oleate, ethylcellulose, ethylene glycol, ethylene oxide, ethylene-propylene copolymer, ethylene-vinyl acetate copolymers, ethylenediamine, ethylenediamine dihydrochloride, ethylhexyl hydroxystearate, fatty acid esters, fatty acid pentaerythriol ester, fatty acids, FD&C blue no. 1, FD&C blue no. 1—aluminum lake, FD&C blue no. 2, FD&C green no. 3, FD&C red no. 40, FD&C yellow no. 5, FD&C yellow no. 6, ferric oxide red, formaldehyde solution, fragrance 91-122, fragrance 9128-y, fragrance balsam pine no. 5124, fragrance cream no. 73457, fragrance cs-28197, fragrance p o fl-147, fragrance rbd-9819, fragrance soap, fragrance ungerer n5195, gelatin, gluconolactone, glutaral, glycerin, glyceryl 1-stearate, glyceryl isostearate, glyceryl laurate, glyceryl mono and dipalmitostearate, glyceryl monocaprylate, glyceryl monocitrate, glyceryl monostearate, glyceryl oleate, glyceryl oleate/propylene glycol, glyceryl palmitate, glyceryl ricinoleate, glyceryl stearate se, glyceryl stearate/peg stearate, glyceryl stearate/peg-100 stearate, glycol stearate, guar gum, *Hamamelis virginiana* top water, hexylene glycol, high density polyethylene, hyaluronate sodium, hydrocarbon gel, plasticized, hydrochloric acid, hydrogen peroxide, hydrogenated castor oil, hydrogenated soybean lecithin, hydroxyethyl cellulose (2000 mpa·s at 1%), hydroxyethyl cellulose (280 mpa·s at 2%), hydroxyethyl cellulose, unspecified, hydroxypropyl cellulose (110000 wamw), hydroxypropyl cellulose (1600000 wamw), hypromellose 2208 (100000 mpa·s), hypromellose 2208 (4000 mpa·s), hypromellose 2910 (4000 mpa·s), hypromelloses, icodextrin, imidurea, isobutane, isooctyl acrylate/acrylamide/vinyl acetate copolymer, kollidon va 64 polymer, isopropyl alcohol, isopropyl isostearate, isopropyl myristate, isopropyl palmitate, isostearic acid, isostearyl alcohol, kaolin, lactic acid, lactic acid, dl-, lactic acid, l-, lactose, laneth, lanolin, lanolin alcohol-mineral oil, lanolin alcohols, lanolin cholesterols, lanolin oil, lanolin, ethoxylated, lanosterol, lauramine oxide, laureth sulfate, laureth-2, laureth-23, laureth-4, lauric diethanolamide, lauric myristic monoethanolamide, lauric/myristic diethanololamide, lavender oil, lecithin, lemon oil, levomenthol, levulinic acid, light mineral oil, limonene, (+)-, linear tridecyl benzene sulfonate, liquid petroleum, magnesium aluminum silicate, magnesium nitrate, magnesium silicate, magnesium stearate, magnesium sulfate, mannitol, medical antiform a-f emulsion, medium-chain triglycerides, *Mentha spicata* oil, menthol, metanil yellow, methyl gluceth-10, methyl gluceth-20, methyl glucose sesquistearate, methyl laurate, methyl salicylate, methyl stearate, methylcellulose, methylchloroisothiazolinone, methylchloroisothiazolinone/methylisothiazolinone mixture, methylparaben, microcrystalline wax, mineral oil, mono and diglyceride, multisterol extract, myristyl alcohol, myristyl lactate, niacinamide, nitric acid, nonoxynol-40, nonoxynol-9, o-tolyl biguanide, octisalate, octoxynol-9, octyldodecanol, oleic acid, oleth-10/oleth-5, oleth-2, oleth-20, oleyl alcohol, oleyl oleate, olive oil, palm oil, paraffin, parfum creme 45/3, peanut oil, peg 6-32 stearate/glycol stearate, peg-100 stearate, peg-120 glyceryl stearate, peg-120 methyl glucose dioleate, peg-2 stearate, peg-20 methyl glucose sesquistearate, peg-20 sorbitan isostearate, peg-25 propylene glycol stearate, peg-5 oleate, peg-6 isostearate, peg-60 hydrogenated castor oil, peg-7 methyl ether, peg-75 lanolin, peg-8 laurate, peg-8 stearate, peg/ppg-18/18 dimethicone, pegoxol 7 stearate, pentadecalactone, pentasodium pentetate, peppermint oil, perfume gd 5604, petrolatum, phenonip, phenoxyethanol, phenylethyl alcohol, phenylmercuric acetate, phosphoric acid, pigmented polyethylene/polyester 1501 film, pine needle oil (*Pinus sylvestris*), plastibase-50w, poloxamer 124, poloxamer 182, poloxamer 188, poloxamer 407, polyacrylic acid (250000 mw), polybutene (1400 mw), polycarbophil, polyester, polyester polyamine copolymer, polyethylene glycol 1000, polyethylene glycol 1450, polyethylene glycol 1600, polyethylene glycol 200, polyethylene glycol 300, polyethylene glycol 3350, polyethylene glycol 400, polyethylene glycol 4000, polyethylene glycol 540, polyethylene glycol 600, polyethylene glycol 6000, polyethylene glycol 8000, polyethylene glycol 900, polyglyceryl-3 oleate, polyisobutylene, polyisobutylene/polybutene adhesive, polyoxyethylene alcohols, polyoxyethylene fatty acid esters, polyoxyl 20 cetostearyl ether, polyoxyl 35 castor oil, polyoxyl 40 hydrogenated castor oil, polyoxyl 40 stearate, polyoxyl 6 and polyoxyl 32 palmitostearate, polyoxyl distearate, polyoxyl glyceryl stearate, polyoxyl stearate, polypropylene, polypropylene glycol, polyquaternium-10, polysorbate 20, polysorbate 40, polysorbate 60, polysorbate 80, polyvinyl alcohol, ponceau 3r, potassium carbonate, potassium chloride, potassium citrate, potassium hydroxide, potassium soap, potassium sorbate, povidone k30, povidone k90, povidone/eicosene copolymer, povidones, powdered cellulose, ppg-12/smdi copolymer, ppg-15 stearyl ether, ppg-20 methyl glucose ether distearate, ppg-26 oleate, promulgen d, promulgen g, propane, propionic acid, propyl alcohol, propyl gallate, propylene carbonate, propylene glycol, propylene glycol diacetate, propylene glycol dicaprylate, propylene glycol monolaurate, propylene glycol monopalmitostearate, propylene glycol monostearate, propylparaben, protein hydrolysate, quaternium-15, quaternium-15 cis-form, rhodamine b, saccharin, saccharin sodium, scotchpak 1022, sd alcohol 40, sd alcohol 40-2, sd alcohol 40b, sepineo p 600, silicon, silicon dioxide, silicone, silicone adhesive 4302, silicone emulsion, silicone/polyester film strip, simethicone, simethicone emulsion, soap, sodium acetate, sodium acetate anhydrous, sodium alginate, sodium benzoate, sodium bisulfite, sodium borate, sodium carbonate, sodium cetostearyl sulfate, sodium chloride, sodium cocoyl isethionate, sodium formaldehyde sulfoxylate, sodium hydroxide, sodium iodide, sodium lactate, sodium laureth-2 sulfate, sodium laureth-3 sulfate, sodium laureth-5 sulfate, sodium lauroyl sarcosinate, sodium lauryl sulfate, sodium lauryl sulfoacetate, sodium metabisulfite, sodium metaphosphate, insoluble, sodium methyl cocoyl taurate, sodium phosphate, sodium phosphate, dibasic, sodium phosphate, dibasic, anhydrous, sodium phosphate, dibasic, dihydrate, sodium phosphate, dibasic, heptahydrate, sodium phosphate, monobasic, sodium phosphate, monobasic, anhydrous, sodium phosphate, monobasic, dihydrate, sodium phosphate, monobasic, monohydrate, sodium polyacrylate, sodium pyrrolidone carboxylate, sodium silicate, sodium sulfate, sodium sulfate anhydrous, sodium sulfite, sodium tallowate, beef, sodium thiosulfate, sorbic acid, sorbitan monolaurate, sorbitan monooleate, sorbitan monopalmitate, sorbitan monostearate, sorbitan sesquioleate, sorbitan tristearate, sorbitol, soybean, soybean oil, spermaceti, squalane, stannic chloride, stannous chloride anhydrous, starch, stearalkonium chloride, stearamidoethyl diethylamine, steareth-10, steareth-100, steareth-2, steareth-21, steareth-40, stearic acid, stearic diethanolamide, stearic hydrazide, stearoyl polyoxylglycerides, stearyl alcohol, styrene/isoprene/styrene block copolymer, succinic acid, sucrose, sucrose stearate, sulfuric acid, talc, tallow glycerides, tartaric acid, tegacid, tenox, tenox-2, tert-butyl alcohol, thimerosal, thyme oil, titanium dioxide, tocopherol, tragacanth, triacetin, trichloromonofluoromethane, trideceth-10, triethanolamine lauryl sulfate, trihydroxy stearin, trimethylsilyl treated dimethiconol/trimethylsiloxysilicate crosspolymer (40/60 w/w; 5000000 pa.$), trimethylsilyl treated dimethiconol/trimethylsiloxysilicate crosspolymer (45/55 w/w; 100000 pa.$), tri sodium citrate dihydrate, trisodium hedta, trolamine, tromethamine, tyloxapol, undecylenic acid, urea, vanillin, vegetable oil, vegetable oil, hydrogenated, wax, wecobee fs, white wax, xanthan gum, yellow wax, zinc acetate, zinc oxide, and zinc stearate.

Antioxidants

In some embodiments, the compositions of the disclosure contain antioxidants. Antioxidants are substances that inhibit oxidation. Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, butated hydroxyanisole (BHA), butylated hydroxytoluene (BHT), t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Other Ingredients

In some embodiments, sorbitol is added to the rofecoxib topical compositions described herein. In some embodiments, sorbitol is a hydrator. In some embodiments, sorbitol is a moisturizer. In some embodiments, sorbitol is a humectant. In some embodiments, polyvinyl alcohol is added to the rofecoxib topical compositions described herein. In some embodiments, polyvinyl alcohol is used to increase the viscosity of the rofecoxib topical composition. In some embodiments, 2-hydroxyethyl stearate is added to the rofecoxib topical compositions. In some embodiments, 2-hydroxyethyl stearate is used to give the rofecoxib topical composition a waxy feel. In some embodiments, cetyl alcohol is added to the rofecoxib topical compositions described herein. In some embodiments, cetyl alcohol is a thickener. In some embodiments, cetyl alcohol is an emulsifier. In some embodiments, glycerol monsterate is added to the rofecoxib topical compositions described herein. In some embodiments, glycerol monsterate is a thickener. In some embodiments, glycerol monostearate is an emulsifier. In some embodiments, beeswax is used in the rofecoxib topical compositions described herein. In some embodiments, beeswax is used as a thickener. In some embodiments, urea is added to rofecoxib topical compositions. In some embodiments, urea is added as an emollient or a penetration agent.

In some embodiments, OA is added to the topical composition as a penetration enhancer, or a reagent which facilitates entry of rofecoxib into the skin. In some embodiments, PGD is added to the topical composition as a penetration enhancer. In some embodiments, DGME is added to the topical composition as a penetration enhancer. In some embodiments, sodium dodecyl sulfate (SDS) is added to the compositions. In some embodiments, SDS serves as a penetration enhancer. In some embodiments, menthol is added to the rofecoxib topical compositions. In some embodiments, menthol is a penetration enhancer or enhances the smell of the rofecoxib topical compositions. In some embodiments, beeswax is added to the rofecoxib topical compositions. In some embodiments, beeswax is a thickener. In some embodiments, beeswax is a penetration enhancer. In some embodiments, polyethylene glycol is added to the compositions. Polyethylene glycol is an oligomer or polymer of ethylene oxide. In some embodiments, the PEG is selected from polyethylene glycol 400, polyethylene glycol 350, polyethylene glycol 3350, polyethylene glycol 4000, polyethylene glycol 1500, polyethylene glycol 6000, and polyethylene glycol 8000.

In some embodiments, the rofecoxib topical composition comprises spearmint oil. In some embodiments, the spearmint oil is an extract of *Mentha spicata*.

In some embodiments, the rofecoxib topical composition comprises AC, BA, and Rofecoxib. In some embodiments, the rofecoxib topical composition comprises DI, PC, and Rofecoxib. In some embodiments, the rofecoxib topical composition comprises DI, PC, BA, and Rofecoxib. In some embodiments, the rofecoxib topical composition comprises DI, PC, DMSO, BA, and Rofecoxib. In some embodiments, the rofecoxib topical composition comprises DI, PC, BA, DMSO, and Rofecoxib. In some embodiments, the rofecoxib topical composition comprises DI, PC, BA, OA, and Rofecoxib. In some embodiments, the rofecoxib topical composition comprises DI, PC, BA, DMSO, AT, and Rofecoxib. In some embodiments, the rofecoxib topical composition comprises DI, PC, BA, DGME, DMSO, and Rofecoxib. In some embodiments, the rofecoxib topical composition comprises DI, PC, BA, DMSO, OA, and Rofecoxib. In some embodiments, the rofecoxib topical composition comprises DI, PC, BA, DMSO, PS-20, and Rofecoxib. In some embodiments, the rofecoxib topical composition comprises DI, PC, BA, DMSO, PS20, and Rofecoxib. In some embodiments, the rofecoxib topical composition comprises DI, PC, BA, DMSO, PS60, and Rofecoxib. In some embodiments, the rofecoxib topical composition comprises DI, PC, BA, OA, DMSO, and Rofecoxib. In some embodiments, the rofecoxib topical composition comprises DI, DMSO, PC, BA, Lanolin, PPG, and Rofecoxib. In some embodiments, the rofecoxib topical composition comprises DI, DMSO, PC, BA, Lanolin, PEG-400, and Rofecoxib. In some embodiments, the rofecoxib topical composition comprises DI, DMSO, PC, BA, Lanolin, MineralOil, and Rofecoxib. In some embodiments, the rofecoxib topical composition comprises DI, DMSO, PC, BA, Petroleum, MineralOil, and Rofecoxib. In some embodiments, the rofecoxib topical composition comprises DI, PC, BA, AT, OA, DMSO, and Rofecoxib. In some embodiments, the rofecoxib topical composition comprises DI, PC, BA, DGME, DMSO, OA, and Rofecoxib. In some embodiments, the rofecoxib topical composition comprises DI, PC, BA, DGME, DMSO, AT, and Rofecoxib. In some embodiments, the rofecoxib topical composition comprises DI, PC, BA, OA, PS20, DMSO, and Rofecoxib. In some embodiments, the rofecoxib topical composition comprises DI, PC, BA, DMSO, PS80, OA, and Rofecoxib. In some embodiments, the rofecoxib topical composition comprises DI, PC, BA, DMSO, PS60, OA, and Rofecoxib. In some embodiments, the rofecoxib topical composition comprises DI, PC, BA, OA, DMSO, PEG, and Rofecoxib. In some embodiments, the rofecoxib topical composition comprises DI, PC, BA, DMSO, OA, PEG, and Rofecoxib. In some embodiments, the rofecoxib topical composition comprises DI, DMSO, PC, BA, Lanolin, Mineral Oil, PBS/Xanthan Gum, and Rofecoxib. In some embodiments, the rofecoxib topical composition comprises DI, PC, BA, AT, OA, PS20, DMSO, and Rofecoxib. In some embodiments, the rofecoxib topical composition comprises DI, PC, BA, DGME, OA, PS20, DMSO, and Rofecoxib. In some embodiments, the rofecoxib topical composition comprises DI, PC, BA, OA, DMSO, Glycerol monostearate, Mineral Oil, and Rofecoxib. In some embodiments, the rofecoxib topical composition comprises DI, PC, BA, OA, DMSO, Lanoline, and Rofecoxib. In some embodiments, the rofecoxib topical composition comprises DI, PC, BA, OA, DMSO, Lanoline, OliveOil, and Rofecoxib. In some embodiments, the rofecoxib topical composition comprises DI, PC, BA, OA, DMSO, Lanoline, OliveOil, and Rofecoxib. In some embodiments, the rofecoxib topical composition comprises DI, PC, DMSO, BA, OleicAcid, Lanolin, Mineral Oil, and Rofecoxib. In some embodiments, the rofecoxib topical composition comprises DI, PC, BA, DMSO, OA, PEG, Lanoline, and Rofecoxib. In some embodiments, the rofecoxib topical composition comprises DI, PC, BA, DMSO, OA, PEG, IPTD, and Rofecoxib. In some embodiments, the rofecoxib topical composition comprises DI, PC, BA, DMSO, OA, PEG, PGD, and Rofecoxib. In some embodiments, the rofecoxib topical composition comprises DI, PC, BA, DMSO, OA, PEG, PS80, and Rofecoxib. In some embodiments, the rofecoxib topical composition comprises DI, PC, BA, DMSO, OA, PEG, PPG, and Rofecoxib. In some embodiments, the rofecoxib topical composition comprises DI, PC, BA, DMSO, OA, PEG, PS20, and Rofecoxib. In some embodiments, the rofecoxib topical composition comprises DI, PC, BA, DMSO, OA, PEG, EA, and Rofecoxib. In some embodiments, the rofecoxib topical composition comprises DI, PC, BA, DMSO, OA, PEG, DGME, and Rofecoxib. In some embodiments, the rofecoxib topical composition comprises DI, PC, BA, DMSO, OA, PEG, Alpha-Terpinol, and Rofecoxib. In some embodiments, the rofecoxib topical composition comprises DI, PC, BA, DMSO, OA, PEG, DIA, and Rofecoxib. In some embodiments, the rofecoxib topical composition comprises DI, PC, BA, DMSO, OA, PEG, DS, and Rofecoxib. In some embodiments, the rofecoxib topical composition comprises DI, PC, BA, DMSO, OA, PEG, M24D, and Rofecoxib. In some embodiments, the rofecoxib topical composition comprises DI, PC, BA, DMSO, OA, PEG, Mineral Oil, and Rofecoxib. In some embodiments, the rofecoxib topical composition comprises DI, PC, BA, DMSO, OA, DIA, PEG, and Rofecoxib. In some embodiments, the rofecoxib topical composition comprises DI, PC, BA, DMSO, OA, DIA, PEG, and Rofecoxib. In some embodiments, the rofecoxib topical composition comprises DI, PC, BA, DMSO, EA, DIA, OA, and Rofecoxib. In some embodiments, the rofecoxib topical composition comprises DI, PC, BA, DMSO, DIA, PS20, DGME, and Rofecoxib. In some embodiments, the rofecoxib topical composition comprises DI, PC, BA, DMSO, DIA, PS20, PG, and Rofecoxib. In some embodiments, the rofecoxib topical composition comprises DI, PC, BA, DGME, DMSO, AT, OA, DGME, and Rofecoxib. In some embodiments, the rofecoxib topical composition comprises DI, PC, BA, DGME, AT, OA, PS20, DMSO, and Rofecoxib. In some embodiments, the rofecoxib topical composition comprises DI, PC, BA, OA, DMSO, Beeswax, Lanoline, MineralOil, and Rofecoxib. In some embodiments, the rofecoxib topical composition comprises DI, PC, DMSO, BA, OA, Lanolin, Mineral Oil, BeesWax, and Rofecoxib. In some embodiments, the rofecoxib topical composition comprises DI, PC, BA, DMSO, OA, Lanolin, Mineral Oil, BeesWax, and Rofecoxib. In some embodiments, the rofecoxib topical composition comprises Rofecoxib, DI, PC, BA, DMSO, OA, Lanolin, Min.Oil, and BeesWax. In some embodiments, the rofecoxib topical composition comprises Rofecoxib, DI, PC, BA, DMSO, OA, Lanolin, Min.Oil, and BeesWax. In some embodiments, the rofecoxib topical composition comprises DI, PC, BA, DMSO, OA, PEG, IPTD, SDS, and Rofecoxib. In some embodiments, the rofecoxib topical composition comprises DI, PC, BA, DMSO, OA, PEG, PGD, Lanoline, and Rofecoxib. In some embodiments, the rofecoxib topical composition comprises DI, PC, BA, DMSO, OA, PEG, BeesWax, PS80, and Rofecoxib. In some embodiments, the rofecoxib topical composition comprises DI, PC, BA, DMSO, OA, DIA, PEG, Rofecoxib, and. In some embodiments, the rofecoxib topical composition comprises DI, PC, BA, DMSO, EA, DIA, AT, OA, and Rofecoxib. In some embodiments, the rofecoxib topical composition comprises DI, PC, BA, DMSO, DIA, PS20, DGME, OA, and Rofecoxib. In some embodiments, the rofecoxib topical composition comprises DI, PC, BA, DMSO, DIA, PS20, AT, DGME, and Rofecoxib. In some embodiments, the rofecoxib topical composition comprises DI, PC, BA, DMSO, DIA, PS20, OA, PPG, and Rofecoxib. In some embodiments, the rofecoxib topical composition comprises DI, PC, BA, DMSO, DIA, PS20, PGD, DGME, and Rofecoxib. In some embodiments, the rofecoxib topical composition comprises DI, PC, BA, DMSO, DIA, PS20, PGD, AT, and Rofecoxib. In some embodiments, the rofecoxib topical composition comprises DI, PC, BA, DMSO, DIA, PS20, PGD, AT, and Rofecoxib. In some embodiments, the rofecoxib topical composition comprises DI, PC, BA, DMSO, DIA, PS20, AT, DGME, and Rofecoxib. In some embodiments, the rofecoxib topical composition comprises DI, PC, BA, DMSO, EA, DIA, Rofecoxib, PS20, and Menthol. In some embodiments, the rofecoxib topical composition comprises DI, PC, BA, DMSO, DIA, PS20, PGD, OA, DGME, and Rofecoxib. In some embodiments, the rofecoxib topical composition comprises DI, PC, BA, DMSO, DIA, PS20, AT, OA, DGME, and Rofecoxib. In some embodiments, the rofecoxib topical composition comprises DI, PC, BA, DMSO, DIA, PS20, PGD, AT, DGME, and Rofecoxib. In some embodiments, the rofecoxib topical composition comprises DI, PC, BA, DMSO, DIA, PS20, PGD, AT, DGME, and Rofecoxib. In some embodiments, the rofecoxib topical composition comprises DI, PC, BA, DMSO, EA, Rofecoxib, DIA, AT, BeesWax, Menthol, and *Eucalyptus*. In some embodiments, the rofecoxib topical composition comprises DI, PC, BA, DMSO, DIA, PS20, PGD, OA, DGME, Rofecoxib, and Lanoline.

In some embodiments, the rofecoxib topical composition is selected from Table 5. In some embodiments, the rofecoxib topical composition is selected from Formulations 1-77, 80, 82, 83, and 85-93.

In some embodiments, the rofecoxib topical composition is Formulation 82. Formulation 82 comprises DI (15% w/w), PC (5% w/w), BA (2.5% w/w), DMSO (20% w/w), DIA (12% w/w), PS20 (15% w/w), DGME (18.5% w/w), OA (5% w/w), Rofecoxib (2% w/w), Spearmint (0.33% w/w), and *Eucalyptus* oil (0.67% w/w).

In some embodiments, the rofecoxib topical composition is Formulation 85. Formulation 85 comprises DI (15% w/w), PC (5% w/w), BA (2.5% w/w), DMSO (20% w/w), DIA (12% w/w), DGME (18.5% w/w), PS20 (15% w/w), OA (5% w/w), Hydoxypropyl cellulose 100,000 (4% w/w), Rofecoxib 2% (2% w/w), *Eucalyptus* Oil (0.33% w/w), and Spearmint Oil (0.67% w/w).

Properties and Stability of Rofecoxib Topical Compositions

In some embodiments, the compositions of the disclosure are stable for about 6 or more months. In some embodiments, the compositions of the disclosure are stable for about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 25 months, about 26 months, 27 months, about 28 months, about 29 months, about 30 months, about 31 months, about 32 months, about 33 months, about 34 months, about 35 months, about 36 months, about 37 months, about 38 months, about 39 months, about 40 months, about 41 months, about 42 months, about 43 months, about 44 months, about 45 months, about 46 months, about 47 months, about 48 months, about 5 years, about 6 years, about 7 years, about 8 years, about 9 years, about 10 years, or more, including all values and ranges in between. In some embodiments, the compositions of the disclosure are stable for at least 6 months. In some embodiments, the compositions of the disclosure are stable for at least 24 months.

In some embodiments, a stable composition of the disclosure is yellow. In some embodiments, a stable composition of the disclosure is light yellow.

In some embodiments, the compositions of the disclosure are stable from about pH 3.5 to about pH 8.5. In some embodiments, the rofecoxib topical compositions are stable at about pH 3.5, about pH 4.0, about pH 4.5, about pH 5.0, about pH 5.5, about pH 6.0, about pH 6.5, about pH 7.0, about pH 7.5, about pH 8.0, or about pH 8.5, including all values and ranges in between.

In some embodiments, the compositions of the disclosure are stable at a temperature range from about 0° C. to about 50° C. In some embodiments, the compositions of the disclosure are stable at about 25° C. In some embodiments, the compositions of the disclosure are stable at about 30° C. In some embodiments, the compositions of the disclosure are stable at about 35° C. In some embodiments, the compositions of the disclosure are stable at about 40° C. In some embodiments, the compositions of the disclosure are stable at about 45° C. In some embodiments, the compositions of the disclosure are stable at about 50° C.

In some embodiments, a stable rofecoxib topical composition refers to a composition in which rofecoxib does not appreciably precipitate. In some embodiments, a stable rofecoxib topical composition refers to a composition in which >95% of rofecoxib does not precipitate. In some embodiments, a stable rofecoxib topical composition refers to a composition in which >90% of rofecoxib does not precipitate. Alternatively stated, a stable rofecoxib topical composition refers to a composition with less than about 5%, less that about 4%, less than about 3%, less than about 2%, less than about 1%, less than about 0.5%, or less than about 0.1% undissolved rofecoxib (relative to the total amount of rofecoxib in the composition). In other embodiments, a stable formulation refers to a formulation which does not separate into separate phases.

In some embodiments, the rofecoxib topical compositions provided herein are sufficiently bodied such that the product does not fall off the targeted dosing area. In some embodiments, the rofecoxib topical compositions provided herein do not run-off the application site until the topical composition is rubbed in to the skin. In some embodiments, the rofecoxib topical compositions provided herein penetrate the skin.

In some embodiments, the flux of the rofecoxib topical compositions described herein is superior to other NSAIDS, including ibuprofen, diclofenac, celecoxib, diflunisal, indomethacin, aspirin, naproxen, oxaprozin, piroxican, salsalate, sulindac, and tolmetin. In some embodiments, the flux of the rofecoxib topical compositions described herein is superior to diclofenac. In some embodiments, application of the rofecoxib topical compositions described herein to the skin treat pain more effectively than diclofenac. In some embodiments, application of the rofecoxib topical compositions described herein to the skin treat inflammation more effectively than diclofenac. In some embodiments, application of the rofecoxib topical composition results in a higher penetration amount into the blood than diclofenac. 0.067 mg of diclofenac penetrates into the blood after 24 hours after 25 hours.

In some embodiments, the rofecoxib topical compositions described herein are non-irritating. In some embodiments, the rofecoxib topical compositions described herein are suitable for chronic use.

Products Containing Rofecoxib Topical Compositions

In some embodiments, the rofecoxib topical compositions of the disclosure are mixed with a vehicle to form a product. Methods of preparing products for topical administration are known in the art (see, for example, Remington's Pharmaceutical Sciences, 2000-20th edition, and The United States Pharmacopeia: The National Formulary, USP 24 NF19, published in 1999, which is incorporated by reference in its entirety herein).

In some embodiments, the vehicle is utilized to facilitate delivery of the rofecoxib topical composition to the skin. Non-limiting examples of vehicles include liposomes, nanosomes, emulsions, microemulsions, nanocapsules, solid lipid nanoparticles, hydrogels, and nanocrystals. The vehicle may contain any ingredient listed throughout this disclosure.

In some embodiments, the vehicle is a liposome. Liposomes are vesicular structures, which have an aqueous core enclosed by a lipid bilayer. In some embodiments, liposomes contain phospholipids or fatty acids. In some embodiments, liposomes range in size from 15 nm in diameter to several micrometers in diameter. In some embodiments, liposomes exhibit a unilamellar structure or a multilamellar structure. Liposomes facilitate the continuous supply of active ingredients or additional ingredients to cells over a sustained period of time.

In some embodiments, the vehicle is an emulsion. An emulsion is a dispersed system containing at least two immiscible liquid phases, one of which is dispersed in the form of small droplets throughout the other, and an emulsifying agent to improve the stability of the system. Non-limiting examples of emulsions include water-in-oil emulsions, oil-in-water emulsions, and oil-in-oil emulsions. Non-limiting examples of emulsifying agents include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, polysorbate 21, polysorbate 61, polysorbate 81, polysorbate 85, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

In some embodiments, "oil" signifies the oil phase of an emulsion. Non-limiting examples of oils which may be utilized within the oil phase include hydrocarbon oils of animal origin and hydrocarbon oils of vegetable origin. Non-limiting examples of hydrocarbon oils of vegetable origin include liquid triglycerides of fatty acids comprising 4 to 10 carbon atoms such as triglycerides of heptanoic or octanoic acids or also, for example, sunflower, corn, and soy, pumpkin, grape seeds, sesame, hazelnut, apricot, macadamia, arara, sunflower, castor, avocado, and triglycerides of caprylic/capric acids. In some embodiments, the oil phase of the emulsion contains from about 10% w/w to about 90% w/w. In some embodiments, the oil phase of the emulsion is about 5 w/w, or about 10% w/w, or about 15 w/w, or about 20% w/w, or about w/w, or about 30% w/w, or about 35 w/w, or about 40% w/w, or about 45% w/w, or about 50% w/w, or about 55% w/w, or about 60% w/w, or about 65% w/w, or about 70% w/w, or about 75% w/w, or about 80% w/w, or about 85% w/w, or about 90% w/w.

In some embodiments, "water" signifies the water phase of an emulsion. In some embodiments, the water phase of the emulsion contains from about 10% w/w to about 90% w/w. In some embodiments, the water phase of the emulsion is about 5% w/w, or about 10% w/w, or about 15% w/w, or about 20% w/w, or about 25% w/w, or about 30% w/w, or about 35% w/w, or about 40% w/w, or about 45% w/w, or about 50% w/w, or about 55% w/w, or about 60% w/w, or about 65% w/w, or about 70% w/w, or about 75% w/w, or about 80% w/w, or about 85% w/w, or about 90% w/w.

In some embodiments, the rofecoxib topical compositions of the disclosure are incorporated into a lotion, ointment, cream, gel, suspension, powder, or any other type of liquid or solid compositions used for topical application.

Methods of Using Rofecoxib Topical Compositions

In some embodiments, the rofecoxib topical compositions of the disclosure are used for treating inflammation and/or pain.

In some embodiments, the rofecoxib topical compositions of the disclosure are administered topically to the skin.

In some embodiments, the rofecoxib topical compositions described herein are applied topically to a subject's skin. In some embodiments, the subject is a mammal. In some embodiments, the subject is an animal or a human. Non-limiting examples of animals include dogs, cats, wolves, bears, tigers, lions, monkeys, guinea pigs, ferrets, pigs, hamsters, and rabbits.

In some embodiments, the rofecoxib topical compositions are applied to the skin. In some embodiments, the compositions of the disclosure are applied to the epidermis. In some embodiments, the compositions of the disclosure penetrate the dermis. In some embodiments, the compositions of the disclosure penetrate the hypodermis. In some embodiments, the compositions of the disclosure are applied to the face, scalp, hands, neck, décolleté, scalp, paw, hand, palm, arm, leg, foot, sole, chest, breast, back, abdomen, buttock, vulva, eyelid, nipples, penis, scrotum, anus, or any other skin areas of a subject. In some embodiments, the compositions of the disclosure are applied to the lips. In some embodiments, the composition is applied to the whole body.

In some embodiments, the rofecoxib topical compositions are applied as a lotion, ointment, cream, gel, suspension, powder, or any other type of liquid or solid compositions used for topical application.

In some embodiments, the rofecoxib topical compositions are left on the skin for a period of at least 1 minute, or at least 2 minutes, or at least 3 minutes, or at least 4 minutes, or at least 5 minutes, or at least 6 minutes, or at least 7 minutes, or at least 8 minutes, or at least 9 minutes, or at least 10 minutes, or at least 15 minutes, or at least 20 minutes, or at least 25 minutes, or at least 30 minutes, or at least 45 minutes, or at least 1 hour, or at least 12 hours, or up to 24 hours, including all ranges in between.

In some embodiments, the rofecoxib topical compositions are applied one or more times per day. In some embodiments, the compositions are applied once per day. In some embodiments, the compositions are applied twice per day. In some embodiments, the compositions are applied twice a day, or three times a day, or four time a day, or more. In some embodiments, the compositions are applied every day, or every other day, or every third day, or every fourth day, or every fifth day, or every sixth day, or once per week.

In some embodiments, the rofecoxib topical compositions are suitable for long-term use. In some embodiments, rofecoxib topical compositions are utilized at least once a week for two weeks or more. In some embodiments, rofecoxib topical compositions are utilized for at least about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 3 months, about 4 months, about 5 months, about 6 months, about 7 months, about 8 months, about 9 months, about 10 months, about 11 months, about 12 months, about 2 years, about 3 years or more.

In some embodiments, the rofecoxib topical compositions are applied when a subject experiences pain. In some embodiments, the rofecoxib topical compositions are applied when a subject experiences inflammation. In some embodiments, the rofecoxib topical compositions are applied prophylactically, e.g. to prevent future pain or inflammation.

In some embodiments, application of a rofecoxib topical composition results in pain relief. In some embodiments, application of a rofecoxib topical composition results in relief from chronic pain. In some embodiments, application of a rofecoxib topical composition results in relief from acute pain.

In some embodiments, the rofecoxib topical compositions are used to treat one or more diseases selected from the group consisting of arthritis, osteoarthritis, juvenile rheumatoid arthritis, joint pain due to injury e.g. ankle sprains, sports injuries, carpal tunnel syndrome, ankle sprains, rheumatoid arthritis, inflammation, low back pain, ankylosing spondylitis, psoriatic arthritis, tennis elbow, headache, and migraine.

EXAMPLES

Example 1. Determination of Solubility of Rofecoxib in Various Solvent Systems

The solubility of rofecoxib was tested in a variety of solvent systems by UV spectrophotometry. A UV spectrophotometry method of evaluating the solubility of rofecoxib was used to determine the solubility of rofecoxib in various solvent systems. Erk et al. describes this method and is incorporated by reference herein in its entirety: Erk et al. Pharmazie. 2004 June; 59(6):453-6.

General Methods: Calculating the Extinction Coefficient of Rofecoxib:

100 mg of rofecoxib was dissolved in 100 ml of methanol. Dilutions of the stock solution were made into methanol to give a final rofecoxib concentration of 5 µg/ml, 10 µg/ml, 20 µg/ml, 25 µg/ml, 30 µg/ml, 35 µg/ml, 40 µg/ml, 45 µg/ml, and 50 µg/ml. A UV spectrophotometer was utilized to read the absorbance of the samples 279.1 nm. Using Beer's law, a value for the extinction coefficient for rofecoxib was obtained. The value of the extinction coefficient of rofecoxib was determined to be 29.06 and was utilized in future experiments to determine the concentration of rofecoxib in various solvent systems. FIG. 1 shows the experimental data for calculation of the extinction coefficient.

Solvent Systems Comprising Single Solvents:

100 mg of rofecoxib was added to 1 gram of each solvent. If the solubility of rofecoxib in the solvent was higher than 100 mg/g, an additional 100 mg of rofecoxib was added to the solution. The mixtures of rofecoxib and solvents were vortexed for one minute and left at room temperature for one hour. The mixture was vortexed a second time and then left at room temperature overnight. The next morning the samples were vortexed a third time and then centrifuged at 12 k for 5 minutes. The excipient/rofecoxib mixture was transferred to a new tube being careful to not take any of the pellet. Serial dilutions of the rofecoxib solvent solutions were made (1:100 v:v), (1:1000 v/v), and (1:2000 v/v). Solvents without rofecoxib were diluted with methanol and used to blank a Beckman DU-7400 spectrophotometer. The absorbance of the samples was determined at a wavelength of 279.1 nm. The concentration of rofecoxib dissolved in the solvent was calculated using Beer's Law. Concentrations were converted from units of mg/mL to units of mg/g according to the following procedure:

(a) The volume of 1 g of solvent times the calculated mg/ml rofecoxib equals total mg of rofecoxib in 1 g of solvent. e.g. 1 g of a solvent that has a density of 1.05 g/mL is 952 µL. A rofecoxib solution with a concentration of rofecoxib of 29.06 mg/mL contains 28.17 mg of rofecoxib in 952 µL of solvent.

(b) To calculate the total volume, a mg of rofecoxib is assumed to equal to 1 µl of volume. Add volume of the solvent to the total weight of rofecoxib. 28.17 mg+1000 mg of solvent=1028.17 mg.

(c) To calculate the w/w divide the mg of rofecoxib 28.71 mg by the total weight of rofecoxib with solvent 1028.71 mg and multiply times 1000 mg to get the w/w 2.871 mg/1028.71 mg*1000 mg=28.62 mg/g of solvent.

Figure 2:
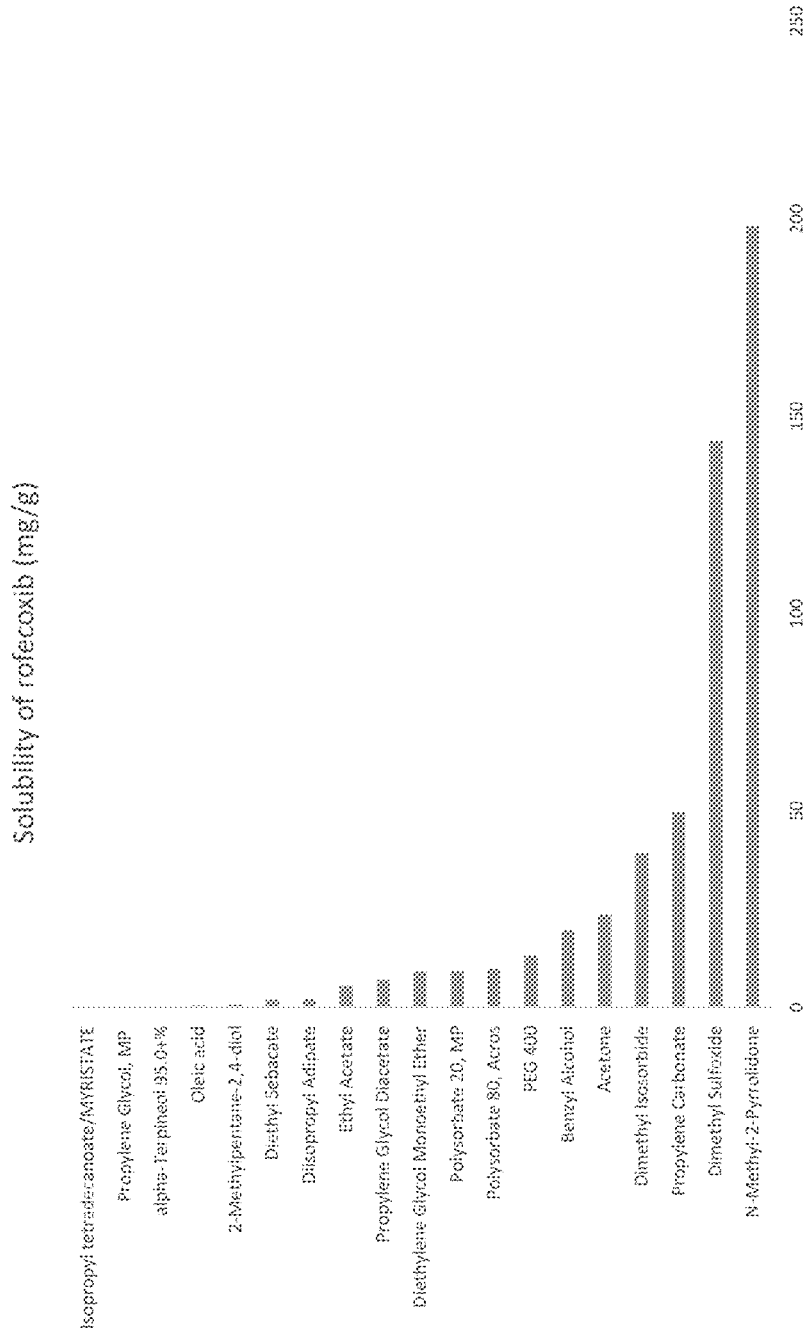
FIG. 2 shows the solubility of rofecoxib in solvent systems containing one solvent.

The solubility of rofecoxib in various solvents is shown in Table 2 and FIG. 2.

TABLE 2

Solubility of Rofecoxib in Solvent Systems containing one solvent

| Solvent | Solubility of rofecoxib (mg/g) |
|---|---|
| N-methyl-2-pyrrolidone | 198 |
| Dimethyl Sulfoxide | 143.6 |
| Propylene Carbonate | 49.43 |
| Dimethyl Isosorbide | 39.14 |
| Acetone | 23.58 |

TABLE 2-continued

Solubility of Rofecoxib in Solvent Systems containing one solvent

| Solvent | Solubility of rofecoxib (mg/g) |
|---|---|
| Benzyl Alcohol | 19.54 |
| Polyethylene glycol-400 (PEG) | 13.14 |
| Polysorbate 80 (PS80) | 9.71 |
| Polysorbate 20 (PS20) | 9.18 |
| Diethylene glycol monoethyl ether | 9.07 |
| Propylene glycol diacetate | 6.93 |
| Ethyl acetate | 5.5 |
| Diisopropyl adipate | 2.04 |
| Diethyl sebacate | 1.3 |
| 2-Methylpentane-2,4-diol | 0.59 |
| Oleic acid | 0.402 |
| alpha-Terpineol 95.0+ % | 0.313 |
| Propylene Glycol | 0.302 |
| Isopropyl tetradecanoate | 0.0017 |

Solvent Systems Comprising Two or Three Solvents:

The solubility of rofecoxib in solvent systems containing two or three solvents was determined. In solvent systems containing two solvents, 500 µg of each solvent was added to 100 mg of rofecoxib. In solvent systems containing three solvents, 333 µg of each solvent was added to 100 mg of rofecoxib. The samples were mixed using the protocol for solvent systems containing single solvents above. Serial dilutions of the rofecoxib solvent solutions were made (1:100 v:v), (1:1000 v/v), and (1:2000 v/v). Solvents without rofecoxib were diluted with methanol and used to blank a Beckman DU-7400 spectrophotometer. The absorbance of the samples was determined at a wavelength of 279.1 nm. The concentration of rofecoxib dissolved in the solvent was calculated using Beer's Law. The ability of the solvent systems to synergistically dissolve rofecoxib or antagonistically dissolve rofecoxib (reduce the ability of rofecoxib to dissolve was determined) according to the protocol below.

Determination of Synergistic or Antagonist Effect of Solvent Systems Containing Two or Three Solvents:

The contribution for solubility of a single solvent in a two-mixture solution was calculated to be ½ of the calculated solubility of rofecoxib in one gram of excipient. Likewise, the contribution for solubility of a three-mixture was calculated to be ⅓ of the calculated solubility of rofecoxib in one gram of excipient. The expected solubility for a mixture is the addition of the contribution of each excipient. For example, the solubility of rofecoxib in acetone is 23.58 mg/g, and the solubility of rofecoxib in benzyl alcohol is 19.54 mg/g. In a solvent system containing equal amounts of each solvent, the expected solubility of rofecoxib in 500 µg of acetone is 11.79 mg/g and the expected solubility of rofecoxib in 500 µg of benzyl alcohol is 9.77 mg/g. The expected solubility of rofecoxib in the solution containing equal parts benzyl alcohol and acetone is the sum of the expected solubilities of rofecoxib in 500 µg of benzyl alcohol and in 500 µg of acetone, or 21.56 mg/g. If the determined solubility of rofecoxib in a solution containing equal parts acetone and benzyl alcohol is greater than 21.56 mg/g rofecoxib, then the solvent system containing equal parts acetone and benzyl alcohol synergistically dissolves rofecoxib. If the determined solubility of rofecoxib in a solution containing equal parts acetone and benzyl alcohol is less than 21.56 mg/g rofecoxib, then the solvent system containing equal parts acetone and benzyl alcohol antagonistically dissolves rofecoxib. The percent change between the expected solubility and actual solubility was determined. A solvent system that has a percent change between the expected solubility and actual solubility of greater than 100% works synergistically to dissolve rofecoxib. A solvent system that has a percent change between the expected solubility and actual solubility of less than 100% works antagonistically to dissolve rofecoxib. Similar calculations are utilized for solvent systems containing three or more solvents.

Table 3 shows the solubility of rofecoxib in solvent systems containing two solvents. Table 4 shows the solubility of rofecoxib in solvent systems containing three solvents.

As shown by Table 3, solvent systems containing BA and AC, AC and PEG, EA and PPG, PEG and EA, AC and DGME, AC and PC, AC and DI, PC and DI, PEG and PGD, AC and PGD, DI and PGD, PC and PGD, EA and DMSO, PEG and PGD, PEG and EA, PEG and DGME, EA and DGME, EA and BA, DGME and PGD, AC and PGD, BA and PGD, and EA and M24D work synergistically to dissolve rofecoxib.

As shown by Table 4, the following solvent systems containing three solvents work synergistically to dissolve rofecoxib: AC, PEG, and PGD; BA, AC, and PEG; BA, PEG, and PGD; PC, AC, and PGD; BA, AC, and PGD; PC, PEG, and PGD; DI, PC, and AC; PC, BA, and AC; DI, PC, and BA; BA, AC, and PEG; PC, AC, and PGD; DI, PC, and EA; BA, AC, and PEG; PC, AC, and PEG; DI, PC, and DGME; DI, PC, and PEG; DI, PC, and PGD; PC, AC, and PGD; DI, BA, and PC; DI, PC, and DMSO; and AC, PEG, and PGD.

TABLE 3

Solubility of Rofecoxib in Solvent Systems containing two solvents

| Solvent 1 | Solvent 2 | Expected Solubility (mg/g) | Observed Solubility (mg/g) | % Change |
|---|---|---|---|---|
| BA | AC | 21.54 | 39.91 | 185.3 |
| AC | PEG | 18.34 | 31.96 | 174.3 |
| EA | PPG | 2.90 | 4.53 | 156.1 |
| BA | AC | 21.54 | 32.46 | 150.7 |
| PEG | EA | 9.32 | 14.00 | 150.3 |
| AC | DGME | 16.30 | 22.80 | 139.9 |
| AC | PEG | 18.34 | 25.15 | 137.2 |
| PC | AC | 36.48 | 49.69 | 136.2 |
| BA | AC | 21.54 | 29.03 | 134.8 |
| DI | AC | 31.34 | 42.18 | 134.6 |
| DI | PC | 44.29 | 59.30 | 133.9 |
| DI | PC | 44.29 | 57.83 | 130.6 |
| PEG | PGD | 10.04 | 12.50 | 124.5 |
| PC | AC | 36.48 | 45.26 | 124.1 |
| AC | PGD | 15.23 | 18.88 | 124.0 |
| DI | PGD | 23.04 | 28.54 | 123.9 |
| PC | PGD | 28.18 | 34.66 | 123.0 |
| EA | DMSO | 74.55 | 91.63 | 122.9 |
| PEG | PGD | 10.04 | 12.13 | 120.8 |
| EA | PEG | 9.32 | 11.19 | 120.0 |
| PEG | DGME | 11.11 | 13.30 | 119.7 |
| DGME | EA | 7.29 | 8.54 | 117.3 |
| BA | EA | 12.52 | 14.63 | 116.8 |
| DGME | PGD | 8.00 | 9.26 | 115.7 |
| AC | PGD | 15.23 | 17.32 | 113.7 |
| BA | PGD | 13.24 | 14.67 | 110.9 |
| EA | M24D | 3.05 | 3.36 | 110.4 |
| AC | EA | 14.52 | 15.92 | 109.7 |
| EA | PGD | 6.22 | 6.78 | 109.1 |
| EA | PS20 | 7.34 | 7.92 | 107.9 |
| EA | PS80 | 7.61 | 8.05 | 105.8 |
| DI | PEG | 26.14 | 27.65 | 105.8 |
| EA | PC | 27.47 | 28.53 | 103.9 |
| BA | PGD | 13.24 | 13.66 | 103.2 |

TABLE 3-continued

Solubility of Rofecoxib in Solvent Systems containing two solvents

| Solvent 1 | Solvent 2 | Expected Solubility (mg/g) | Observed Solubility (mg/g) | % Change |
|---|---|---|---|---|
| BA | AC | 31.65 | 31.86 | 100.7 |
| EA | PGD | 6.22 | 6.23 | 100.3 |
| PC | BA | 34.49 | 34.26 | 99.3 |
| AC | MP | 110.77 | 108.48 | 97.9 |
| PC | PGD | 28.18 | 27.55 | 97.8 |
| DI | DGME | 24.11 | 22.91 | 95.0 |
| EA | BA | 12.52 | 11.78 | 94.1 |
| EA | DS | 3.67 | 3.22 | 88.0 |
| EA | DIA | 3.77 | 3.23 | 85.7 |
| EA | AT | 2.91 | 2.40 | 82.6 |
| EA | AC | 14.52 | 11.49 | 79.1 |
| EA | MP | 101.75 | 76.59 | 75.3 |
| DI | BA | 29.34 | 21.20 | 72.3 |
| DI | MP | 118.57 | 84.92 | 71.6 |
| MP | EA | 107.75 | 76.89 | 71.4 |
| DI | EA | 22.32 | 15.60 | 69.9 |
| PC | MP | 123.72 | 85.76 | 69.3 |
| BA | DGME | 14.31 | 9.18 | 64.2 |
| BA | PEG | 16.34 | 10.33 | 63.2 |
| EA | DI | 22.32 | 13.84 | 62.0 |
| BA | PEG | 16.34 | 10.06 | 61.6 |
| BA | PEG | 16.34 | 9.91 | 60.6 |
| EA | DGME | 7.29 | 4.04 | 55.4 |
| AC | MP | 110.77 | 58.38 | 52.7 |
| EA | IPTD | 2.75 | 1.14 | 41.5 |
| BA | MP | 108.77 | 44.97 | 41.3 |
| EA | OA | 2.95 | 1.14 | 38.5 |
| BA | MP | 108.77 | 33.53 | 30.8 |
| PC | AC | 36.5 | 10.3 | 28.2 |

TABLE 4

Solubility of Rofecoxib in Solvent Systems containing three solvents

| Solvent 1 | Solvent 2 | Solvent 3 | Expected Solubility (mg/g) | Observed Solubility (mg/g) | % Change |
|---|---|---|---|---|---|
| AC | PEG | PGD | 14.55 | 55.95 | 384.56 |
| BA | AC | PEG | 18.75 | 50.86 | 271.20 |
| BA | PEG | PGD | 13.20 | 29.64 | 224.50 |
| PC | AC | PGD | 26.65 | 53.45 | 200.59 |
| BA | AC | PGD | 16.68 | 32.89 | 197.12 |
| DI | BA | PC | 36.04 | 55.93 | 155.19 |
| PC | PEG | PGD | 23.17 | 35.62 | 153.76 |
| DI | PC | AC | 37.38 | 53.73 | 143.72 |
| PC | BA | AC | 30.85 | 41.57 | 134.75 |
| DI | PC | BA | 36.04 | 47.68 | 132.30 |
| BA | AC | PEG | 18.75 | 24.55 | 130.90 |
| PC | AC | PGD | 26.65 | 34.56 | 129.71 |
| DI | PC | EA | 31.36 | 40.15 | 128.04 |
| BA | AC | PEG | 18.75 | 23.63 | 125.99 |
| PC | AC | PEG | 28.72 | 35.53 | 123.74 |
| DI | PC | DGME | 32.55 | 40.12 | 123.28 |
| DI | PC | PEG | 33.90 | 40.38 | 119.10 |
| DI | PC | PGD | 31.83 | 36.65 | 115.12 |
| PC | AC | PGD | 26.65 | 30.43 | 114.18 |
| DI | PC | DMSO | 77.39 | 88.47 | 114.83 |
| AC | PEG | PGD | 14.55 | 15.15 | 104.11 |
| PC | BA | DMSO | 70.86 | 60.68 | 85.64 |
| BA | MP | PGD | 74.82 | 63.91 | 85.42 |
| DI | BA | DMSO | 67.43 | 57.35 | 85.05 |
| PC | BA | PGD | 25.30 | 21.48 | 84.91 |
| BA | PEG | PGD | 13.20 | 11.19 | 84.77 |
| AC | MP | PGD | 76.17 | 58.79 | 77.19 |
| PC | BA | PEG | 27.37 | 17.37 | 63.48 |
| BA | AC | MP | 80.37 | 38.76 | 48.23 |
| PC | MP | PEG | 86.86 | 40.29 | 46.39 |
| BA | MP | PEG | 76.89 | 31.09 | 40.43 |

TABLE 4-continued

Solubility of Rofecoxib in Solvent Systems containing three solvents

| Solvent 1 | Solvent 2 | Solvent 3 | Expected Solubility (mg/g) | Observed Solubility (mg/g) | % Change |
|---|---|---|---|---|---|
| MP | PEG | PGD | 72.69 | 25.56 | 35.17 |
| AC | MP | PEG | 78.24 | 26.83 | 34.29 |
| PC | AC | MP | 90.34 | 30.88 | 34.18 |
| PC | MP | PGD | 84.79 | 18.40 | 21.70 |
| PC | BA | MP | 88.99 | 18.95 | 21.30 |

The solubility of rofecoxib compositions containing three or more ingredients was evaluated. The observations are found in Table 5.

TABLE 5

Solubility of Rofecoxib Compositions Containing Three or More Ingredients

| Formulation Name | Composition | Observations |
|---|---|---|
| Formulation 1 | AC (49% w/w), BA (49% w/w), Rofecoxib (2% w/w) | Rofecoxib is soluble |
| Formulation 2 | DI (49% w/w), PC (49% w/w), Rofecoxib (2% w/w) | Rofecoxib is soluble |
| Formulation 3 | DI (38.92% w/w), PC (12.275% w/w), DMSO (39% w/w), BA (8.0838% w/w), Rofecoxib (2% w/w) | Rofecoxib is soluble |
| Formulation 4 | DI (15% w/w), DMSO (15% w/w), PC (5% w/w), BA (2.7% w/w), Lanolin (10% w/w), PPG (50.3% w/w), Rofecoxib (2% w/w) | insoluble |
| Formulation 5 | DI (15% w/w), DMSO (15% w/w), PC (5% w/w), BA (2.7% w/w), Lanolin (10% w/w), PEG-400 (50.5% w/w), Rofecoxib (2% w/w) | insoluble |
| Formulation 6 | DI (15% w/w), DMSO (15% w/w), PC (5% w/w), BA (2.7% w/w), Lanolin (10% w/w), Mineral Oil (50.5% w/w), Rofecoxib (2% w/w) | Seems to separate if it is not stirred. |
| Formulation 7 | DI (15% w/w), DMSO (15% w/w), PC (5% w/w), BA (2.7% w/w), Petroleum (10% w/w), Mineral Oil (50.5% w/w), Rofecoxib (2% w/w) | Separates into two phases |
| Formulation 8 | DI (15% w/w), DMSO (15% w/w), PC (5% w/w), BA (2.7% w/w), Lanolin (10% w/w), Mineral Oil (40.5% w/w), PBS/Xanthan Gum 0.75% (10% w/w), Rofecoxib (2% w/w) | The Xanthan gum does not mix at all. |
| Formulation 9 | DI (32.8% w/w), PC (10.9% w/w), BA (5.9% w/w), DMSO (34.8% w/w), AT (10.9% w/w), Rofecoxib (4.3% w/w) | Insoluble |
| Formulation 10 | DI (28.4% w/w), PC (9.4% w/w), BA (5.1% w/w), AT (9.4% w/w), OA (9.4% w/w), DMSO (34.2% w/w), Rofecoxib (3.7% w/w) | Insoluble |
| Formulation 11 | DI (32.8% w/w), PC (10.9% w/w), BA (5.9% w/w), DGME (10.9% w/w), DMSO (34.8% w/w), Rofecoxib (4.3% w/w) | Insoluble |
| Formulation 12 | DI (28.4% w/w), PC (9.4% w/w), BA (5.1% w/w), DGME (9.4% w/w), DMSO (34.2% w/w), OA (9.4% w/w), Rofecoxib (3.7% w/w) | Insoluble |
| Formulation 13 | DI (29.6% w/w), PC (9.8% w/w), BA (5.3% w/w), DGME (9.8% w/w), DMSO (31.4% w/w), AT (9.8% w/w), Rofecoxib (3.9% w/w) | Insoluble |
| Formulation 14 | DI (23.8% w/w), PC (7.9% w/w), BA (4.2% w/w), DGME (7.9% w/w), DMSO (28.8% w/w), AT (7.9% w/w), OA (7.9% w/w), DGME (7.9% w/w), Rofecoxib (3.1% w/w) | Insoluble |
| Formulation 15 | DI (9.5% w/w), PC (3.1% w/w), BA (1.7% w/w), DMSO (72.6% w/w), Rofecoxib (12.7% w/w) | soluble |
| Formulation 16 | DI (32.8% w/w), PC (10.9% w/w), BA (5.9% w/w), DMSO (34.8% w/w), OA (10.9% w/w), Rofecoxib (4.3% w/w) | Insoluble |
| Formulation 17 | DI (34.3% w/w), PC (11.4% w/w), BA (6.1% w/w), DMSO (31.9% w/w), PS-20 (11.4% w/w), Rofecoxib (4.5% w/w) | Soluble |
| Formulation 18 | DI (32.8% w/w), PC (10.9% w/w), BA (5.9% w/w), DMSO (34.8% w/w), PS20 (10.9% w/w), Rofecoxib (4.3% w/w) | Soluble |
| Formulation 19 | DI (27.1% w/w), PC (9% w/w), BA (4.8% w/w), OA (9% w/w), PS20 (9% w/w), DMSO (37% w/w), Rofecoxib (3.6% w/w) | Soluble after sonication |
| Formulation 20 | DI (24.9% w/w), PC (8.3% w/w), BA (4.4% w/w), AT (8.3% w/w), OA (8.3% w/w), PS20 (8.3% w/w), DMSO (33.9% w/w), Rofecoxib (3.3% w/w) | insoluble before sonication; after sonication-soluble |
| Formulation 21 | DI (24.9% w/w), PC (8.3% w/w), BA (4.4% w/w), DGME (8.3% w/w), OA (8.3% w/w), PS20 (8.3% w/w), DMSO (33.9% w/w), Rofecoxib (3.3% w/w) | insoluble before sonication; after sonication-soluble |
| Formulation 22 | DI (23% w/w), PC (7.6% w/w), BA (4.1% w/w), DGME (7.6% w/w), AT (7.6% w/w), OA (7.6% w/w), PS20 (7.6% w/w), DMSO (31.3% w/w), Rofecoxib (3% w/w) | insoluble before sonication; after sonication-soluble |
| Formulation 23 | DI (29.6% w/w), PC (9.8% w/w), BA (5.3% w/w), DMSO (31.4% w/w), PS80 (9.8% w/w), OA (9.8% w/w), Rofecoxib (3.9% w/w) | slightly insoluble before sonication; after sonication-soluble |
| Formulation 24 | DI (60.7% w/w), PC (20.2% w/w), BA (10.9% w/w), Rofecoxib (8% w/w) | slightly insoluble before sonication; after sonication-soluble |
| Formulation 25 | DI (32.8% w/w), PC (10.9% w/w), BA (5.9% w/w), DMSO (34.8% w/w), PS60 (10.9% w/w), Rofecoxib (4.3% w/w) | slightly insoluble before sonication; after sonication-soluble |
| Formulation 26 | DI (32.8% w/w), PC (10.9% w/w), BA (5.9% w/w), DMSO (34.8% w/w), PS60 | slightly insoluble before sonication; after sonication- |

TABLE 5-continued

Solubility of Rofecoxib Compositions Containing Three or More Ingredients

| Formulation Name | Composition | Observations |
|---|---|---|
| | (10.9% w/w), OA (10.9% w/w), Rofecoxib (4.3% w/w) | soluble |
| Formulation 27 | DI (50.5% w/w), PC (16.8% w/w), BA (9% w/w), OA (16.8% w/w), Rofecoxib (6.7% w/w) | insoluble |
| Formulation 28 | DI (38.7% w/w), PC (12.9% w/w), BA (6.9% w/w), OA (12.9% w/w), DMSO (23.3% w/w), Rofecoxib (5.1% w/w) | After sonication it is soluble and stable |
| Formulation 29 | DI (14% w/w), PC (4.6% w/w), BA (2.5% w/w), OA (4.6% w/w), DMSO (8.4% w/w), Glycerol monostearate (4.6% w/w), Mineral Oil (1.8% w/w), Rofecoxib (59% w/w) | after sitting overnight, separates |
| Formulation 30 | DI (14.8% w/w), PC (4.9% w/w), BA (2.6% w/w), OA (4.9% w/w), DMSO (8.9% w/w), Bees wax (3.4% w/w), Lanoline (9.9% w/w), Mineral Oil (48.1% w/w), Rofecoxib (1.9% w/w) | Thick emollient that does not separate |
| Formulation 31 | DI (30.7% w/w), PC (10.2% w/w), BA (5.5% w/w), OA (10.2% w/w), DMSO (18.5% w/w), Lanoline (20.5% w/w), Rofecoxib (4.1% w/w) | Ointment that does not separate |
| Formulation 32 | DI (14.6% w/w), PC (4.8% w/w), BA (2.6% w/w), OA (7.3% w/w), DMSO (8.8% w/w), Lanoline (9.7% w/w), Olive Oil (49.9% w/w), Rofecoxib (1.9% w/w) | Separates even after addition of 20% SDS |
| Formulation 33 | DI (14.5% w/w), PC (4.8% w/w), BA (2.6% w/w), OA (7.2% w/w), DMSO (8.7% w/w), Lanoline (4.8% w/w), Olive Oil (55% w/w), Rofecoxib (1.9% w/w) | separates even after addition of 50 µL PS80 |
| Formulation 34 | DI (15.3% w/w), PC (5.1% w/w), BA (2.7% w/w), OA (7.6% w/w), DMSO (9.2% w/w), PEG-400 (57.7% w/w), Rofecoxib (2% w/w) | This combination works well |
| Formulation 35 | DI (15% w/w), PC (5% w/w), DMSO (9.1% w/w), BA (2.6% w/w), Oleic Acid (5% w/w), Lanolin (10% w/w), Min. Oil (51.3% w/w), Rofecoxib (2% w/w) | lanoline causes separation |
| Formulation 36 | DI (15% w/w), PC (5% w/w), DMSO (9.1% w/w), BA (2.6% w/w), Oleic Acid (5% w/w), Lanolin (10% w/w), Min. Oil (47.8% w/w), Bees Wax (3.5% w/w), Rofecoxib (2% w/w) | Bees wax stablizes the ointment |
| Formulation 37 | DI (15% w/w), PC (5% w/w), BA (2.6% w/w), DMSO (9.1% w/w), Oleic Acid (5% w/w), Lanolin (5% w/w), Min. Oil (47.8% w/w), Bees Wax (3.5% w/w), Rofecoxib (2% w/w) | Slight separation of oil at the top |
| Formulation 38 | Rofecoxib (2% w/w), DI (15% w/w), PC (5% w/w), BA (2.6% w/w), DMSO (9.1% w/w), Oleic Acid (5% w/w), Lanolin (10% w/w), Min. Oil (45.45% w/w), Bees Wax (1.75% w/w) | mineral oil causes solvent system to separate and lanolin causes precipitation of rofecoxib |
| Formulation 39 | Rofecoxib (2% w/w), DI (15% w/w), PC (5% w/w), BA (2.6% w/w), DMSO (9.1% w/w), Oleic Acid (5% w/w), Lanolin (5% w/w), Min. Oil (47.8% w/w), Bees Wax (1.75% w/w) | lanolin causes solvent system to separate |
| Formulation 40 | DI (15% w/w), PC (5% w/w), BA (2% w/w), DMSO (10% w/w), OA (5% w/w), PEG-400 (51% w/w), Lanoline (10% w/w), Rofecoxib (2% w/w) | lanolin causes solvent system to separate |
| Formulation 41 | DI (15% w/w), PC (5% w/w), BA (2% w/w), DMSO (10% w/w), OA (5% w/w), PEG-400 (61% w/w), Rofecoxib (2% w/w) | Soluble |
| Formulation 42 | DI (15% w/w), PC (5% w/w), BA (2% w/w), DMSO (10% w/w), OA (5% w/w), PEG-400 (40% w/w), IMTD/IM (20.995% w/w), Rofecoxib (2% w/w) | Separates |
| Formulation 43 | DI (15% w/w), PC (5% w/w), BA (2% w/w), DMSO (10% w/w), OA (5% w/w), PEG-400 (40% w/w), IMTD/IM (19% w/w), SDS (2% w/w), Rofecoxib (2% w/w) | Separates |
| Formulation 44 | DI (15% w/w), PC (5% w/w), BA (2% w/w), DMSO (10% w/w), OA (5% w/w), PEG-400 (40% w/w), PGD (21% w/w), Rofecoxib (2% w/w) | precipitation after three days |
| Formulation 45 | DI (15% w/w), PC (5% w/w), BA (2% w/w), DMSO (10% w/w), OA (5% w/w), PEG-400 (40% w/w), PGD (12% w/w), Lanoline (9.5% w/w), Rofecoxib (2% w/w) | Sonicated until warm but then it clumps when it cools |
| Formulation 46 | DI (15% w/w), PC (5% w/w), BA (2% w/w), DMSO (10% w/w), OA (5% w/w), PEG-400 (46% w/w), PS80 (15% w/w), Rofecoxib (2% w/w) | precipitation after three days |
| Formulation 47 | DI (15% w/w), PC (5% w/w), BA (2% w/w), DMSO (10% w/w), OA (5% w/w), PEG-400 (40% w/w), PPG (21% w/w), Rofecoxib (2% w/w) | Precipitates |
| Formulation 48 | DI (15% w/w), PC (5% w/w), BA (2% w/w), DMSO (10% w/w), OA (5% w/w), PEG-400 (46% w/w), PS20 (15% w/w), Rofecoxib (2% w/w) | precipitation after three days |
| Formulation 49 | DI (15% w/w), PC (5% w/w), BA (2% w/w), DMSO (10% w/w), OA (5% w/w PEG-400 (42% w/w), Bees Wax (3.1% w/w), PS80 (15% w/w), Rofecoxib (2% w/w) | insoluble but may be soluble with more homogenization |
| Formulation 50 | DI (15% w/w), PC (5% w/w), BA (2% w/w), DMSO (10% w/w), OA (5% w/w) PEG-400 (40% w/w), EA (21% w/w), Rofecoxib (2% w/w) | Soluble after 7 days at RT |

TABLE 5-continued

Solubility of Rofecoxib Compositions Containing Three or More Ingredients

| Formulation Name | Composition | Observations |
|---|---|---|
| Formulation 51 | DI (15% w/w), PC (5% w/w), BA (2% w/w), DMSO (10% w/w), OA (5% w/w), PEG-400 (40% w/w), DGME (21% w/w), Rofecoxib (2% w/w) | precipitation after three days |
| Formulation 52 | DI (15% w/w), PC (5% w/w), BA (2% w/w), DMSO (10% w/w), OA (5% w/w), PEG-400 (50% w/w), Alfa-Terpinol (11% w/w), Rofecoxib (2% w/w) | precipitation after three days |
| Formulation 53 | DI (15% w/w), PC (5% w/w), BA (2% w/w), DMSO (10% w/w), OA (5% w/w), PEG-400 (49% w/w), DIA (12% w/w), Rofecoxib (2% w/w) | Soluble after 7 days at RT |
| Formulation 54 | DI (15% w/w), PC (5% w/w), BA (2% w/w), DMSO (10% w/w), OA (5% w/w), PEG-400 (40% w/w), DS (21% w/w), Rofecoxib (2% w/w) | precipitation after three days |
| Formulation 55 | DI (15% w/w), PC (5% w/w), BA (2% w/w), DMSO (10% w/w), OA (5% w/w), PEG-400 (49% w/w), M24D (12% w/w), Rofecoxib (2% w/w) | precipitation after three days |
| Formulation 56 | DI (15% w/w), PC (5% w/w), BA (2% w/w), DMSO (10% w/w), OA (5% w/w), PEG-400 (40% w/w), Mineral Oil (21% w/w), Rofecoxib (2% w/w) | precipitation after three days |
| Formulation 57 | DI (15% w/w), PC (5% w/w), BA (2% w/w), DMSO (10% w/w), OA (5% w/w), DIA (10% w/w), PEG-400 (52% w/w), Rofecoxib (1% w/w) | Soluble |
| Formulation 58 | DI (15% w/w), PC (5% w/w), BA (2% w/w), DMSO (10% w/w), OA (5% w/w), DIA (10% w/w), PEG-400 (51% w/w), Rofecoxib (2% w/w) | Soluble |
| Formulation 59 | DI (15% w/w), PC (5% w/w), BA (2% w/w), DMSO (15% w/w), OA (5% w/w), DIA (10% w/w), PEG-400 (47% w/w), Rofecoxib (1% w/w), | Soluble |
| Formulation 60 | DI (15% w/w), PC (5% w/w), BA (2% w/w), DMSO (15% w/w), EA (20% w/w), DIA (20% w/w), AT (10% w/w), OA (5% w/w), Rofecoxib (4% w/w) | OA causes precipitation of rofecoxib |
| Formulation 61 | DI (17.4% w/w), PC (5.8% w/w), BA (2.3% w/w), DMSO (17.4% w/w), EA (23.2% w/w), DIA (23.2% w/w), OA (5.8% w/w), Rofecoxib (4.6% w/w) | OA causes precipitation of rofecoxib |
| Formulation 62 | DI (15% w/w), PC (5% w/w), BA (2.3% w/w), DMSO (15% w/w), EA (30% w/w), Rofecoxib (4% w/w), DIA (12% w/w), AT (10% w/w), Bees Wax (3% w/w), Menthol (2.5% w/w), Eucalyptus (1.2% w/w) | AT causes precipitation of rofecoxib |
| Formulation 63 | DI (15% w/w), PC (5% w/w), BA (2.3% w/w), DMSO (15% w/w), EA (30% w/w), DIA (12% w/w), Rofecoxib (4% w/w), PS20 (15% w/w), Menthol (2.5% w/w), | Rofecoxib precipitates after 24 hours |
| Formulation 64 | DI (15.4% w/w), PC (5.1% w/w), BA (2.5% w/w), DMSO (20.6% w/w), DIA (12.3% w/w), PS20 (15.4% w/w), DGME (25.2% w/w), Rofecoxib (3% w/w) | Precipitates |
| Formulation 65 | DI (15.9% w/w), PC (5.3% w/w), BA (2.6% w/w), DMSO (21.2% w/w), DIA (12.7% w/w), PS20 (15.9% w/w), DGME (17.5% w/w), OA (5.3% w/w), Rofecoxib (3.1% w/w) | Rofecoxib is soluble |
| Formulation 66 | DI (11.3% w/w), PC (5.4% w/w), BA (2.7% w/w), DMSO (21.6% w/w), DIA (12.9% w/w), PS20 (16.2% w/w), PGD (10.8% w/w), OA (5.4% w/w), DGME (10.2% w/w), Rofecoxib (3.2% w/w) | Precipitates |
| Formulation 67 | DI (15.4% w/w), PC (5.1% w/w), BA (2.5% w/w), DMSO (20.6% w/w), DIA (12.3% w/w), PS20 (15.4% w/w), AT (10.3% w/w), DGME (14.8% w/w), Rofecoxib (3% w/w) | Slight precipitation |
| Formulation 68 | DI (15.4% w/w), PC (5.1% w/w), BA (2.5% w/w), DMSO (20.6% w/w), DIA (12.3% w/w), PS20 (15.4% w/w), AT (10.3% w/w), OA (5.1% w/w), DGME (9.7% w/w), Rofecoxib (3% w/w) | Precipitates |
| Formulation 69 | DI (15.4% w/w), PC (5.1% w/w), BA (2.5% w/w), DMSO (20.6% w/w), DIA (12.3% w/w), PS20 (15.4% w/w), PG (25.2% w/w), Rofecoxib (3% w/w) | Precipitates |
| Formulation 70 | DI (15.4% w/w), PC (5.1% w/w), BA (2.5% w/w), DMSO (20.6% w/w), DIA (12.3% w/w), PS20 (15.4% w/w), OA (5.1% w/w), PPG (20.1% w/w), Rofecoxib (3% w/w) | Precipitates |
| Formulation 71 | DI (15.3% w/w), PC (5.1% w/w), BA (2.5% w/w), DMSO (20.4% w/w), DIA (12.2% w/w), PS20 (15.3% w/w), PGD (10.2% w/w), DGME (14.7% w/w), Rofecoxib (4% w/w) | Precipitates |
| Formulation 72 | DI (15.7% w/w), PC (5.2% w/w), BA (2.6% w/w), DMSO (20.9% w/w), DIA (12.5% w/w), PS20 (15.7% w/w), PGD (10.4% w/w), AT (12.5% w/w), Rofecoxib (4.1% w/w) | Precipitates |
| Formulation 73 | DI (15.8% w/w), PC (5.2% w/w), BA (2.6% w/w), DMSO (21.1% w/w), DIA (12.6% w/w), PS20 (15.8% w/w), PGD (10.5% w/w), | Precipitates |

TABLE 5-continued

Solubility of Rofecoxib Compositions Containing Three or More Ingredients

| Formulation Name | Composition | Observations |
|---|---|---|
| | AT (12.6% w/w), Rofecoxib (3.1% w/w) | |
| Formulation 74 | DI (15.7% w/w), PC (5.2% w/w), BA (2.6% w/w), DMSO (21% w/w), DIA (12.6% w/w), PS20 (15.7% w/w), PGD (10.5% w/w), AT (5.2% w/w), DGME (7.8% w/w), Rofecoxib (3.1% w/w) | Soluble |
| Formulation 75 | DI (15.7% w/w), PC (5.2% w/w), BA (2.6% w/w), DMSO (21% w/w), DIA (12.6% w/w), PS20 (15.7% w/w), PGD (10.5% w/w), AT (7.8% w/w), DGME (5.2% w/w), Rofecoxib (3.1% w/w) | Soluble |
| Formulation 76 | DI (15.6% w/w), PC (5.2% w/w), BA (2.6% w/w), DMSO (20.8% w/w), DIA (12.5% w/w), PS20 (15.6% w/w), AT (10.4% w/w), DGME (15% w/w), Rofecoxib (2% w/w) | some precipitation |
| Formulation 77 | DI (14.1% w/w), PC (4.7% w/w), BA (2.3% w/w), DMSO (18.8% w/w), DIA (11.3% w/w), PS20 (14.1% w/w), PGD (9.4% w/w), OA (4.7% w/w), DGME (8.9% w/w), Rofecoxib (1.8% w/w), Lanoline (9.4% w/w) | Works ok but separates a little |
| Formulation 80 | DI (15.62% w/w); PC (5.2% w/w); BA (2.6% w/w); DMSO (20.83% w/w); OA (5.2% w/w); DIA (12.5% w/w); PS20 (15.62% w/w); DGME (8.85% w/w); PGD (10.41% w/w); Rofecoxib (2.08% w/w); Spearmint (0.34% w/w); Eucalyptus oil (0.69% w/w) | Soluble |
| Formulation 82 | DI (15.62% w/w); PC (5.2% w/w); BA (2.6% w/w); DMSO (20.83% w/w); OA (5.2% w/w); DIA (12.5% w/w); PS20 (15.62% w/w); DGME (19.27% w/w); Rofecoxib (2.08% w/w); Spearmint (0.34% w/w); Eucalyptus oil (0.69% w/w) | Soluble |
| Formulation 83 | DI (15.62% w/w); PC (5.2% w/w); BA (2.6% w/w); DMSO (20.83% w/w); DIA (12.5% w/w); PS20 (15.62% w/w); DGME (8.85% w/w); PGD (10.41% w/w); AT (5.2% w/w); Rofecoxib (2.08% w/w); Spearmint (0.34% w/w); Eucalyptus oil (0.69% w/w) | Soluble |
| Formulation 85 | DI (15% w/w); PC (5% w/w); BA (2.5% w/w); DMSO (20% w/w); DIA (12% w/w); DGME (18.5% w/w); PS20 (15% w/w); OA (5% w/w); Hydoxypropyl cellulose 100,000 (4% w/w); Rofecoxib 2% (2% w/w); Eucalyptus Oil (0.33% w/w); Spearmint Oil (0.67% w/w) | Soluble |
| Formulation 86 | DI (15.62% w/w); PC (5.2% w/w); BA (2.6% w/w); DMSO (10.41% w/w); OA (7.81% w/w); PEG-400 (55.2% w/w); Rofecoxib (2.08% w/w); Spearmint (0.34% w/w); Eucalyptus oil (0.69% w/w) | light precipitation overnight |
| Formulation 87 | DI (15.62% w/w); PC (5.2% w/w); BA (2.6% w/w); DMSO (10.41% w/w); OA (5.2% w/w); PEG-400 (35.94% w/w); EA (21.87% w/w); Rofecoxib (2.08% w/w); Spearmint (0.34% w/w); Eucalyptus oil (0.68% w/w) | light precipitation overnight |
| Formulation 88 | DI (15.54% w/w); PC (5.18% w/w); BA (2.59% w/w); DMSO (10.36% w/w); OA (7.77% w/w); PEG-400 (43% w/w); DIA (12.43% w/w); Rofecoxib (2.07% w/w); Spearmint (0.34% w/w); Eucalyptus oil (0.69% w/w) | precipitation after three days |
| Formulation 89 | DI (15.62% w/w); PC (5.2% w/w); BA (2.08% w/w); DMSO (10.41% w/w); OA (5.2% w/w); PEG-400 (47.91% w/w); DIA (10.41% w/w); Rofecoxib (2.08% w/w); Spearmint (0.34% w/w); Eucalyptus oil (0.69% w/w) | precipitation after three days |
| Formulation 90 | DI (15.62% w/w); PC (5.2% w/w); BA (2.6% w/w); DMSO (20.83% w/w); OA (5.2% w/w); DIA (12.5% w/w); PS20 (15.62% w/w); DGME (18.22% w/w); Rofecoxib (3.12% w/w); Spearmint (0.34% w/w); Eucalyptus oil (0.69% w/w) | heavy precipitation overnight |
| Formulation 91 | DI (15.62% w/w); PC (5.2 % w/w); BA (2.6% w/w); DMSO (20.83% w/w); DIA (12.5% w/w); PS20 (15.62 % w/w); DGME (7.81% w/w); PGD (10.41% w/w); AT (5.2% w/w); Rofecoxib (3.12% w/w); Spearmint (0.34% w/w); Eucalyptus oil (0.69% w/w) | light precipitation overnight |
| Formulation 92 | DI (15.62% w/w); PC (5.2% w/w); BA (2.6% w/w); DMSO (20.83% w/w); DIA (12.5% w/w); PS20 (15.62% w/w); DGME (5.2% w/w); PGD (10.41% w/w); AT (7.81% w/w); Rofecoxib (3.12% w/w); Spearmint (0.34% w/w); Eucalyptus oil (0.69% w/w) | heavy precipitation overnight |
| Formulation 93 | DI (15.62% w/w); PC (5.2% w/w); BA (2.6% w/w); DMSO (10.41% w/w); OA (5.2% w/w); PEG-400 (45.31% w/w); DIA (12.5% w/w); Rofecoxib (2.08% w/w); Spearmint (0.34% w/w); Eucalyptus oil (0.69% w/w) | precipitation after three days |

Example 2. Release of Rofecoxib from Topical Solution

A Franz cell apparatus was used to test for release of rofecoxib from the disclosed rofecoxib topical formulations. The Franz cell apparatus has six cells, which exhibit different volumes, diameters, and areas (Table 6). The area of cells 1-5 is 8.73 cm$^2$. Membranes used for diffusion release were Durapure PDVF (0.45 μm, Millipore). The receptor media is 70% PBS (pH 7.4) from Gibco, 15% dimethyl isosorbide and 15% propylene carbonate. A circulating water bath was set to maintain the receptor media at 32 degrees Celsius. The cells were pre-warmed for 30 minutes before the samples were added to the donor chamber.

TABLE 6

Franz Cell Parameters

| Cell | Volume (mL) | Diameter (mm) | Area (cm$^2$) |
|---|---|---|---|
| 1 | 11.0 | 4.0/14.0 | 1.54 |
| 2 | 10.9 | 14.5/14.5 | 1.7 |
| 3 | 11.2 | 16.5/16.5 | 2.1 |
| 4 | 11.15 | 15.0/15.0 | 1.8 |
| 5 | 10.8 | 14.5/14.75 | 1.7 |
| 6 | 11.15 | 15.0/16.0 | 1.7617 |

The first 5 cells were loaded with either a fixed volume of a topical sample equal to 300 μl (6 mg) or was loaded with 1 ml sample with 20 mg of rofecoxib. The 6th cell was used as a negative control for rofecoxib diffusion e.g. the sixth cell was loaded with the same volume of the of the excipients without rofecoxib.

300 μL samples were taken at 10, 20, 30, 40, 50, 60, 75, 90, 105, 120 and 180 minutes. The receptor volume was replaced with fresh prewarmed receptor fluid directly after the sample was taken. The samples and control were diluted 1:10 (100 ul:900 ul) into methanol. After using the control to blank the spectrophotometer (as in Example 1), the absorbance of the samples was determined at 279.1 nm.

Calculation of Rofecoxib after 90 Minutes of Diffusion:

To calculate the amount of rofecoxib that diffused in 90 minutes per cell, the OD reading was multiplied by the extinction coefficient of rofecoxib (29.06) times the dilution (10×) times the volume of the cell (11 ml) and divided by 1000 to determine the milligrams of rofecoxib that diffused in 90 minutes. For example, for cell #1, which has an absorbance at 279.1 nm of 1.5033, the amount of rofecoxib that diffused=((1.5033)(29.06)(10)(11))/1000=4.805 mg. The total amount of rofecoxib that diffused was determined by adding the amount of rofecoxib that diffused through each cell. The average amount of rofecoxib that diffused in 90 minutes was determined by dividing the total amount of rofecoxib that diffused by the number of cells. #1 (279.1 nm) O.D.=1.5033*29.06*10*11/1000=4.805 mg.

Calculating the Diffusion Per Cm$^2$:

The diffusion per square area in 90 minutes was calculated by dividing the total amount of rofecoxib that migrated through cells 1 to 5 and dividing by the total membrane area (Take the total of all rofecoxib through the five membranes in 90 minutes and divide by the area of the total membrane area of cells 1-5 (8.73 cm$^2$). For example, if 22.95 mg of rofecoxib diffused, and the membrane area of the cells is 8.73 cm$^2$, the amount of rofecoxib that diffused per square centimeter is 2.626 mg/cm$^2$.

Calculating the Flux Rate:

The flux rate or the amount of rofecoxib that diffused per cm$^2$ per hour (μg/cm$^2$/hour) was determined. Two points within the linear range of a graph of time versus amount of rofecoxib were utilized, the first point after which diffusion became linear, or T=1 and a second point 30 minutes later, or T=2. The diffusion rate is the total mg of rofecoxib diffused at T=2 (i.e. 60 minutes) minus mg of total rofecoxib diffused at T=1 (30 minutes) times 2 (to make it and total mg per hour) divided by the total cm$^2$. In the example above example, at 30 minutes the diffused rofecoxib=9.062 mg and at 60 minutes=19.731 mg; (19.731 mg-9.062 mg)×2=21.338 mg/hour divided by 8.7389 cm$^2$=2.44 mg/hr/cm$^2$.

Flux of Various Rofecoxib Topical Compositions:

Franz cells were employed to evaluate the flux of various rofecoxib topical compositions. Initial experiments used the following receptor media: 90% PBS pH 87.4 and 10% MP; 90% PBS 7.4 with 10% methanol. These receptor medias caused rofecoxib to precipitate out of solution. The experiments described below used Franz cell media of 70% PBS pH 7.4 with 15% DI and 15% PC as receptor media, enabling rofecoxib to stay in solution. The below experiments evaluated the diffusion of the rofecoxib topical compositions through 0.45 μm Durapore® polyvinylidene fluoride (PVDF) membranes (obtained from EMD Millipore).

A composition (Formulation 1) containing acetone (49% w/w), benzyl alcohol (49% w/w), and rofecoxib (2% w/w) resulted in a flux rate of 1.52 mg/h/cm$^2$. This composition allowed 93% of rofecoxib to diffuse within 90 minutes.

A composition (Formulation 2) containing DI (49% w/w), PC (49% w/w), and rofecoxib (2% w/w) resulted in a flux rate of 1.39 mg/h/cm$^2$. This composition allowed 82% of rofecoxib to diffuse within 90 minutes.

A composition (Formulation 3) containing 39% w/w DI, 12% w/w PC, 39% w/w DMSO, 8% w/w BA, and 2% w/w rofecoxib resulted in a flux rate of 15.31 mg/h/cm$^2$. This composition allowed 76.51% of rofecoxib to diffuse within 90 minutes.

A composition (Formulation 6) containing 15% w/w DI, 5 w/w PC, 15 w/w DMSO, 2.7% w/w BA, 10% w/w lanoline, 50.3% mineral oil, and 2.0% w/w rofecoxib resulted in a flux rate of 0.359 mg/h/cm$^2$. This composition allowed 18.8% of rofecoxib to diffuse within 90 minutes. Without being bound by theory, the lower percent of rofecoxib diffusion and flux rate may be attributed to the fact that the organic solvents moved through the membrane faster than rofecoxib, leading to crystallization of rofecoxib, and an ending of rofecoxib diffusion. This experiment highlighted the challenges of developing a rofecoxib topical composition.

A composition (Formulation 35) containing 15% w/w DI, 5 w/w PC, 9% w/w DMSO, 3% w/w BA, 5% w/w oleic acid, 10% w/w lanolin, 51% w/w mineral oil, and 2.0% w/w rofecoxib resulted in a flux rate of 0.919 mg/h/cm$^2$. This composition allowed 48.7% of rofecoxib to diffuse within 90 minutes.

A composition (Formulation 36) containing 15% w/w DI, 5 w/w PC, 9% w/w DMSO, 3% w/w BA, 5% w/w oleic acid, 10% w/w lanolin, 48% w/w mineral oil, 4% w/w bees wax, and 2.0% w/w rofecoxib resulted in a flux rate of 0.099 mg/h/cm$^2$. This composition allowed 12.85% of rofecoxib to diffuse within 90 minutes.

A composition (Formulation 41) containing 15% w/w DI, 5% w/w PC, 10% w/w DMSO, 5% w/w oleic acid, 2% w/w BA, 61% w/w PEG, and 2.0% w/w rofecoxib resulted in a flux rate of 0.229 mg/h/cm$^2$. This composition allowed 36.22% of rofecoxib to diffuse within 90 minutes.

Figure 3:
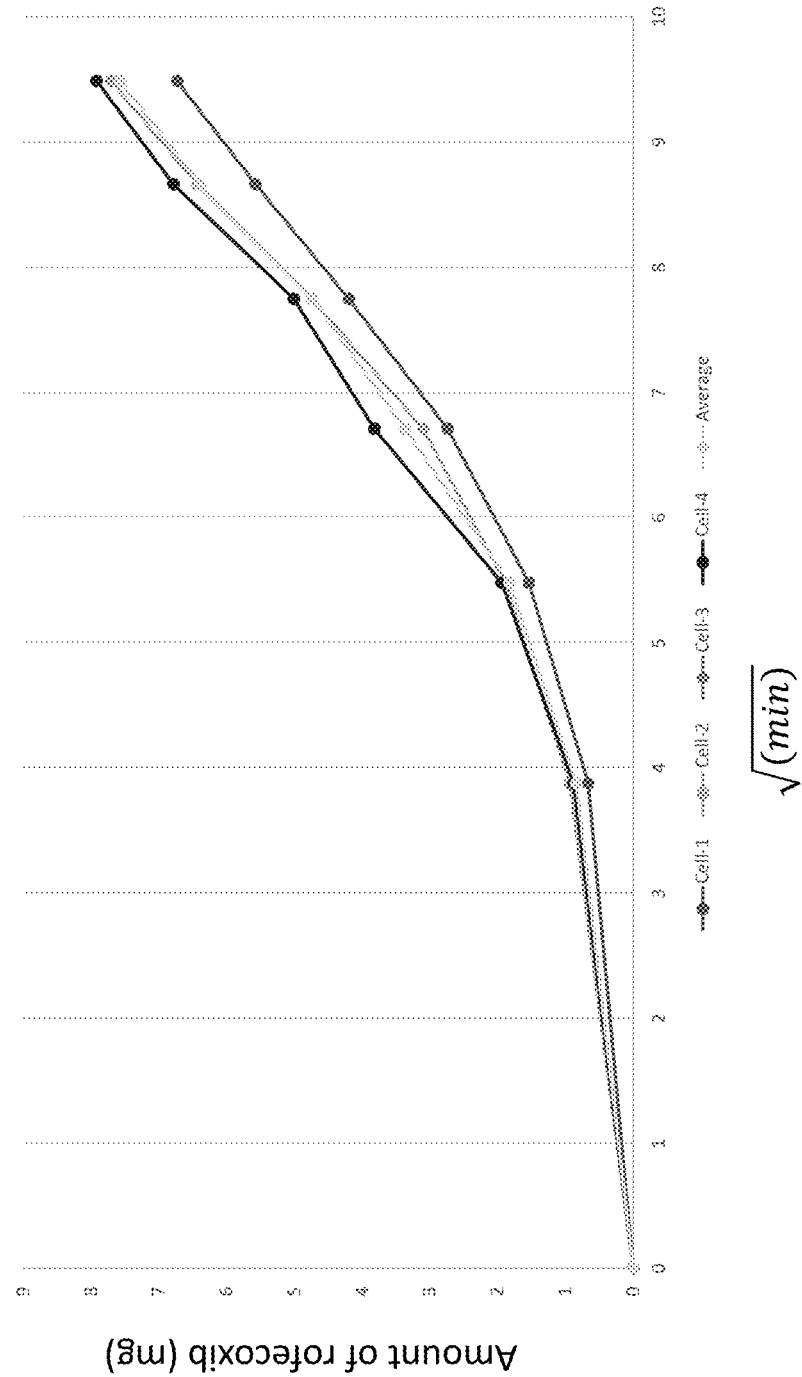
FIG. 3 shows the diffusion of Formulation 57 through a Franz cell.

A composition (Formulation 57) containing 15% w/w DI, 5% w/w PC, 10% w/w DMSO, 5% w/w oleic acid, 2% w/w BA, 10% DIA, 52% w/w PEG, and 1.0% w/w rofecoxib resulted in a flux rate of 2.19 mg/h/cm$^2$. This composition allowed 75.71% of rofecoxib to diffuse within 90 minutes (FIG. 3). In comparison, Voltaren® Gel which comprises diclofenac has a flux rate of 0.604 mg/cm$^2$/hour and 24.4% of diclofenac diffused in 90 minutes.

A composition (Formulation 58) containing 15% w/w DI, 5% w/w PC, 10% w/w DMSO, 2% w/w BA, 5% w/w oleic acid, 10% w/w DIA, 51% w/w PEG, and 2.0% w/w rofecoxib resulted in a flux rate of 4.4 mg/h/cm$^2$. This composition allowed 13.26% of rofecoxib to diffuse within 90 minutes.

Future experiments will test the ability of the compositions to diffuse through pig skin and human skin. Animal studies using conventional pain models, including but not limited to, the formalin model, tail-flick model, hot plate model, complete Freund's Adjuvant (CFA) model, nerve growth factor (NGF) model, Carrageenan Paw Edema (CPE) model, and monoiodoacetate (MIA)-induced osteoarthritis joint pain model. Rofecoxib topical compositions will be evaluated in humans that exhibit one or more of the following of arthritis, osteoarthritis, juvenile rheumatoid arthritis, joint pain due to injury e.g. ankle sprains, sports injuries, carpal tunnel syndrome, ankle sprains, rheumatoid arthritis, inflammation, low back pain, ankylosing spondylitis, psoriatic arthritis, tennis elbow, headache, and migraine. Rofecoxib topical compositions will be also be evaluated in pre-clinical studies as mandated by the Food and Drug Administration for topical formulations.

Example 3. Release of Rofecoxib in Human Skin

The ability of rofecoxib topical compositions to penetrate human skin was evaluated using a Franz diffusion cell. Retention of rofecoxib in the epidermal and dermal skin compartments was also evaluated.

A 0.54 cm$^2$ section of human cadaver skin was mounted over a Franz cell receptor well. The receptor well was filled with receptor fluid comprising 3.30 mL of 2% w/w hydroxypropyl-3-cyclodextrine (HPBCD) and 0.01% w/w NaN$_3$. 5 µL of a rofecoxib topical composition was introduced into the donor well. Fluid samples were abstracted from the receptor after 4 hours, 8 hours, and 22 hours and analyzed for the presence of rofecoxib.

The rofecoxib topical compositions in Table 7 were evaluated.

TABLE 7

Rofecoxib Topical Compositions

| Name of Composition | Composition |
|---|---|
| Formulation 80 | DI (15% w/w); PC (5% w/w); BA (2.5% w/w); DMSO (20% w/w); DIA (12% w/w); PS20 (15% w/w); PGD (10% w/w); OA (5% w/w); DGME (8.5% w/w); Rofecoxib (2% w/w); Spearmint (0.33% w/w); Eucalyptus oil (0.67% w/w) |
| Formulation 82 | DI (15% w/w); PC (5% w/w); BA (2.5% w/w); DMSO (20% w/w); DIA (12% w/w); PS20 (15% w/w); DGME (18.5% w/w); OA (5% w/w); Rofecoxib (2% w/w); Spearmint (0.33% w/w); Eucalyptus oil (0.67% w/w) |
| Formulation 83 | DI (15% w/w); PC (5% w/w); BA (2.5% w/w); DMSO (20% w/w); DIA (12% w/w); PS20 (15% w/w); PGD (10% w/w); AT (5% w/w); DGME (8.5% w/w); Rofecoxib (2% w/w); Spearmint (0.33% w/w); Eucalyptus oil (0.67% w/w) |

Figure 4:
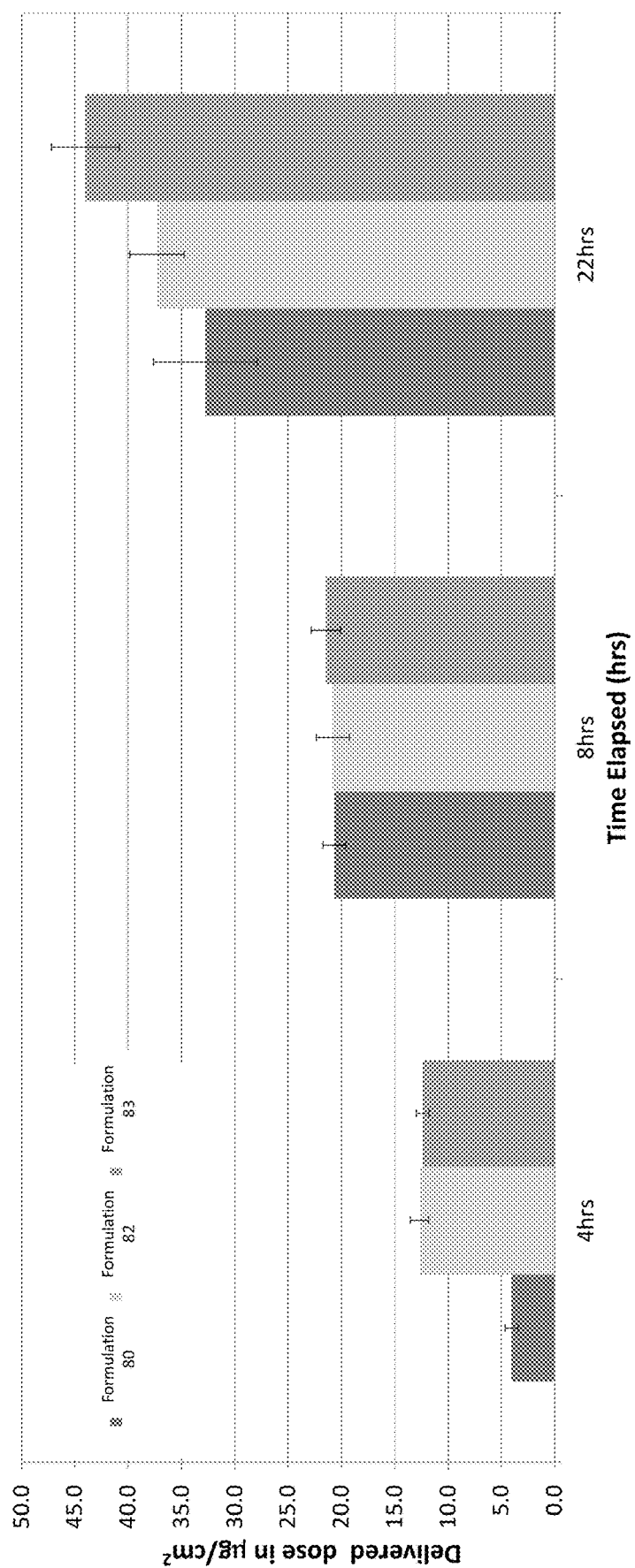
FIG. 4 shows the delivered dose of rofecoxib from rofecoxib topical compositions Formulations 80, 82, and 83 as described herein to human skin over time.
Figure 6:
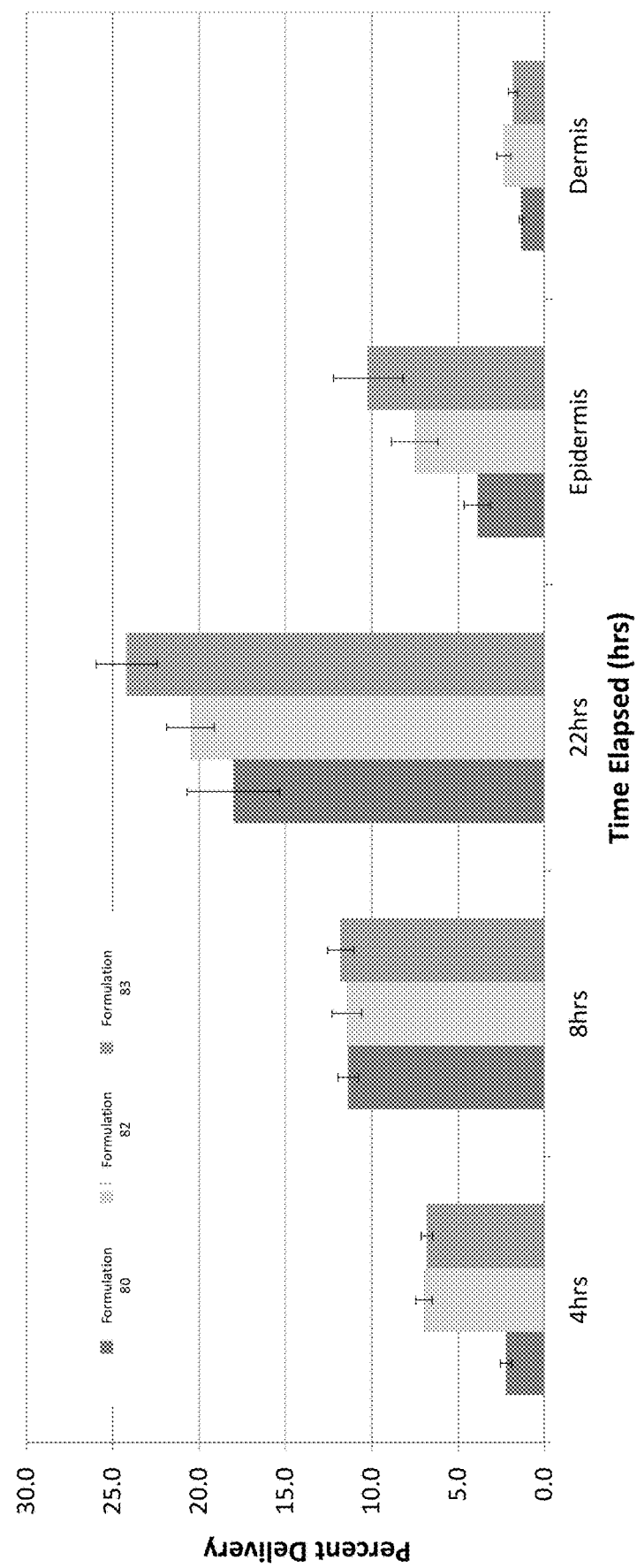
FIG. 6 shows the percentage of rofecoxib from rofecoxib topical compositions Formulations 80, 82, and 83 delivered to the skin over time and shows the percentage of rofecoxib delivered to the dermis and epidermis.
Figure 7:
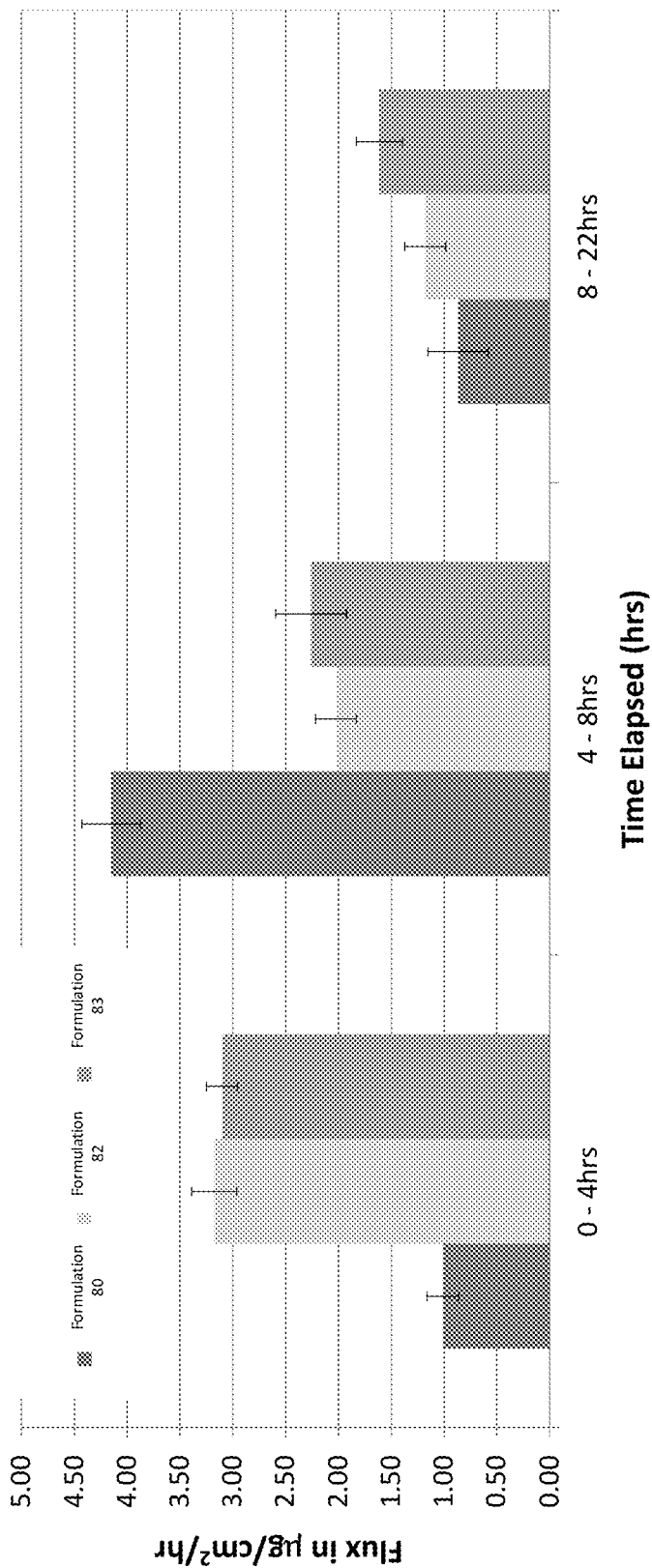
FIG. 7 shows the flux of the rofecoxib absorbed through the skin from the rofecoxib topical compositions Formulations 80, 82, and 83.

The amount of rofecoxib delivered over time, the percentage of rofecoxib delivered over time, and the flux of rofecoxib absorbed through the skin are reported in Tables 8, 9, and 10, respectively. FIG. 4 shows the delivered dose of rofecoxib over time. FIG. 6 shows the percentage of rofecoxib delivered over time. FIG. 7 shows the flux of the rofecoxib topical compositions.

18% of rofecoxib in the Formulation 80 diffused after 22 hours. 20.5% of rofecoxib in Formulation 82 diffused after 22 hours. 24.2% of rofecoxib in Formulation 83 diffused after 22 hours. In contrast, only 6% and 8%, respectively, of diclofenac in the commercially available Voltaren® gel and PENNSAID® topical NSAIDS diffuse within 24 hours. Topical rofecoxib compositions exhibit three times better diffusion suggesting better tissue penetration than diclofenac compositions. A rofecoxib topical composition is also desirable, because due to rofecoxib's half-life of 17 hours, a rofecoxib topical composition is suitable for once-a-day administration.

Figure 5:
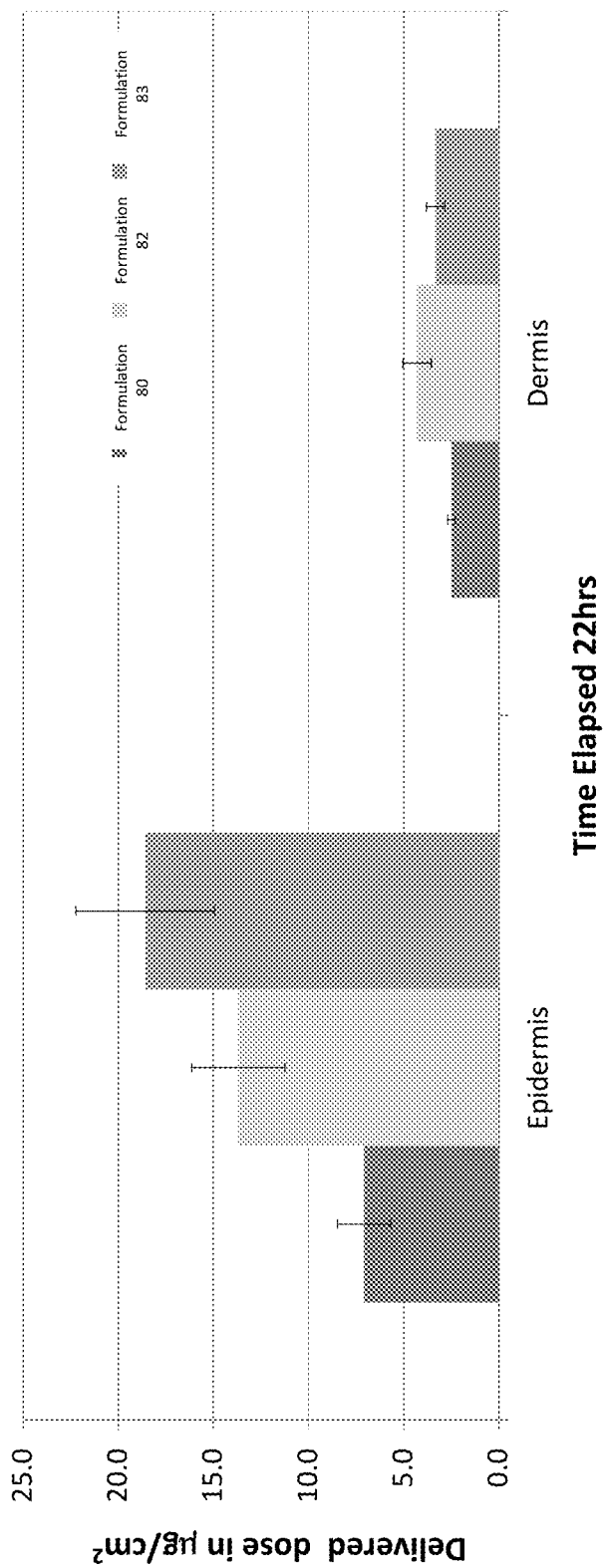
FIG. 5 shows the delivered dose of rofecoxib from rofecoxib topical compositions Formulations 80, 82, and 83 to the dermis and epidermis.

Tables 8 and 9 also show the amount of rofecoxib delivered to the dermis and epidermis and the percentage of rofecoxib delivered to the dermis and the epidermis, respectively. FIG. 5 shows the delivered dose of rofecoxib to the dermis and epidermis. FIG. 6 shows the percentage of rofecoxib delivered to the dermis and epidermis. Each of the rofecoxib topical compositions evaluated penetrated the dermis and epidermis.

TABLE 8

Rofecoxib Delivered Dose (reported in µg/cm$^2$)

| Formulation | 4 hours | | 8 hours | | 22 hours | | Epidermis | | Dermis | |
|---|---|---|---|---|---|---|---|---|---|---|
| | Dose | Standard Error | Dose | Standard Error | Dose | Standard Error | Dose | Standard Error | Dose | Standard Error |
| Formulation 80 | 4.05 | 0.6 | 20.65 | 1.07 | 32.79 | 4.88 | 7.08 | 1.4 | 2.49 | 0.2 |
| Formulation 82 | 12.7 | 0.85 | 20.8 | 1.56 | 37.31 | 2.52 | 13.69 | 2.45 | 4.29 | 0.74 |
| Formulation 83 | 12.41 | 0.59 | 21.44 | 1.38 | 44.01 | 3.19 | 18.58 | 3.64 | 3.31 | 0.49 |

TABLE 9

Percentage of Rofecoxib Delivered (reported as %)

| Formulation | 4 hours | | 8 hours | | 22 hours | | Epidermis | | Dermis | |
|---|---|---|---|---|---|---|---|---|---|---|
| | Percent Delivered | Standard Error | Percent Delivered | Standard Error | Percent Delivered | Standard Error | Percent Delivered | Standard Error | Percent Delivered | Standard Error |
| Formulation 80 | 2.23 | 0.33 | 11.36 | 0.59 | 18.03 | 2.68 | 3.89 | 0.77 | 1.37 | 0.11 |
| Formulation 82 | 6.99 | 0.47 | 11.44 | 0.86 | 20.52 | 1.39 | 7.53 | 1.35 | 2.36 | 0.41 |
| Formulation 83 | 6.82 | 0.32 | 11.79 | 0.76 | 24.21 | 1.75 | 10.22 | 2 | 1.82 | 0.27 |

TABLE 10

Flux of Rofecoxib Compositions (reported in µg/cm2/hr)

| Formulation | 4 hours | | 8 hours | | 22 hours | |
|---|---|---|---|---|---|---|
| | Flux | Standard Error | Flux | Standard Error | Flux | Standard Error |
| Formulation 80 | 1.01 | 0.15 | 4.15 | 0.28 | 0.87 | 0.29 |
| Formulation 82 | 3.18 | 0.21 | 2.02 | 0.19 | 1.18 | 0.19 |
| Formulation 83 | 3.1 | 0.15 | 2.26 | 0.34 | 1.61 | 0.22 |

Example 4. Stability Testing of Rofecoxib Topical Compositions

The solubility of rofecoxib in the presence of solvents selected from the Food and Drug Administration's Inactive Ingredient Database (IID) for use in a topical product was evaluated. Table 11 shows the solubility of rofecoxib in various solvents.

TABLE 11

Solubility of Rofecoxib in Various Solvents by High Performance Liquid Chromatography

| Solvent | Solubility of Rofecoxib (% w/w) |
|---|---|
| 1.25% Niacinamide (Aqueous) | No observable solubility |
| 10% Sodium Lauryl Sulfate (Aqueous)* | No observable solubility* |
| Dehydrated Alcohol | No observable solubility |
| Diethyl Sebacate | No observable solubility |
| Diethylene Glycol Monoethyl Ether* | 0.5-1.0 |
| Diisopropyl Adipate | No observable solubility |
| Dimethyl Isosorbide* | 2.5-3.5% |
| Ethyl Acetate | <0.5% |
| Glyceryl Monooleate | No observable solubility |
| Hydrochloric Acid (0.1 N) | No observable solubility |
| Laureth-4 | No observable solubility |
| Medium Chain Triglycerides | No observable solubility |
| N-Methyl-Pyrrolidone* | 4.4-5.4 |
| Oleyl Alcohol | No observable solubility |
| PEG400* | 1.0-1.5 |
| Polysorbate 80 | No observable solubility |
| Propylene Carbonate* | 3.4-4.3 |
| Propylene Glycol Diacetate | <0.5 |
| Sodium Hydroxide (0.1 N)* | No observable solubility |
| Sorbitol Solution | No observable solubility |
| Water pH 3 | No observable solubility |
| Water pH 5.5 | No observable solubility |
| Water pH 7.4 | No observable solubility |

*Color Change Observed, colorless to yellow

The stability of rofecoxib was assessed by HPLC after storage for two weeks at 40° C. and for two weeks at 50° C. Table 12 shows the solubility of rofecoxib in various solvents after two weeks at 40° C. and at 50° C. Rofecoxib, which was solubilized in the solvents in Table 12, remained soluble for two weeks at 40° C. and 50° C.

TABLE 12

Solubility of Rofecoxib after 2 weeks at 40° C. and 50° C.

| Solvent | Rofecoxib Concentration (% w/w) | | |
|---|---|---|---|
| | T = 0 weeks | T = 2 weeks 40° C. storage | T = 2 weeks 50° C. storage |
| Acetone | 2.549 | 2.549 | 2.549 |
| Benzyl alcohol | 1.447 | 1.474 | 1.470 |
| Diethylene glycol monoethyl ether | 0.687 | 0.672 | 0.677 |
| Dimethyl isosorbide | 2.641 | 2.515 | 2.511 |
| Ethyl acetate | 0.465 | 0.479 | 0.476 |
| N-methyl-2-pyrrolidone | 5.046 | 5.057 | 5.055 |
| PEG 400 | 1.013 | 0.987 | 0.993 |
| Propylene Carbonate | 3.471 | 3.456 | 3.463 |
| Propylene Glycol Diacetate | 0.519 | 0.527 | 0.520 |

Future experiments will test the stability of the rofecoxib topical compositions of the disclosure at additional time points, including 1 month, 2 months, 3 months, 4 months, 5 months, 6 months, 7 months, 8 months, 9 months, 10 months, 11 months, and 12 months.

Example 5. Effect of Rofecoxib Topical Compositions on Pain and Inflammation

A study in rats was conducted to evaluate the effect of rofecoxib topical compositions on pain and inflammation. On study day 0, 55 Male Sprague Dawley rats were weighed and randomized by body weight. Subsequently animals were anesthetized with isoflurane and administered a 0.04 mL intra-articular injection of Freund's incomplete adjuvant supplemented by *Mycobacterium butyricum* into the right knee. Administration of Freund's incomplete adjuvant and *Mycobacterium butyricum* causes symptoms of arthritis in the rats, including pain and inflammation. On study day 2, animals underwent gait testing and were randomized into groups based on gait scores.

On study day 3, animals were administered a rofecoxib topical composition (e.g., Formulation 85), a rofecoxib vehicle that contained the rofecoxib topical composition's solvent system but lacked rofecoxib, or oral rofecoxib (10 mg/kg). As a control, naïve rats were not administered Freund's incomplete adjuvant and were administered a vehicle comprising 15.15% w/w dimethyl isosorbide, 5.05% w/w propylene carbonate, 2.53% w/w benzyl alcohol, 10.10% of 10% DMSO, 10.1% diisopropyl adipate, 45.45 w/w polyethylene glycol 400, 7.58% w/w oleic acid, 3.03% HPC, 0.33% *eucalyptus* oil, and 0.68% w/w spearmint oil. Formulation 85 contained 2% w/w rofecoxib, 15% w/w dimethyl isosorbide, 5% w/w propylene carbonate, 2.5% w/w benzyl alcohol, 20% w/w dimethyl sulfoxide, 12% w/w diisopropyl adipate, 18.5% w/w diethylene glycol monoethyl ether, 15.0% polysorbate 20 (PS20), 5 w/w oleic acid, 4% w/w hydroxypropyl cellulose (MW=100,000 Da), 0.33% w/w *eucalyptus* oil, and 0.67% w/w spearmint oil. Formulation 85 vehicle contained 15.31% w/w dimethyl isosorbide, 5.1 w/w propylene carbonate, 2.55% benzyl alcohol, 20.41% w/w DMSO, 12.24% diisopropyl adipate, 18.88% w/w diethylene glycol monoethyl ether, 15.31% w/w PS20, 5.1% w/w oleic acid, 4.08% w/w HPC, 0.34% w/w *eucalyptus* oil, and 0.68% w/w spearmint oil. The animals were administered the rofecoxib topical composition once daily.

Table 13 shows the study groups evaluated.

TABLE 13

Study Groups

| Group | N | Compound and/or Treatment | Dose (% or mg/kg) | Regimen | Dose Vol (ml) | Dose Conc (mg/ml) |
|---|---|---|---|---|---|---|
| 1 | 5 | Naive | 0 | Top, QD, D3 | 0.1 | 0 |
| 4 | 10 | Formulation 85 Vehicle | 0 | Top, QD, D3 | 0.1 | 0 |
| 5 | 10 | Formulation 85 | 2% | Top, QD, D3 | 0.1 | 2.4 |
| 6 | 10 | rofecoxib | 10 mg/kg | PO, QD, D3 | 5 ml/kg | 2 |

Table 14 shows the study calendar.

TABLE 14

Study Calendar

| Day -7 | Day -6 | Day -5 | Day -4 | Day -3 | Day -2 | Day -1 |
|---|---|---|---|---|---|---|
| Distribute rats on arrival into groups for acclimation | | | | | | |

| Day 0 | Day 1 | Day 2 | Day 3 | Day 4 | Day 5 | Day 6 |
|---|---|---|---|---|---|---|
| Assign randomization numbers, inject adjuvant IA into right knee | | Weigh, gait, randomize animals by gait | Dose, Gait, Bleed | Gait, necroscopy | | |

Gait testing was performed four hours, 8 hours, and 24 hours post-dosing. Gait measurements were conducted by applying ink to the ventral surface of the foot and documenting weight bearing during movement (footprints) across paper. Rear feet of rats were placed in ink and then rats were placed on paper and allowed to walk the full length. This process was repeated as necessary to generate 4 clear, evenly inked footprint pairs representing the overall pattern of gait. Gait (foot prints) will be scored visually as follows (descriptions refer to diseased leg): 0=Normal, approximately equal ink staining to normal paw; 1=Slight limp/pain=reduced inking area relative to the normal paw, but no full regions or structures are missing; 2=Mild limp/pain=Print extends to the end or near to the end of the "curlicue" structure. If normal paw has very little heel staining (rat walks mainly on toes/ball of foot), then slightly less staining; 3=Moderate limp/pain=toes and full ball of foot, extending to the top of the "curlicue" foot. If normal paw has very little heel staining (rat walks mainly on toes/ball of foot), then toes with small portion of ball of foot; 4=Marked limp/pain=toes and partial ball of foot, no heel or posterior foot. If normal paw has very little heel staining (rat walks mainly on toes/ball of foot), then toes only; 5=Severe limp/pain=toes only, no ball of foot, no heel. If normal paw has very little heel staining (rat walks mainly on toes/ball of foot), then partial toes or non-specific marks; 6=Hopping or Carrying leg, no footprint is evident.

Knee caliper measurements were taken daily. Caliper measures of right and left knee diameters were performed on assigned days using a Digitrix II micrometer caliper (Fowler & NSK). Baseline knee caliper measurements were taken using one knee with values rounded to one-thousandth of an inch. Measurements were confirmed as clinically normal by comparison with historical values for rats based on a range of body weights. Baseline measurements were then applied to both knees, and these values remain with the animal so long as the knee is clinically normal.

Figure 8:
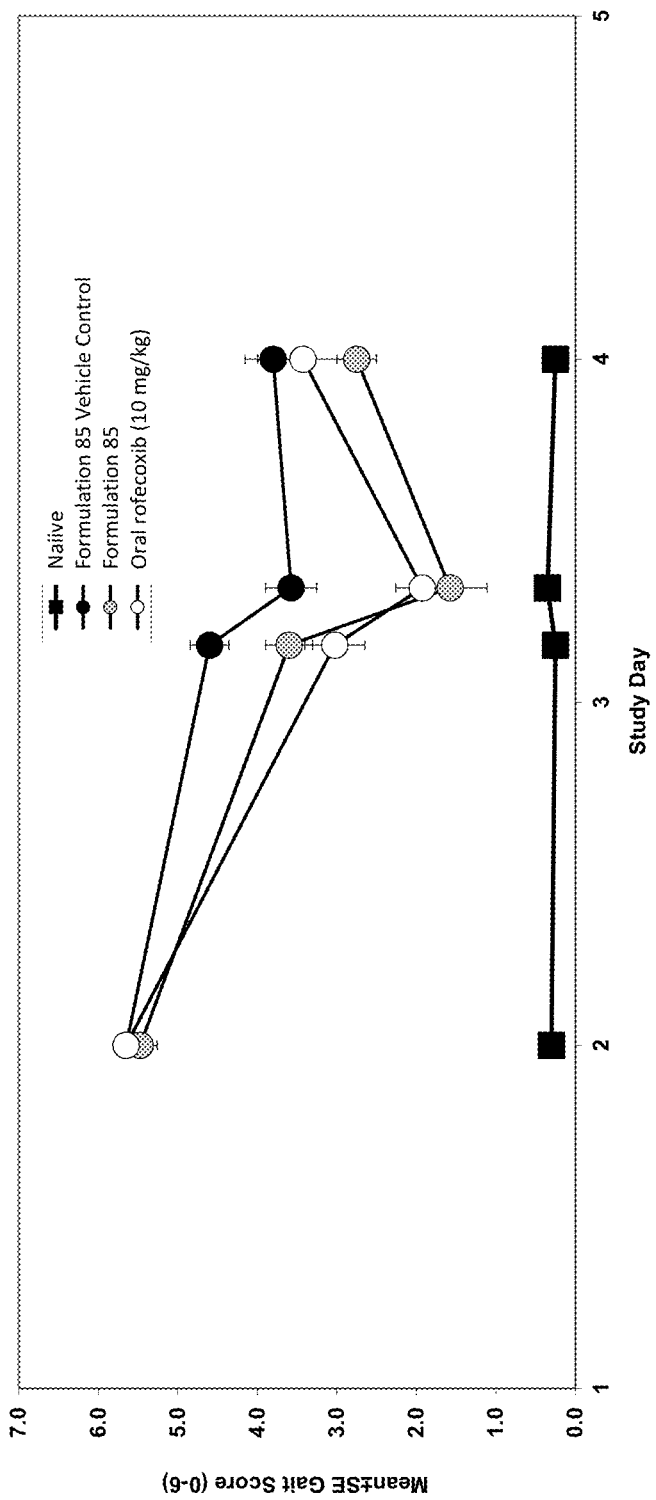
FIG. 8 shows the effect of the rofecoxib topical composition Formulation 85 on gait score.
Figure 9:
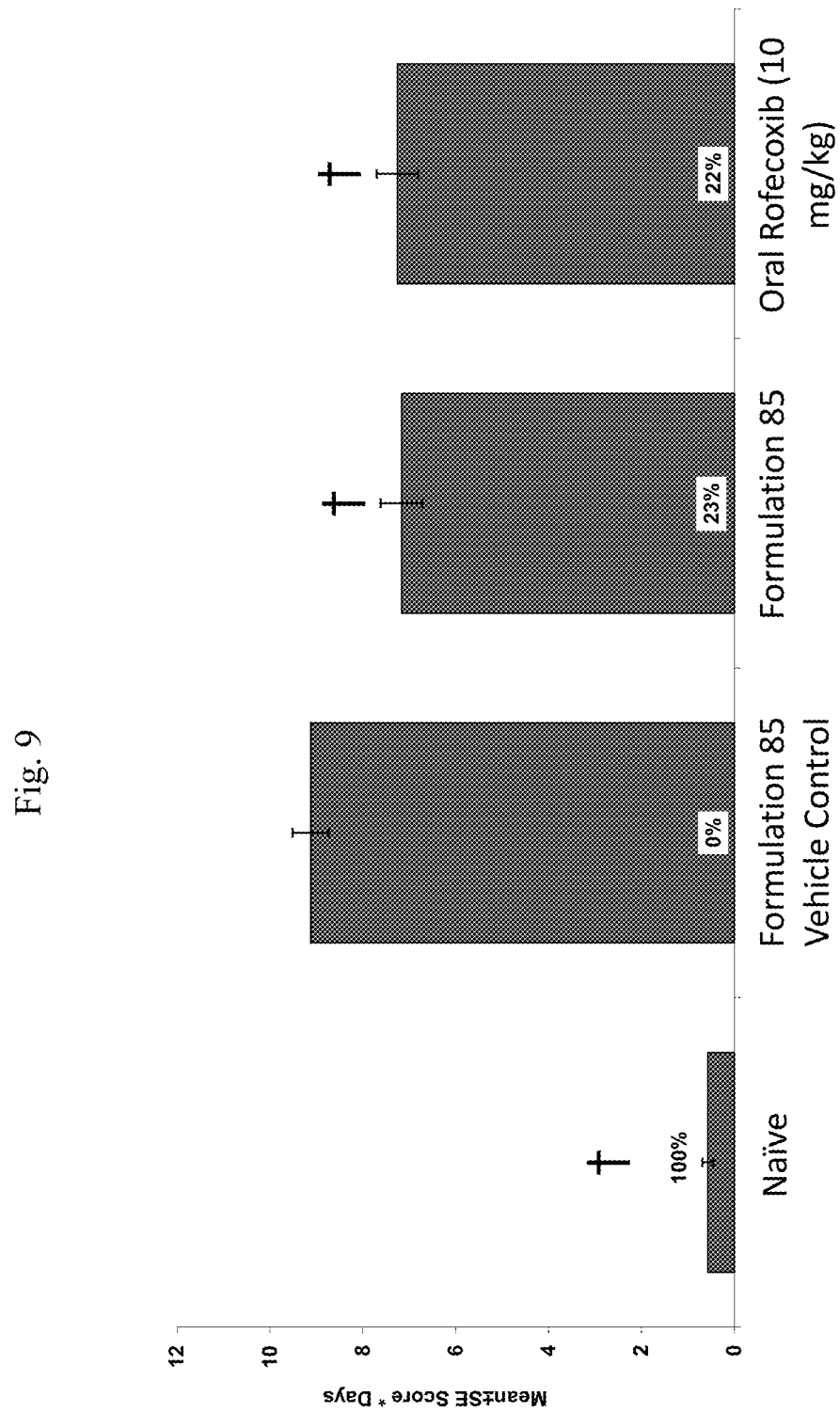
FIG. 9 shows the effect of rofecoxib topical composition Formulation 85 on the area under the curve of gait score calculated from 4 hours to 22 hours of rats in a rat model of arthritis.

FIG. 8 shows the effect of the rofecoxib topical composition Formulation 85 on gait score. By eight hours post dosing of Formulation 85, the gait of the treated rats improved. Surprisingly, rofecoxib topical formulation 85 caused a greater improvements in rat gait than the oral rofecoxib formulation. FIG. 9 show the area under the curve of gait score calculated from 4 hours to 22 hours. A Kruskal-Wallis post-hoc analysis using Dunn's nonparametric comparison revealed that in comparison to the Formulation 85 vehicle control, Formulation 85 significantly reduced the gait score (†$p<0.05$). These results collectively show that topical rofecoxib compositions reduce pain.

Figure 10:
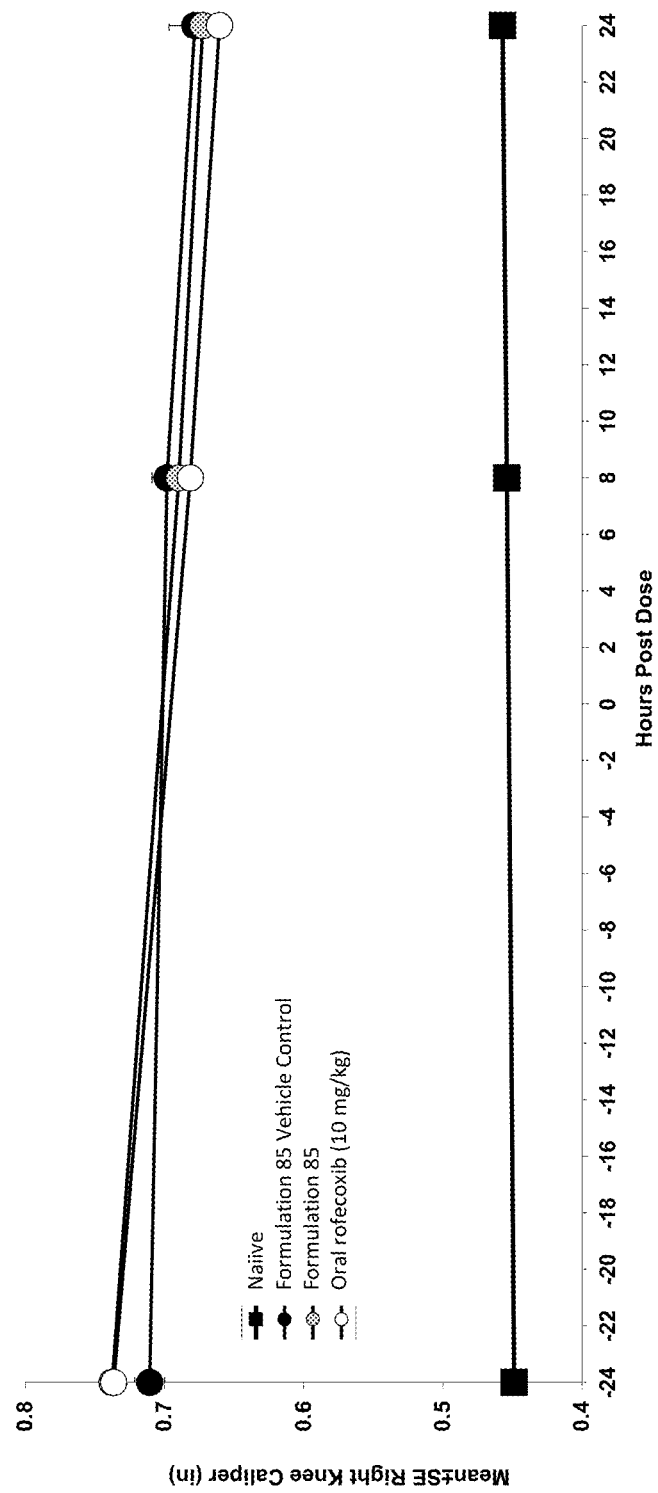
FIG. 10 shows the effect of rofecoxib topical composition Formulation 85 on right knee caliper measurement.
Figure 11:
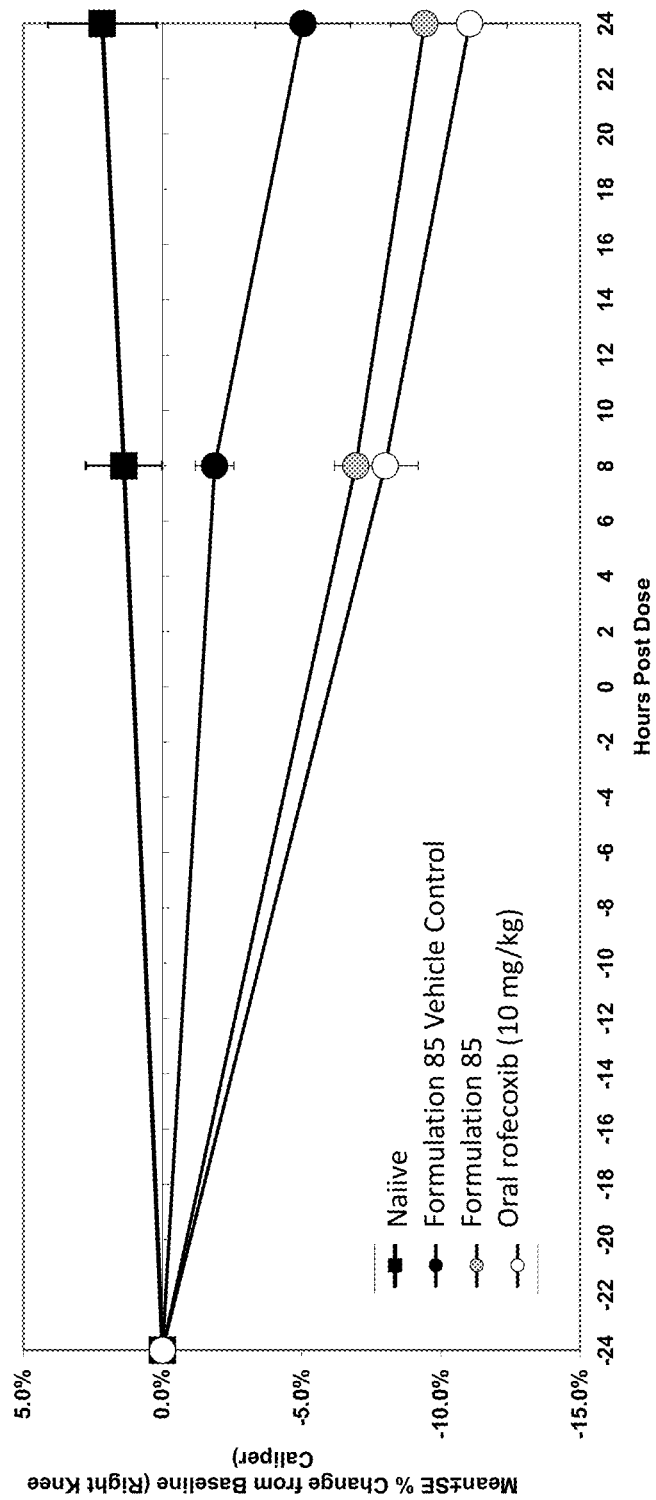
FIG. 11 shows the effect of rofecoxib topical composition Formulation 85 on the percentage change in right knee caliper measurement from baseline.
Figure 12:
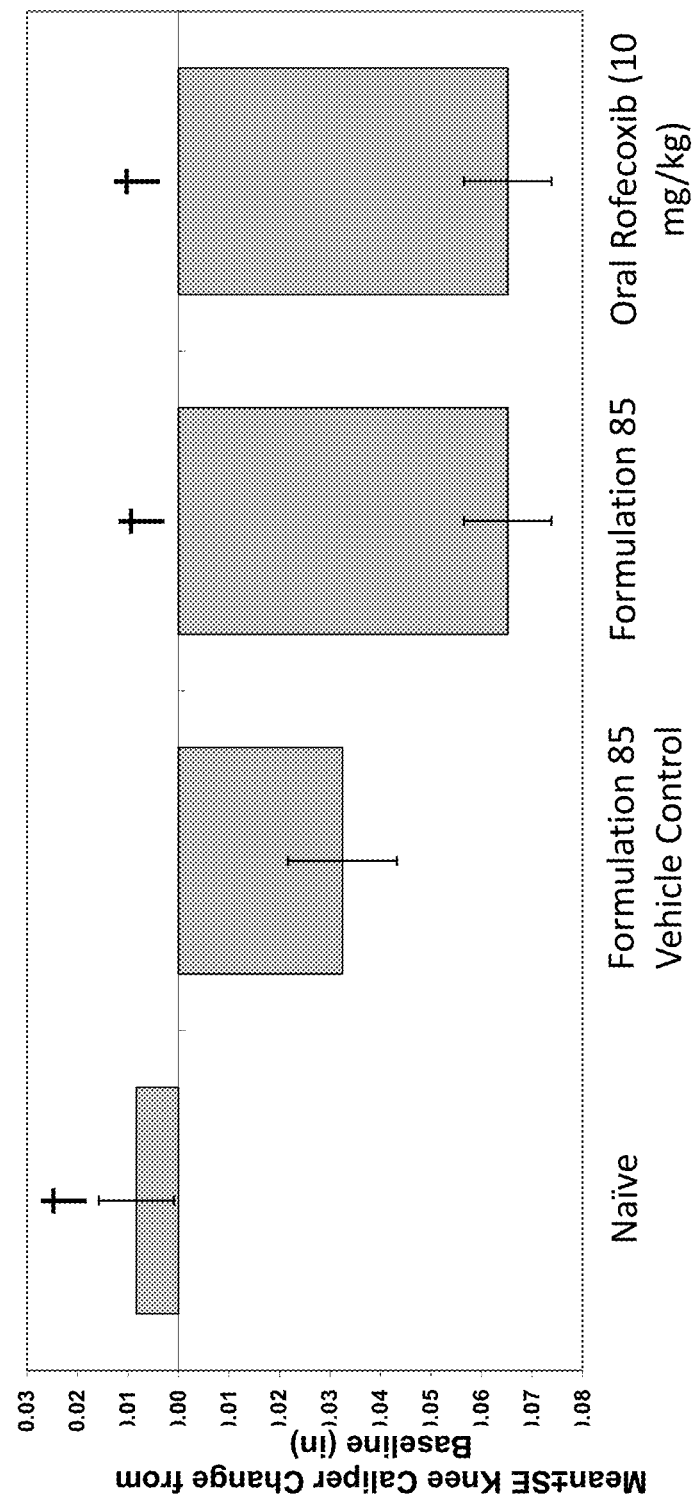
FIG. 12 shows the effect of rofecoxib topical composition Formulation 85 on the average right knee caliper change from baseline measured in inches.
Figure 13:
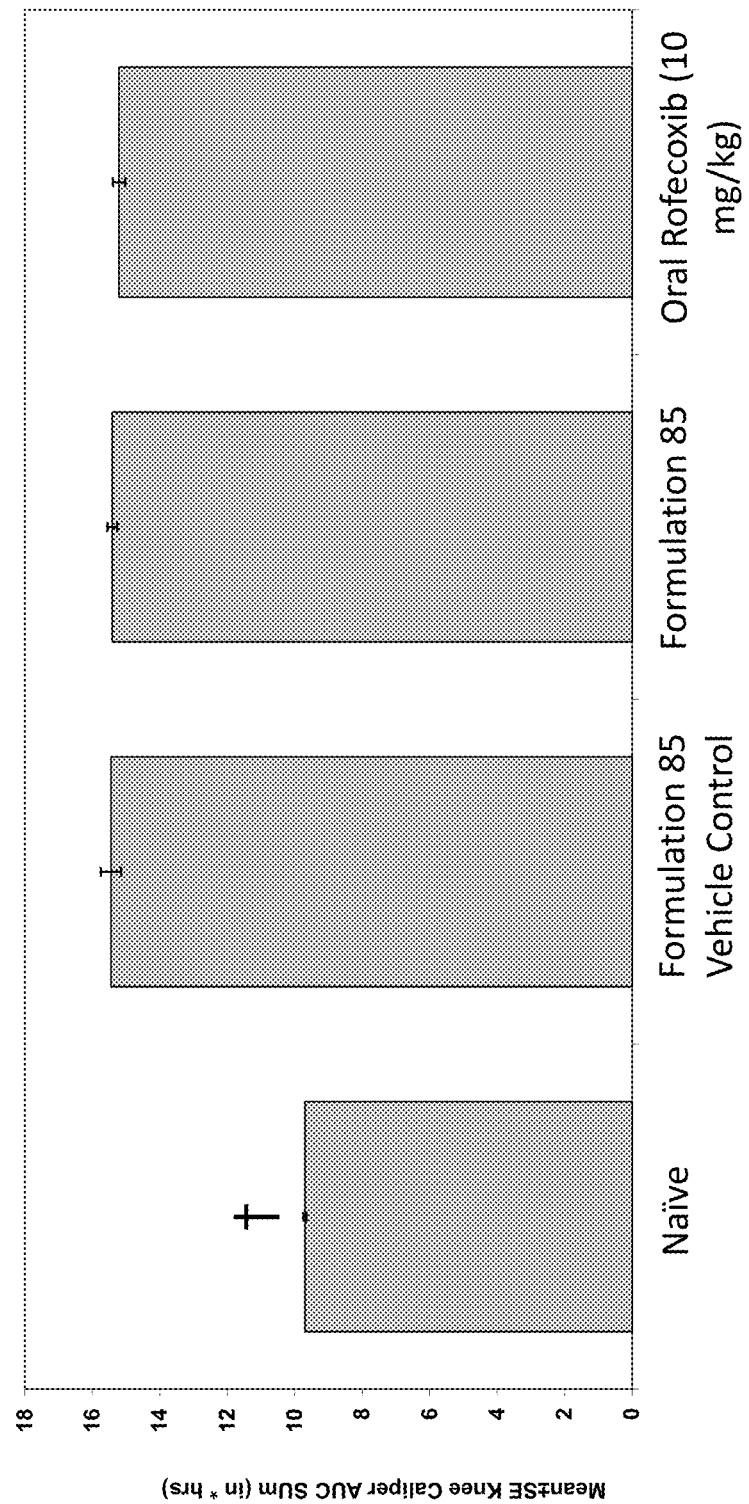
FIG. 13 shows the effect of rofecoxib topical composition Formulation 85 on the mean area under the curve for knee caliper measurement.

FIG. 10 shows right knee caliper measurements after administration of the rofecoxib topical composition Formulation 85. FIG. 11 shows the percent change in right knee caliper measurement from baseline. The average right knee caliper change from baseline measured in inches for the rofecoxib topical composition Formulation 85 is displayed in FIG. 12. In comparison to vehicle control treated rats, rats treated with rofecoxib topical compositions displayed a reduction in right knee caliper measurement, consistent with a reduction in inflammation. FIG. 13A, FIG. 13B, and FIG. 13C show the mean area under the curve for knee caliper measurement. A one-way analysis of variance (ANOVA) using Tukey and Dunnett's methods showed that in comparison to the Formulation 85 vehicle control, Formulation 85 significantly reduced inflammation (†$p<0.05$).

Example 6. Pharmacokinetic Study of Rofecoxib Formulation in Miniature Swine

A study in Hanford miniature swine was conducted to evaluate the pharmacokinetics of rofecoxib topical compositions. The Hanford miniature swine used in the study were males, aged 0.2 to 0.4 years, which weighed between 10 and 20 kg.

The experimental design for the study is shown in Table 15 below.

TABLE 15

Experimental Design

| Treatment | Dose Route | Number of animals | Dose Conc. (mg/mL) | Dose volume (mL/kg) | Dose level (mg/kg) |
|---|---|---|---|---|---|
| Oral Rofecoxib | PO[a] | 2M | 0.10 | 2 | 0.2 |
| Formulation 85 | Topical[b] | 2M | 20 | 1.25[c] | NA[c] |

The dose level of the oral arm of this pharmacokinetic study was based on the lowest effective human dose of rofecoxib previously approved by the FDA for use in humans, 12.5 mg. The dose levels of the test articles in the topical administration arms were selected based on the expected dermal penetration to provide circulating blood levels similar to or below the oral administration.

Animals in the oral rofecoxib group were administered oral rofecoixb once daily via oral gavage followed by up to 10 mL of tap water to facilitate swallowing. Animals in the topical rofecoxib group were administered Formulation 85 once on Dosing Phase Day 1 and twice-daily on Dosing Phase Days 2 to 7, 8 hours apart, via dermal administration to 10% body surface area.

Dose sites were observed for skin irritation using the Modified Draize scoring system detailed below in Table 16.

TABLE 16

Modified Draize Scoring System

| Category | Score | Description |
|---|---|---|
| Erythema | 0 | None |
| | 1 | Slight |
| | 2 | Well-defined |
| | 3 | Moderate or severe |
| | 4 | Severe or slight eschar formation (injuries in depth) |
| Edema | 0 | None |
| | 1 | Very slight |
| | 2 | Slight (well-defined edges) |
| | 3 | Moderate (raised > 1 mm) |
| | 4 | Severe (raised > 1 mm and extending beyond the area of exposure) |

Whole blood (2 mL) was collected on all study animals on Dosing Phase Days 1 and 7 at each designated time point (Table 17) via direct venipuncture of the jugular vein (or other appropriate vessel). Synovial fluid was collected from both knees of each animal at euthanasia.

TABLE 17

Pharmacokinetic Sample Collection Scheme
Pharmacokinetic Sample Collection Scheme

| Groups | Intervals | Target Time Points |
|---|---|---|
| All | Dosing Phase Days 1 and 7 | Predose, 0.25, 0.5, 1, 2, 4, 8 (prior to 2nd dose on Dosing Phase Day 7), 12 and 24 hours post dose |

The following pharmacokinetic parameters were evaluated:

TABLE 18

Pharmacokinetic Parameters

| Parameter | Description |
|---|---|
| $C_{max}$ | Maximum observed concentration of rofecoxib |
| $T_{max}$ | Time of $C_{max}$ relative to dosing |
| $T_{1/2}$ | Calculated elimination half-life |
| AUC | Area under concentration by time curve |
| Accumulation | Comparison of values from Dosing Phase Day 1 to Day 7 |

Pharmacokinetic Methods:

A non-compartmental pharmacokinetic (PK) approach consistent with either oral or topical route of administration was used to estimate PK parameters in Watson LIMS (version 7.5). All parameters were generated from individual concentrations in plasma whenever practical. BQL data was set to zero for the samples at time 0 (pre-dose) and was excluded for all other time points post dose for the calculation of toxicokinetic parameters. All concentration values were in ng/mL, and all time points were in hours. Nominal doses and sampling times were used. The observed maximum plasma concentration ($C_{max}$), time of $C_{max}$ ($T_{max}$), and AUC (area under the concentration vs. time curve) were determined directly from the data during the entire 24 hour time interval post dosing. Standard deviation and coefficient of variation determined by Watson LIMS were computed when possible. For analyses that were not supported by Watson, i.e. custom comparisons, Excel was used and the statistics were reported as determined by excel algorithms. Note that in either case, when the number of data points was less than three, standard deviation and coefficient of variation could not be calculated.

Safety:

After administration of Formulation 85, all animals in the study exhibited a Modified Draize score of 0, indicating that the formulation did not produce skin irritation.

Figure 14A:
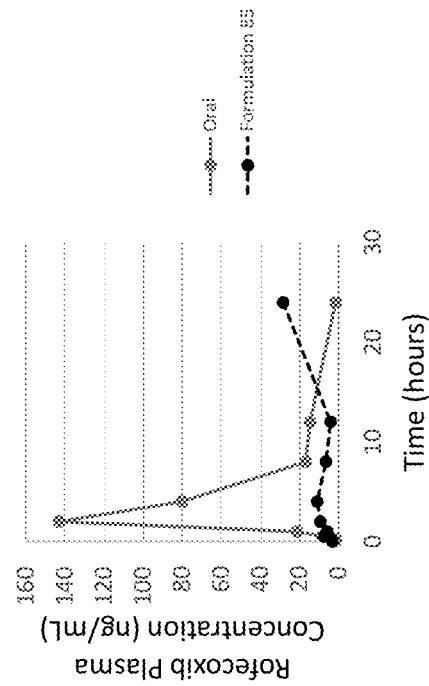
FIG. 14A shows the plasma concentrations of rofecoxib over time after administration of oral rofecoxib or topical rofecoxib Formulation 85 on dosing day 1.
Figure 14B:
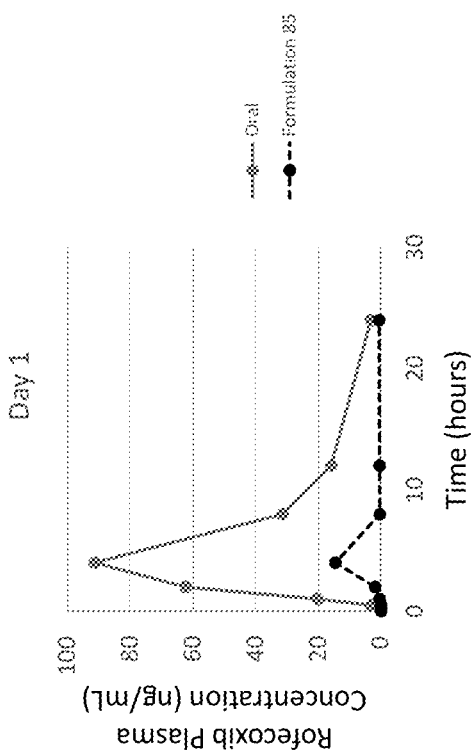
FIG. 14B shows the plasma concentrations of rofecoxib over time after administration of oral rofecoxib or topical rofecoxib Formulation 85 on day 7.

Pharmacokinetic Results:

Table 19 and FIG. 14A shows the plasma concentrations of rofecoxib over time after administration of oral rofecoxib or topical rofecoxib Formulation 85 on dosing day 1. Table 19 and FIG. 14B shows the plasma concentrations of rofecoxib over time after administration of oral rofecoxib or topical rofecoxib Formulation 85 on day 7.

TABLE 19

Plasma Concentration of Rofecoxib over Time

| | Day 1 | | Day 7 | |
|---|---|---|---|---|
| | Treatment Rofecoxib Concentration (ng/mL) | | | |
| Time (hours) | Oral Rofecoxib | Formulation 85 | Oral Rofecoxib | Formulation 85 |
| 0 | 0 | 0 | 1.74 | 3.49 |
| 0.25 | 0 | 0 | 1.57 | 4.11 |
| 0.5 | 3.09 | 0 | 8.15 | 7.51 |
| 1 | 20.2 | 0.442 | 21.4 | 5.97 |
| 2 | 62.4 | 1.84 | 143 | 9.43 |
| 4 | 91.4 | 14.5 | 80 | 11.1 |
| 8 | 31.5 | 0.326 | 16.95 | 6.58 |
| 12 | 15.9 | 0.426 | 14.7 | 4.24 |
| 24 | 3.15 | 0.535 | 1.68 | 28.5 |

Figures 15A, 15B:
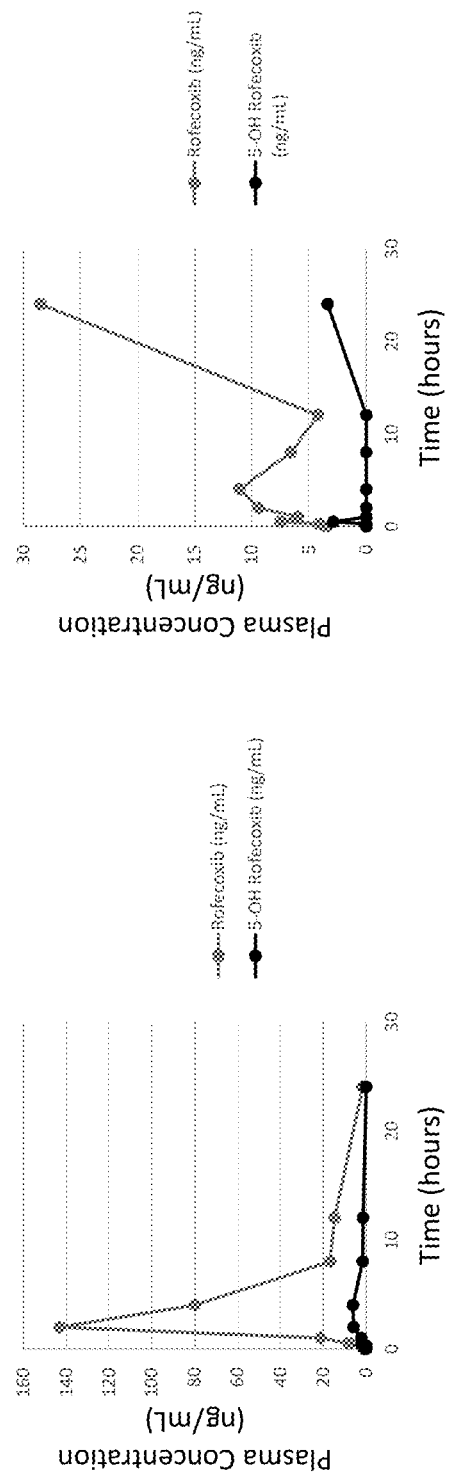
FIG. 15A shows the plasma concentration of 5-OH and the plasma concentration of rofecoxib after administration of oral rofecoxib.
FIG. 15B shows the plasma concentration of 5-OH and the plasma concentration of rofecoxib after administration of Formulation 85.

Table 20A shows the plasma concentration of 5-OH-rofecoxib, a metabolite of rofecoxib after administration of Formulation 85 or oral rofecoxib. FIG. 15A shows the plasma concentration of 5-OH and the plasma concentration of rofecoxib after administration of oral rofecoxib. FIG. 15B shows the plasma concentration of 5-OH and the plasma concentration of rofecoxib after administration of Formulation 85.

TABLE 20A

Plasma Concentration of Rofecoxib and 5-OH-rofecoxib over time

|  | Oral Rofecoxib | | Formulation 85 | |
| --- | --- | --- | --- | --- |
| Time (hours) | Rofecoxib (ng/mL) | 5-OH-Rofecoxib (ng/mL) | Rofecoxib (ng/mL) | 5-OH-Rofecoxib (ng/mL) |
| 0 | 1.74 | 0 | 3.49 | 0 |
| 0.25 | 1.57 | 0 | 4.11 | 0 |
| 0.5 | 8.15 | 2.25 | 7.51 | 2.89 |
| 1 | 21.4 | 2.33 | 5.97 | 0 |
| 2 | 143 | 5.95 | 9.43 | 0 |
| 4 | 80 | 6.18 | 11.1 | 0 |
| 8 | 16.95 | 1.74 | 6.58 | 0 |
| 12 | 14.7 | 1.47 | 4.24 | 0 |
| 24 | 1.68 | 0 | 28.5 | 3.39 |

The data shows that rofecoxib administered in a topical formulation is absorbed.

The amount of rofecoxib and 5-OH-Rofecoxib in synovial fluid was also quantitated. Table 20B shows the amount of rofecoxib and 5-OH rofecoxib in synovial fluid after administration of oral rofecoxib or Formulation 85.

TABLE 20B

Plasma Concentration of Rofecoxib and 5-OH-rofecoxib over time in the synovial fluid

|  | Oral Rofecoxib | Formulation 85 |
| --- | --- | --- |
| Rofecoxib (ng/mL) | 0 | 0 |
| 5-OH Rofecoxib (ng/mL) | 11.4 | 0 |

The pharmacokinetic parameters Cmax, Tmax, and AUC were also evaluated (Table 21).

TABLE 21

Pharmacokinetic Parameters for Rofecoxib after Administration of Oral Rofecoxib or Formulation 85

| Mean Values, | | Oral Rofecoxib | | | Formulation 85 | | |
| --- | --- | --- | --- | --- | --- | --- | --- |
| Plasma Rofecoxib Oral and Topical | | Day 1 | Day 7 | Day 7/ Day 1 Ratio | Day 1 | Day 7 | Day 7/ Day 1 Ratio |
| Parameter | Units | | | | | | |
| Cmax | ng/mL | 91.4 | 143 | 1.57 | 14.5 | 29.9 | 2.06 |
| Tmax | Hours | 4.00 | 2.00 | 0.500 | 4.00 | 14.0 | 3.50 |
| AUC | ng*Hours/mL | 610 | 579 | 0.950 | 39.3 | 237 | 6.04 |
| Cmax/Dose | ng/mL/mg | 22.9 | 35.8 | 1.57 | 0.580 | 0.598 | 1.03 |
| AUC/Dose | ng*Hours/mL/mg | 153 | 145 | 0.950 | 1.57 | 4.75 | 3.02 |
| Original Dose | mg | 4.00 | 4.00 | 1.00 | 25.0 | 50.0 | 2.00 |

Formulation 85 obtained a Cmax of 15.9% of the oral formulation on day 1 and 20.9% of the oral formulation on day 7. Formulation 85 obtained an AUC of 6.4% of the oral formulation on Day 1 and 41% of the oral formulation on day 7.

A comparison of the pharmacokinetic parameters of Formulation 85 to commercially available diclofenac gel (available as VOLTAREN® gel) and diclofenac sodium topical solution (available as PENNSAID™) is shown in Table 22. The pharmacokinetic parameters obtained from the miniature swine data can be extrapolated to humans by taking into account the difference in surface area between humans and swine. Humans are three times larger than swine, so humans would, to a first-approximation, exhibit a 3-fold dilution in exposure compared to swine.

TABLE 22

Formulation 85's Pharmacokinetic Parameters compared to Commercially Available Topical NSAID formulations

|  | Formulation 85 (25 mg twice per day) | VOLTAREN ® (120 mg 4 times a day) | PENNSAID ™ (40 mg 4 times a day) |
| --- | --- | --- | --- |
| Cmax | 20.9% | 2.2% | 0.85% |
| Tmax | 14.0% | 10% | 4% |
| AUC | 41% | 19.7% | 19.4% |

As Table 22 shows, Formulation 85 is more bioavailable than the NSAID topical formulations VOLTAREN® and PENNSAID™.

Example 7. A Phase 1, Randomized, Double-Blind, Placebo-Controlled, Dose Escalation Study Evaluating the Safety, Tolerability, Pharmacokinetics, and Pharmacodynamics of Topical Rofecoxib in Subjects with Osteoarthritis of a Knee This Phase 1 trial evaluates the safety, tolerability, pharmacokinetics, and pharmacodynamics of single and multiple topical applications of Rofecoxib in subjects with OA of the knee. The incidence, relatedness, severity, and duration of treatment adverse events (TEAEs) is evaluated. The maximum tolerated dose of topical rofecoxib is determined. Subjects are administered a topical rofecoxib composition or placebo to the knee affected with OA.

Pharmacokinetic properties of rofecoxib in plasma are also evaluated, including the maximum observed plasma concentration (Cmax), dose-adjusted Cmax (Cmax/dose), time to maximum observed plasma concentration (Tmax), area under the plasma concentration versus time curve from time zero to the last quantifiable concentration ($AUC_{0-t}$), the dose adjusted $AUC_{0-t}$ ($AUC_{0-t}$/dose), AUC from time zero to infinity ($AUC_{0-\infty}$), the dose-adjusted $AUC_{0-\infty}$ ($AUC_{0-\infty}$/dose), terminal elimination rate constant ($t_{1/2}$), terminal half-life, apparent clearance (CL/F), and volume of distribution (Vz/F). Descriptive statistics for pharmacokinetics parameters by treatment group includes number of observations, arithmetic mean, standard deviation, arithmetic coefficient of variation (% CV), geometric mean, median, geometric % CV, minimum, and maximum. Dose proportionality is explored.

The pharmacodynamics (PD) of topical rofecoxib is evaluated by examining several exploratory endpoints, including serum N-propeptide of collagen IIA (PIIANP), C-telopeptide of type II collagen (CTX-II), pain and physical functioning as assessed by the Western Ontario and McMaster Universities Arthritis Index (WOMAC), and magnetic resonance (MR) imaging data. The pre-treatment values for these endpoints is compared to post-treatment measurements and both the absolute and percent change from baseline is summarized. Descriptive statistics for PD endpoints by time point and by treatment group will include number of observations, arithmetic mean, standard deviation, arithmetic coefficient of variation (% CV), median, minimum, and maximum. An exploratory analysis of PK/PD endpoints is performed.

A schedule of a single-ascending dose cohort schedule of assessments is presented in Table 23. A schedule of a multiple-ascending dose cohort schedule of assessments is presented in Table 24.

TABLE 23

Study Calendar of a Single-ascending dose cohort schedule of assessments

| VISIT NAME | SCREENING | DAY 1$^K$ | | | | | | | | DAY 2$^A$ | DAY 8 | DAY 29$^A$ |
|---|---|---|---|---|---|---|---|---|---|---|---|---|
| VISIT NUMBER | 1$^I$ | 2 | | | | | | | | 3 | 4 | 5 |
| TIME POST DOSE | NA | PRE DOSE$^J$ | 0 | 15 MIN | 30 MIN | 60 MIN | 90 MIN | 2 HRS | 4 HRS | | | |
| ALLOWABLE WINDOW | −28 to −1 days | | | +/− 2 Min | +/− 3 Min | +/− 5 Min | +/− 5 Min | +/− 5 Min | +/− 5 Min | | +/− 1 Day | + 3 Days |
| Informed Consent | X | | | | | | | | | | | |
| Demography | X | | | | | | | | | | | |
| Medical History | X | | | | | | | | | | | |
| Prior & Concomitant Treatments | X | X | | | | | | | | X | X | X |
| Physical Examination | X | X | | | | | | | | | X | |
| Height | X | | | | | | | | | | | |
| Weight | X | X | | | | | | | | | X | |
| Vital Signs$^B$ | X | X | | X | X | X | X | X | X | | X | |
| 12-Lead ECG | X | X | | | | | | | | | X | |
| Tibial-Femoral Radiographs$^C$ | X | | | | | | | | | | | |
| Safety Laboratory Tests$^D$ | X | X | | | | | | | | | X | |
| Urine Drug Screen | X | | | | | | | | | | | |
| Eligibility Review | X | X | | | | | | | | | | |
| Randomization | | X | | | | | | | | | | |
| VAS | X | | | | | | | | | | | |
| WOMAC$^F$ | | X | | | | | | | | | X | |
| PK Blood Sample | | X | | X | X | X | X | X | X | | | |
| PIIANP Blood Sample | X | | | | | | | | | | X | |
| CTX-II Urine Sample | X | | | | | | | | | | X | |
| Banked Biospecimen Sample-Serum$^G$ | | X | | | | | | | | X | X | |
| Banked Biospecimen Sample | | X | | | | | | | | | | |
| IP Administration | | | X | | | | | | | | | |
| Adverse Events $^H$ | | X | X | X | X | X | X | X | X | X | X | X |

$^A$Day 2 and Day 29 Visits may be conducted via telephone.
$^B$Vital signs collection includes temperature, seated blood pressure, and pulse rate
$^C$Tibial-femoral x-rays to confirm the diagnosis of OA and the Kellgren & Lawrence Grade must be of acceptable quality and acquired within 6 months prior to Screening
$^D$Safety laboratory testing includes hematology, chemistry, and urinalysis
E For women
$^F$The WOMAC should be administered at the beginning of the visit prior to completing other procedures
$^G$Optional banked biospecimen collection
$^H$ Adverse Events are captured starting at time of consent. Any Adverse Events during Screening and Day 1 will be captured and noted as part of medical history
$^I$Screening procedures may be completed across multiple days during the 28 day screening period and do not need to be conducted on consecutive days
$^J$All predose screening assessments should be conducted within 2 hours prior to IP administration
$^K$Subjects may be discharged after at least 2 hours of safety observation following the last procedure

TABLE 24

Schedule of a Multiple-ascending Dose Cohort Schedule of Assessments

| VISIT NAME VISIT | SCREENING | DAY 1$^K$ | | | | | | | | DAY 2A | DAY 8$^K$ | DAY 15$^K$ | DAY 22$^K$ | DAY 29 | DAY 50$^A$ | DAY 90$^M$ | DAY 180$^M$ |
|---|---|---|---|---|---|---|---|---|---|---|---|---|---|---|---|---|---|
| NUMBER | 1$^I$ | 2 | | | | | | | | 3 | 4 | 5 | 6 | 7 | 8 | 9 | 10 |
| TIME POST FIRST DOSE | NA | PRE-DOSE$^J$ | 0 | 15 MIN | 30 MIN | 60 MIN | 90 MIN | 2 HRS | 4 HRS | | | | | | | | |
| ALLOWABLE VISIT WINDOW | −28 to −1 days | | | +/− 2 Min | +/− 3 Min | +/− 5 Min | +/− 5 Min | +/− 5 Min | +/− 5 Min | | +/− 1 Day$^L$ | +/− 1 Day$^L$ | +/− 1 Day$^L$ | +/− 1 Day | + 3 Days | +/− 7 Days | +/− 7 Days |
| Informed Consent | X | | | | | | | | | | | | | | | | |
| Demography | X | | | | | | | | | | | | | | | | |

TABLE 24-continued

Schedule of a Multiple-ascending Dose Cohort Schedule of Assessments

| VISIT NAME VISIT | SCREENING | DAY 1$^K$ | DAY 2A | DAY 8$^K$ | DAY 15$^K$ | DAY 22$^K$ | DAY 29 | DAY 50$^A$ | DAY 90$^M$ | DAY 180$^M$ |
|---|---|---|---|---|---|---|---|---|---|---|
| VISIT NUMBER | 1$^I$ | 2 | 3 | 4 | 5 | 6 | 7 | 8 | 9 | 10 |
| Medical History | X | | | | | | | | | |
| Prior & Concomitant Treatments | X | X | X | X | X | X | X | X | X | X |
| Physical Examination | X | X | | X | | X | | | X | X |
| Height | X | | | | | | | | | |
| Weight | X | X | | X | X | X | X | | X | X |
| Vital Signs$^B$ | X | X X X X X X X | X | X | X | X | | | X | X |
| 12-Lead ECG | X | X | | X | | X | | | X | X |
| Tibial-Femoral Radiographs$^C$ | X | | | | | | | | | |
| Safety Laboratory Tests$^D$ | X | X | | X | | X | | | X | X |
| Follicle Stimulating Hormone Test$^E$ | X | | | | | | | | | |
| Urine Drug Screen | X | | | | | | | | | |
| MRI | X | | | | | | | | X | X |
| Eligibility Review | X | X | | | | | | | | |
| Randomization | | X | | | | | | | | |
| VAS | X | | | | | | | | | |
| WOMAC$^F$ | | X | | X | | X | | | X | X |
| PK Blood Sample | | X X X X X X X | X | X | X | X | | | | |
| PIIANP Blood Sample | | X | | X | X | X | X | | X | X |
| CTX-II Urine Sample | | X | | X | X | X | X | | X | X |
| Banked Biospecimen Sample-Serum$^G$ | | X | X | X | X | X | X | | | |
| Banked Biospecimen Sample-Synovial Fluid$^G$ | | X | | X | X | X | | | | |
| IP Administration | | X | | X | X | X | | | | |
| Adverse Events$^H$ | | X X X X X X X X | X | X | X | X | X | X | X | X |

$^A$Day 2 and Day 50 Visits may be conducted via telephone $^B$Vital signs (temperature, seated blood pressure, and pulse rate) should be collected pre-dose and 30 minutes after dosing on Days 8, 15, and 22

$^C$Tibial-femoral x-rays to confirm the diagnosis of OA and Kellgren & Lawrence Grade must be of acceptable quality and acquired within 6 months prior to Screening $^D$Safety laboratory testing includes hematology, chemistry, and urinalysis $^E$For women $^F$The WOMAC should be administered at the beginning of the visit prior to completing other procedures $^G$Optional banked biospecimen collection $^H$Adverse Events are captured starting at time of consent. Any Adverse Events during Screening and Day 1 will be captured and noted as part of medical history $^I$Screening procedures may be completed across multiple days during the 28 day screening period and do not need to be conducted on consecutive days $^J$All predose screening assessments should be conducted within 2 hours prior to IP administration $^K$Subjects may be discharged after at least 2 hours of safety observation following the last procedure $^L$There should be minimum of 7 days between the IA injections Numbered Embodiments of the Disclosure Notwithstanding the Appended Claims, the Disclosure Sets Forth the Following Numbered Embodiments:
1. A topical composition comprising a therapeutically effective amount of rofecoxib dissolved in a solvent system comprising one or more pharmaceutically acceptable solvents.
2. The topical composition of embodiment 1, wherein the pharmaceutically acceptable solvent system comprises one or more pharmaceutically acceptable solvents selected from the group consisting of acetone (AC), 2-methylpentane-2,4-diol (M24D), alpha-terpineol (AT), benzyl alcohol (BA), diethyl sebacate (DS), diethylene glycol monoethyl ether (DGME), diisopropyl adipate (DIA), dimethyl sulfoxide (DMSO), ethyl acetate (EA), isopropyl tetradecanoate (IPTD), N-methyl-2-pyrrolidone (MP), polyethylene glycol 400 (PEG), polysorbate 20 (PS20), polysorbate 80 (PS80), propylene glycol diacetate (PGD), propylene glycol (PPG), isosorbide dimethyl ether, and propylene carbonate.
3. The topical composition of embodiment 1, wherein the solvent system comprises isosorbide dimethyl ether (DI) and propylene carbonate (PC).
4. The topical composition of embodiment 3, wherein the solvent system further comprises DMSO.
5. The topical composition of embodiment 3, wherein the solvent system comprises from about 10% w/w DI to about 20% w/w DI and from about 3% w/w PC to about 8% w/w PC.
6. The topical composition of embodiment 3, wherein the solvent system comprises about 15% w/w DI and about 5 w/w PC.
7. The topical composition of embodiment 3, wherein the solvent system comprises BA.
8. The topical composition of embodiment 3, wherein the solvent system comprises DMSO.
9. The topical composition of embodiment 3, wherein the solvent system comprises DIA.
10. The topical composition of embodiment 3, wherein the solvent system comprises PS20.
11. The topical composition of embodiment 3, wherein the solvent system comprises BA, DMSO, DIA, and PS20.
12. The topical composition of embodiment 3, wherein the solvent system comprises about 15% w/w DI, about 5% w/w PC, about 3% w/w BA, about 20% w/w DMSO, about 12% w/w DIA, and about 15% w/w PS20.
13. The topical composition of embodiment 1, wherein the therapeutically acceptable amount of rofecoxib is up to 5% w/w.
14. The topical composition of embodiment 1, comprising one or more additional ingredients selected from the group consisting of a humectant, a chelating agent, a UV absorption agent, a moisturizing agent, an excipient, a preservative, a thickening agent, a silicone containing compound, an essential oil, a structuring agent, a vitamin, a pharmaceutical ingredient, and an antioxidant.
15. The topical composition of embodiment 1, comprising oleic acid.
16. A method of applying the topical composition of embodiment 1 to skin, comprising topically applying the topical composition of embodiment 1.
17. A method of reducing inflammation, comprising topically applying the topical composition of embodiment 1.
18. A method of treating arthritis, comprising topically applying the topical composition of embodiment 1.
19. A method of treating acute pain, comprising topically applying the topical composition of embodiment 1.
20. A method of treating migraines, comprising topically applying the topical composition of embodiment 1.
21. The topical composition of embodiment 1, wherein the topical composition is selected from Formulations 1-77, 80, 82, 83, and 85-93.
22. The topical composition of embodiment 1, wherein the topical composition is Formulation 85.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:
1. A topical composition comprising a therapeutically effective amount of from 0.1% w/w to 2.5% w/w rofecoxib dissolved in between about 0.1% w/w and about 15% w/w isosorbide dimethyl ether (DI) and between about 0.1% w/w and about 5% w/w propylene carbonate (PC), and wherein the composition comprises a moisturizing agent selected from the group consisting of oleic acid, beeswax, polysorbate 20 and mineral oil.
2. The topical composition of claim 1, comprising one or more additional pharmaceutically acceptable solvents selected from the group consisting of acetone (AC), 2-methylpentane-2,4-diol (M24D), alpha-terpineol (AT), benzyl alcohol (BA), diethyl sebacate (DS), diethylene glycol monoethyl ether (DGME), diisopropyl adipate (DIA), dimethyl sulfoxide (DMSO), ethyl acetate (EA), isopropyl tetradecanoate (IPTD), N-methyl-2-pyrrolidone (MP), polyethylene glycol 400 (PEG), polysorbate 20 (PS20), polysorbate 80 (PS80), propylene glycol diacetate (PGD), and propylene glycol (PPG).
3. The topical composition of claim 1, wherein the composition comprises about 15% w/w DI.
4. The topical composition of claim 1, wherein the composition comprises about 5% w/w PC.
5. The topical composition of claim 1, wherein the composition comprises about w/w DI and about 5 w/w PC.
6. The topical composition of claim 1, wherein the therapeutically effective amount of rofecoxib is about 2% w/w.
7. The topical composition of claim 1, wherein the therapeutically effective amount of rofecoxib is about 1% w/w.
8. The topical composition of claim 1, wherein the therapeutically effective amount of rofecoxib is about 0.5% w/w.
9. The topical composition of claim 1, comprising from about 0.1% benzyl alcohol (BA) to about 2% w/w BA.
10. The topical composition of claim 9, comprising about 2% w/w BA.
11. The topical composition of claim 1, further comprising dimethyl sulfoxide (DMSO).
12. The topical composition of claim 1, further comprising diisopropyl adipate (DIA).
13. The topical composition of claim 1, further comprising diethylene glycol monoethyl ether (DGME).
14. The topical composition of claim 1, further comprising polysorbate 20 (PS20).
15. The topical composition of claim 1, further comprising oleic acid (OA).

16. The topical composition of claim 1, comprising about 2 w/w benzyl alcohol (BA), about 10% w/w dimethyl sulfoxide (DMSO), and about 10% w/w diisopropyl adipate (DIA).

17. The topical composition of claim 16, further comprising about 15% w/w polysorbate 20 (PS20).

18. The topical composition of claim 16, further comprising about 7.5% w/w oleic acid (OA).

19. The topical composition of claim 16, further comprising from about 0.1% w/w to about 40% w/w diethylene glycol monoethyl ether (DGME).

20. The topical composition of claim 1, further comprising one or more additional ingredients selected from the group consisting of a humectant, a chelating agent, a UV absorption agent, a moisturizing agent, an excipient, a preservative, a thickening agent, a silicone containing compound, an essential oil, a structuring agent, a vitamin, a pharmaceutical ingredient, and an antioxidant.

21. The topical composition of claim 1, wherein the topical composition is selected from the group consisting of: Formulations 30, 36, 41, 50, 53, 57-59, and 85, wherein:
  Formulation 30 comprises DI (14.8% w/w), PC (4.9% w/w), BA (2.6% w/w), oleic acid (OA) (4.9% w/w), DMSO (8.9% w/w), beeswax (3.4% w/w), lanolin (9.9% w/w), mineral oil (48.1% w/w), and rofecoxib (1.9% w/w);
  Formulation 36 comprises DI (15% w/w), PC (5% w/w), DMSO (9.1% w/w), BA (2.6% w/w), OA (5% w/w), Lanolin (10% w/w), Mineral Oil (47.8% w/w), beeswax (3.5% w/w), and rofecoxib (2% w/w);
  Formulation 41 comprises DI (15% w/w), PC (5% w/w), BA (2% w/w), DMSO (10% w/w), OA (5% w/w), PEG-400 (61% w/w), and rofecoxib (2% w/w);
  Formulation 50 comprises DI (15% w/w), PC (5% w/w), BA (2% w/w), DMSO (10% w/w), OA (5% w/w), polyethylene glycol 400 (PEG-400) (40% w/w), ethyl acetate (EA) (21% w/w), and rofecoxib (2% w/w);
  Formulation 53 comprises DI (15% w/w), PC (5% w/w), BA (2% w/w) DMSO (10% w/w), OA (5% w/w), PEG-400 (49% w/w), DIA (12% w/w), and rofecoxib (2% w/w),
  Formulation 57 comprises DI (15% w/w), PC (5% w/w), BA (2% w/w), DMSO (10% w/w), OA (5% w/w), DIA (10% w/w), PEG-400 (52% w/w), and rofecoxib (1% w/w);
  Formulation 58 comprises DI (15% w/w), PC (5% w/w), BA (2% w/w), DMSO (10% w/w), OA (5% w/w), DIA (10% w/w), PEG-400 (51% w/w), and rofecoxib (2% w/w);
  Formulation 59 comprises DI (15% w/w), PC (5% w/w), BA (2% w/w), DMSO (15% w/w), OA (5% w/w), DIA (10% w/w), PEG-400 (47% w/w), and rofecoxib (1% w/w), and
  Formulation 85 comprises DI (15% A w/w); PC (5% w/w); BA (2.5% w/w): DMSO (20% w/w); DIA (12% w/w); DGME (18.5% w/w); PS20 (15% w/w); OA (5% w/w); Hydroxypropyl cellulose 100,000 (4% w/w); rofecoxib 2% (2% w/w); *eucalyptus* oil (0.33% w/w); and spearmint oil (0.67% w/w).

22. The topical composition of claim 1, wherein the topical composition is Formulation 85, wherein Formulation 85 comprises DI (15% w/w); PC (5% w/w); benzyl alcohol (BA) (2.5% w/w): dimethyl sulfoxide (DMSO) (20% w/w): diisopropyl adipate (DIA) (12% w/w); diethylene glycol monoethyl ether (DGME) (18.5% w/w); polysorbate 20 (PS20) (15% w/w); oleic acid (OA) (5% w/w); hydroxypropyl cellulose 100,000 (4% w/w); rofecoxib 2% (2% w/w): *eucalyptus* oil (0.33% w/w); and spearmint oil (0.67% w/w).

23. The topical composition of claim 1, further comprising hydroxypropylcellulose (HPC).

24. The topical composition of claim 1, further comprising *eucalyptus* oil.

25. The topical composition of claim 1, further comprising spearmint oil.

26. A method of reducing inflammation, comprising topically applying the topical composition of claim 1 to the skin at the site of inflammation.

27. A method of treating arthritis in a joint, comprising topically applying the topical composition of claim 1 to the skin at the arthritic joint.

28. The topical composition of claim 1, wherein the moisturizing agent is oleic acid.

* * * * *